(12) United States Patent
Maibach et al.

(10) Patent No.: US 11,344,491 B2
(45) Date of Patent: May 31, 2022

(54) COMPOSITIONS AND METHODS OF USING THE SAME FOR DECONTAMINATION OF SKIN

(71) Applicant: The Regents Of The University Of California, Oakland, CA (US)

(72) Inventors: Howard I. Maibach, San Francisco, CA (US); Xiaoying Hui, Oakland, CA (US); Hanjiang Zhu, San Jose, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/762,934

(22) PCT Filed: Sep. 22, 2016

(86) PCT No.: PCT/US2016/053155
§ 371 (c)(1),
(2) Date: Mar. 23, 2018

(87) PCT Pub. No.: WO2017/053594
PCT Pub. Date: Mar. 30, 2017

(65) Prior Publication Data
US 2018/0271770 A1 Sep. 27, 2018

Related U.S. Application Data

(60) Provisional application No. 62/222,680, filed on Sep. 23, 2015.

(51) Int. Cl.
*A61K 8/81* (2006.01)
*A61K 47/02* (2006.01)
*A61K 47/38* (2006.01)
*A61K 47/34* (2017.01)
*A61K 9/00* (2006.01)
*A61K 8/04* (2006.01)
*A61K 8/90* (2006.01)
*A61Q 17/04* (2006.01)
*A61Q 19/10* (2006.01)

(52) U.S. Cl.
CPC ............ *A61K 8/8176* (2013.01); *A61K 8/044* (2013.01); *A61K 8/8135* (2013.01); *A61K 8/90* (2013.01); *A61K 9/0014* (2013.01); *A61K 47/02* (2013.01); *A61K 47/34* (2013.01); *A61K 47/38* (2013.01); *A61Q 17/04* (2013.01); *A61Q 19/10* (2013.01); *A61K 2800/87* (2013.01)

(58) Field of Classification Search
CPC ......... A61K 8/8176; A61K 8/90; A61Q 17/04
See application file for complete search history.

(56) References Cited

U.S. PATENT DOCUMENTS

| 5,225,189 | A | 7/1993 | Pena |
| 6,652,882 | B1 | 11/2003 | Odidi et al. |
| 10,182,993 | B2 * | 1/2019 | Yang .................... A61K 9/4825 |
| 2007/0098775 | A1 * | 5/2007 | Carrara ................ A61K 31/551 424/449 |
| 2009/0053310 | A1 | 2/2009 | Pilgaonkar et al. |
| 2009/0264436 | A1 | 10/2009 | McKelvey et al. |
| 2010/0016443 | A1 | 1/2010 | Toledano et al. |
| 2012/0003328 | A1 | 1/2012 | Zheng et al. |
| 2014/0234422 | A1 * | 8/2014 | Mathieu ............... A61K 9/5115 424/489 |

FOREIGN PATENT DOCUMENTS

| CN | 103168796 A | * | 6/2013 |
| CN | 104522036 A | * | 4/2015 |

OTHER PUBLICATIONS

Machine translation of CN103168796A, pp. 1-9, Jun. 2013 (Year: 2013).*
Machine translation of CN104522036A, pp. 1-16, Apr. 2015 (Year: 2015).*
Foodadditives (http://www.foodadditivesworld.com/articles/cellulose-gum.html) accessed Jun. 27, 2019, pp. 1-2. (Year: 2019).*
Topical definition (https://dictionary.cambridge.org/us/dictionary/english/topical) accessed Feb. 14, 2020, pp. 1-2 (Year: 2020).*
Gooch, J.W. "Hydrated magnesium aluminum silicate" In: Gooch J.W. (eds) Encyclopedic Dictionary of Polymers. Springer, New York, NY. (2007) https://doi.org/10.1007/978-0-387-30160-0_6001 (Year: 2007).*
Berardi, A. et al. "Hand sanitisers amid CoViD-19: A critical review of alcohol-based products on the market and formulation approaches to respond to increasing demand" International Journal of Pharmaceutics 584 (2020) 119431, pp. 1-14 (Year: 2020).*
Merck (https://www.merckmanuals.com/home/skin-disorders/bacterial-skin-infections/necrotizing-skin-infections) Apr. 2021, pp. 1-3 (Year: 2021).*
Olsen, C.B. "A possible cure for death" Med Hypotheses May 1988;26(1):77-84, p. 1 (Year: 1988).*
Landau, E. "What polonium does to the body" (https://www.cnn.com/2012/11/27/health/polonium-arafat-explainer/index.html) Nov. 29, 2012. pp. 1-8 (Year: 2012).*
Brazier, Y. "What to know about radiation sickness" (https://www.medicalnewstoday.com/articles/219615) Aug. 15, 2017. pp. 1-21 (Year: 2017).*

(Continued)

*Primary Examiner* — Andrew S Rosenthal
(74) *Attorney, Agent, or Firm* — Ballard Spahr LLP

(57) ABSTRACT

The present disclosure provides compositions comprising decontaminating compounds, and pharmaceutically acceptable salts thereof and methods of treating or preventing a contamination in a mammal, in particular, the composition can include a mixture of polyvinyl acetate and povidone, a coblock polymer of ethylene oxide and propylene oxide, a polyvinyl alcohol, or combinations thereof, and an aqueous suspending agent.

12 Claims, 29 Drawing Sheets

(56) References Cited

OTHER PUBLICATIONS

Choudhary, G et al., Development of controlled release formulations of carbofuran and evaluation of their efficacy against Meloidogyne incognita, Journal of Agricultural and Food Chemistry, 2006, 54:4727-4733.
International Search Report and Written Opinion of the International Searching Authority for PCT/US2016/053155 dated Dec. 2, 2016.
International Preliminary Report on Patentability for PCT/US2016/053155 dated Mar. 27, 2018.

* cited by examiner

COMPOSITIONS AND METHODS OF USING THE SAME FOR DECONTAMINATION OF SKIN

CROSS-REFERENCE TO RELATED APPLICATIONS

This application is based on international application number PCT/US16/53155 which designated the United States of America and was filed under 35 U.S.C. § 120, which claims priority to U.S. Provisional Ser. No. 62/222,680, filed on Sep. 23, 2015, which is herein incorporated by reference in its entirety.

CROSS-REFERENCE TO RELATED APPLICATIONS

This application claims priority to U.S. Provisional Patent Application Ser. No. 62/222,680 filed Sep. 23, 2015, the entire contents of which is incorporated herein by reference.

FIELD OF THE INVENTION

The present disclosure is directed, in part, to compositions capable of decontaminating the skin and/or protecting from contamination by a wide range of chemical and non-chemical substances and methods of using the same.

BACKGROUND OF THE INVENTION

The stratum corneum (SC) is the outermost layer of the skin, consisting of about 15 to layers of dead conneocytes, flattened cells. The SC forms a barrier to protect underlying tissue from, for example, infection, dehydration, chemical contamination, and mechanical stress. Cells of the SC contain a dense network of keratin, a protein that helps to prevent water evaporation. These cells can also absorb water, further aiding in hydration.

During chemical contamination, chemicals present on the skin surface can be absorbed into the SC within seconds to minutes of exposure. Critically, these chemicals can also remain in the SC, forming a type of chemical reservoir. Standard water based decontamination methods, such as soap-water washing, can enhance the skin penetration of a wide range of chemical contaminants. This "water wash-in" effect drastically reduces the effectiveness of using water-based skin decontamination methods.

What is needed is a compound formulation that is capable of decontaminating the skin, including extracting chemicals currently stored in the SC. The present disclosure relates to a group of such compounds that provide safe and effective skin decontamination and their methods of use.

SUMMARY OF THE INVENTION

The present disclosure provides a composition comprising: a mixture of a compound having formula:

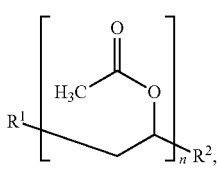

Formula 100 or pharmaceutically acceptable salt thereof, and a compound having formula:

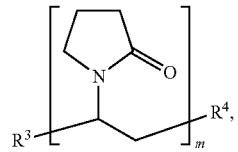

Formula 110 or pharmaceutically acceptable salt thereof; wherein n is any integer from about 1 to about 5000, and m is any integer from 1 to 500; and wherein $R^1$, $R^2$, $R^3$, and $R^4$ are each independently chosen from cyano, halo, alkyl, guanidino, haloakyl, heterocyclic, heteroaryl, phenyl, hydroxyl, amine or amide.

The present disclosure provides a composition comprising: a mixture of a compound having formula:

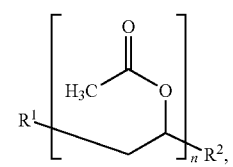

Formula 100 or pharmaceutically acceptable salt thereof, and a compound having formula:

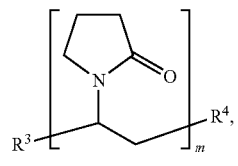

Formula 110 or pharmaceutically acceptable salt thereof; wherein n is any integer from 1 to 50000, and m is any integer from 1 to 5000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: a mixture of a compound having formula:

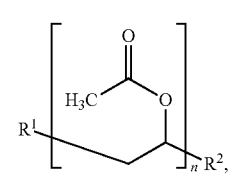

Formula 100 or pharmaceutically acceptable salt thereof, and a compound having formula:

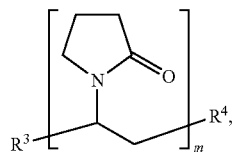

Formula 110 or pharmaceutically acceptable salt thereof; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: (i) a mixture of a compound having formula:

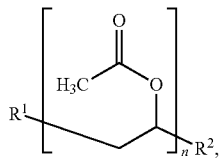

Formula 100 or pharmaceutically acceptable salt thereof, and a compound having formula:

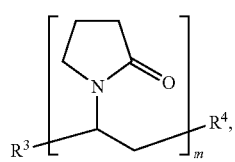

Formula 110 or pharmaceutically acceptable salt thereof; and (ii) a coblock polymer of ethylene oxide and propylene oxide (e.g., Lutrol®) or pharmaceutically acceptable salt thereof; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: (i) a mixture of a compound having formula:

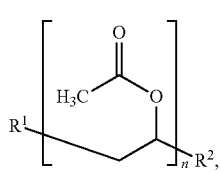

Formula 100 or pharmaceutically acceptable salt thereof, and a compound having formula:

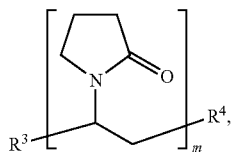

Formula 110 or pharmaceutically acceptable salt thereof; and (ii) a clay powder or pharmaceutically acceptable salt thereof; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: (i) a mixture of a compound having formula:

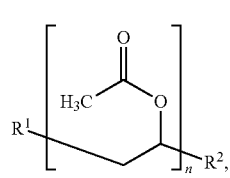

Formula 100 or pharmaceutically acceptable salt thereof, and a compound having formula:

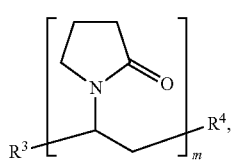

Formula 110 or pharmaceutically acceptable salt thereof; and (ii) a silicate or pharmaceutically acceptable salt thereof; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: (i) a mixture of a compound having formula:

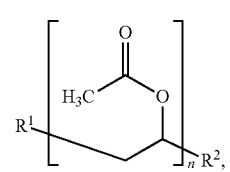

Formula 100 or pharmaceutically acceptable salt thereof, and a compound having formula:

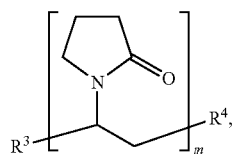

Formula 110 or pharmaceutically acceptable salt thereof; (ii) a coblock polymer of ethylene oxide and propylene oxide or pharmaceutically acceptable salt thereof; and (iii) a clay powder or pharmaceutically acceptable salt thereof; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

The present disclosure provides a composition comprising: (i) a mixture of a compound having formula:

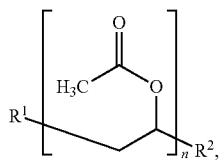

Formula 100 or pharmaceutically acceptable salt thereof, and a compound having formula:

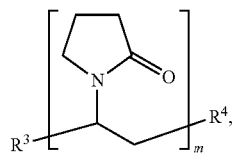

Formula 110 or pharmaceutically acceptable salt thereof; and (ii) a coblock polymer of ethylene oxide and propylene oxide or pharmaceutically acceptable salt thereof; and (iii) at least one aqueous suspending agent; wherein n is any integer from 1 to 6000, and m is any integer from 1 to 500; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

In some embodiments, the disclosure provides a composition comprising: (i) a mixture of a compound having formula:

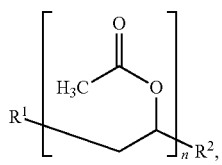

Formula 100 or pharmaceutically acceptable salt thereof, and a compound having formula:

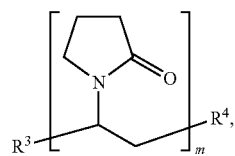

Formula 110 or pharmaceutically acceptable salt thereof; and (ii) a coblock polymer of ethylene oxide and propylene oxide or pharmaceutically acceptable salt thereof; and (iii) at least one aqueous suspending agent; wherein n is any integer from 1 to 10000, and m is any integer from 1 to 1000; and wherein $R^1$, $R^2$, $R^3$, and $R^4$ are each independently chosen from: cyano, halo, alkyl, guanidino, haloakyl, heterocyclic, heteroaryl, phenyl, hydroxyl, amine or amide.

In some embodiments, the disclosure provides a composition comprising: (i) a mixture of a compound having formula:

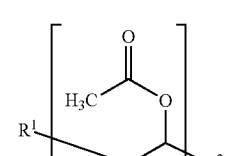

Formula 100 or pharmaceutically acceptable salt thereof, and a compound having formula:

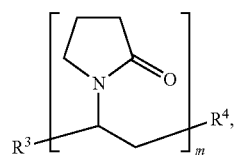

Formula 110 or pharmaceutically acceptable salt thereof; and (ii) a coblock polymer of ethylene oxide and propylene oxide or pharmaceutically acceptable salt thereof; and (iii) at least one aqueous suspending agent; wherein n is any integer from 1 to 6000, and m is any integer from 1 to 500; and wherein $R^1$, $R^2$, $R^3$, and $R^4$ are each independently chosen from: cyano, halo, alkyl, alkenyl, alkoxy, guanidino, haloakyl, heterocyclic, heteroaryl, phenyl, hydroxyl, amine or amide.

In some embodiments, the disclosure provides a composition comprising: (i) a mixture of a compound having formula:

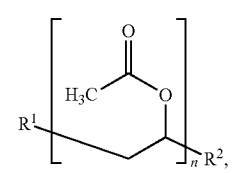

Formula 100 or pharmaceutically acceptable salt thereof, and a compound having formula:

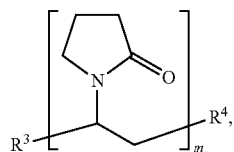

Formula 110 or pharmaceutically acceptable salt thereof; and (ii) a coblock polymer of ethylene oxide and propylene oxide or pharmaceutically acceptable salt thereof; and (iii) at least one aqueous suspending agent; wherein n is any integer from 1 to 10000, and m is any integer from 1 to 1000; and wherein $R^1$, $R^2$, $R^3$, and $R^4$ are each independently chosen from: a $C_1$-$C_6$ alkyl, hydroxyl, halo, amine or amide.

In some embodiments, the disclosure provides a composition comprising: (i) a mixture of a compound having formula:

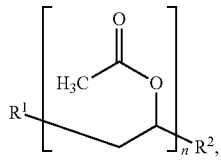

Formula 100 or pharmaceutically acceptable salt thereof, and a compound having formula:

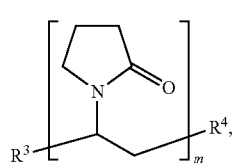

Formula 110 or pharmaceutically acceptable salt thereof; and (ii) a coblock polymer of ethylene oxide and propylene oxide or pharmaceutically acceptable salt thereof; and (iii) at least one aqueous suspending agent; wherein n is any integer from 1 to 10000, and m is any integer from 1 to 1000; and wherein $R^1$, $R^2$, $R^3$, and $R^4$ are each independently chosen from: a methyl, ethyl, hydroxyl, amine or amide.

In some embodiments, the disclosure provides a composition comprising: (i) a mixture of a compound having formula:

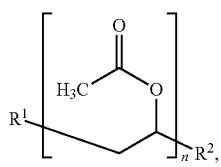

Formula 100 or pharmaceutically acceptable salt thereof and, a compound having formula:

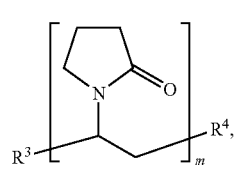

Formula 110 or pharmaceutically acceptable salt thereof; and (ii) a coblock polymer of ethylene oxide and propylene oxide or pharmaceutically acceptable salt thereof; (iii) water; and (iv) ethanol, wherein n is any integer, and m is any integer less than 10000; and wherein $R^1$, $R^2$, $R^3$, and $R^4$ are each independently chosen from: a methyl, ethyl, hydroxyl, amine or amide.

In some embodiment, the disclosure provides a composition comprising: (i) a mixture of a compound having formula:

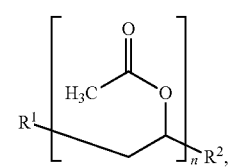

Formula 100 or pharmaceutically acceptable salt thereof and, a compound having formula:

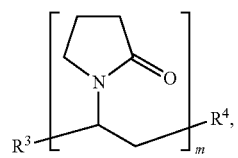

Formula 110 or pharmaceutically acceptable salt thereof; and (ii) a coblock polymer of ethylene oxide and propylene oxide or pharmaceutically acceptable salt thereof; (iii) water; and (iv) ethanol, wherein n is any integer from about 5 to about 10000, and m is any integer from about 5 to about 1000; and wherein $R^1$, $R^2$, $R^3$, and $R^4$ are each independently chosen from: a methyl, ethyl, hydroxyl, amine or amide.

In some embodiments, the mixture of compounds having formulas 100 and 110 is Kollidon® SR. In some embodiments, the coblock polymer of ethylene oxide and propylene oxide is Lutrol® F127 or pharmaceutically acceptable salt thereof.

In some embodiments, the composition further comprises carboxymethyl cellulose or pharmaceutically acceptable salt thereof. In some embodiments, the composition further comprises clay powder or pharmaceutically acceptable salts thereof. In some embodiments, the composition further comprises a phyllosilicate or pharmaceutically acceptable salt thereof.

In some embodiments, the mixture of compounds having formulas 100 and 110 is Kollidon® SR, wherein the coblock polymer of ethylene oxide and propylene oxide is Lutrol® F127, and wherein the composition further comprises carboxymethyl cellulose, clay powder, and bentonite. In some embodiments, the at least aqueous solvent or suspending agent is water, ethanol, or water and ethanol. In some embodiments, the at least aqueous solvent or suspending agent is isopropyl alcohol or isopropyl myristate.

In some embodiments, the composition comprises: (i) a mixture of a compound having formula:

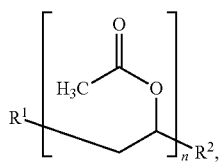

Formula 100 or pharmaceutically acceptable salt thereof, and a compound having formula:

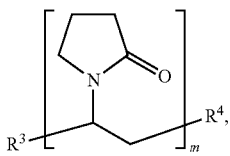

Formula 110 or pharmaceutically acceptable salt thereof; and (ii) a phyllosilicate or pharmaceutically acceptable salt thereof; (iii) clay powder; and (iv) at least one aqueous suspending agent; wherein n is any integer from 1 to 6000, and m is any integer from 1 to 500; and wherein $R^1$, $R^2$, $R^3$, and $R^4$ are each independently chosen from: cyano, halo, alky, guanidino, haloakyl, heterocyclic, heteroaryl, phenyl, hydroxyl, amine or amide; wherein the composition optionally comprises a viscosity-enhancing agent.

In some embodiments, the weight percentage of the mixture of the compounds as part of the total weight of the composition is from about from about 5% to about 20%. In some embodiments, the weight percentage of the mixture of the compounds as part of the total weight of the composition is from about from about 2% to about 50%. In some embodiments, the weight percentage of the coblock polymer of ethylene oxide and propylene oxide or pharmaceutically acceptable salt thereof as part of the total weight of the composition is from about 1% to about 5%. In some embodiments, the weight percentage of the coblock polymer of ethylene oxide and propylene oxide or pharmaceutically acceptable salt thereof as part of the total weight of the composition is from about 1% to about 10%. In some embodiments, the weight percentage of carboxymethyl cellulose or pharmaceutically acceptable salt thereof as part of the total weight of the composition is from about 1% to about 5%. In some embodiments, the weight percentage of carboxymethyl cellulose or pharmaceutically acceptable salt thereof as part of the total weight of the composition is from about 1% to about 15%. In some embodiments, the weight percentage of clay powder or pharmaceutically acceptable salt thereof as part of the total weight of the composition is from about 10% to about 25%. In some embodiments, the weight percentage of clay powder or pharmaceutically acceptable salt thereof as part of the total weight of the composition is from about 5% to about 40%. In some embodiments, the weight percentage of phyllosilicate or pharmaceutically acceptable salt thereof as part of the total weight of the composition is from about 1% to about 10%. In some embodiments, the weight percentage of phyllosilicate or pharmaceutically acceptable salt thereof as part of the total weight of the composition is from about 1% to about 25%. In some embodiments, the weight percentage of ethanol as part of the total weight of the composition is from about 20% to about 50%. In some embodiments, the weight percentage of ethanol as part of the total weight of the composition is from about 5% to about 60%. In some embodiments, the weight percentage of water as part of the total weight of the composition is from about 10% to about 50%. In some embodiments, the weight percentage of water as part of the total weight of the composition is from about 5% to about 60%.

In some embodiments, the composition comprises from about 5% to about 20% weight percentage of Kollidon® SR or pharmaceutically acceptable salt thereof as part of the total weight of the composition; from about 1% to about 5% weight percentage of Lutrol® F127 or pharmaceutically acceptable salt thereof as part of the total weight of the composition; from about 1% to about 5% weight percentage of carboxymethyl cellulose or pharmaceutically acceptable salt thereof as part of the total weight of the composition; from about 10% to about 25% weight percent of clay powder or pharmaceutically acceptable salt thereof as part of the total weight of the composition; from about 1% to about 10% weight percent of a phyllosilicate or pharmaceutically acceptable salt thereof as part of the total weight of the composition; from about 20% to about 50% weight percent of ethanol as part of the total weight of the composition; and from about 10% to about 50% weight percent of water as part of the total weight of the composition.

In some embodiments, the phyllosilicate is bentonite. In some embodiments, the composition is in the form of an aqueous gel. In some embodiments, the composition is in the form of a cream. In some embodiments, the composition is in the form of a spray. In some embodiments, the composition is in the form of a foam or an ointment.

The present disclosure also provides a kit comprising any of the compositions described herein and an applicator.

The present disclosure also provides a method of manufacturing any of the composition described herein, comprising mixing the mixture of compounds having Formula 100 and Formula 110 with the coblock polymer of ethylene oxide and propylene oxide, and adding water and ethanol to the mixture.

In some embodiments, the carboxymethyl cellulose, the clay powder, and the phyllosilicate are mixed with the coblock polymer of ethylene oxide and propylene oxide and the mixture of compounds comprising Formula 100 and Formula 110 before adding one or a plurality of liquid solvents or suspending agents to the composition. In some embodiments, the method further comprises a step of storing the composition after adding the water and ethanol to the composition. In some embodiments, the method further comprises a step of storing the composition after adding the water and ethanol to the composition for a period of no less than about twenty-four hours. In some embodiments, the clay powder is Fuller's earth.

The present disclosure also provides a method of decontaminating a subject in need of decontamination comprising contacting any one or more compositions disclosed herein to the skin of the subject at or proximate to a location of the subject's body where the skin has been exposed to a disease-causing agent.

In some embodiments, the step of contacting is performed no less than 10 minutes after the subject is exposed to the disease-causing agent. In some embodiments, the step of contacting is performed no less than about 20 minutes after the subject is exposed to the disease-causing agent. In some embodiments, the step of contacting is performed no less than about 30 minutes after the subject is exposed to the disease-causing agent. In some embodiments, the step of contacting is performed no less than about 2 hours after the subject is exposed to the disease-causing agent. In some embodiments, the step of contacting is performed no less than about 5 hours after the subject is exposed to the disease-causing agent.

In some embodiments, the method further comprises massaging the any one or more of the compositions described herein into the skin of the subject at a location of the subject's body where the skin has been exposed to a disease-causing agent for about 1, 2, 3 or more minutes after contacting the composition to the skin of the subject.

In some embodiments, the method further comprises removing the any one or more of the compositions described herein from the skin of the subject in need thereof after contacting any one or more of the compositions described herein to the skin of the subject at a location of the subject's body where the skin has been exposed to a contaminant.

In some embodiments, the method further comprises allowing the any one or more of the compositions described herein to remain on the skin for at least about 5 minutes prior to removing the any one or more of the compositions described herein from the skin of the subject in need thereof. In some embodiments, the method further comprises allowing the any one or more of the compositions described herein to remain on the skin for at least about 30 minutes prior to removing the any one or more of the compositions described herein from the skin of the subject in need thereof. In some embodiments, the method further comprises allowing the any one or more of the compositions described herein to remain on the skin for at least about 60 minutes prior to removing the any one or more of the compositions described herein from the skin of the subject in need thereof.

In some embodiments, the step of removing the any one or more of the compositions described herein is performed by rubbing and/or rinsing the one or more compositions from the skin by the use of a liquid, semi-solid, and/or solid. In some embodiments, the step of removing the any one or more of the compositions described herein is performed by rinsing the one or more compositions from the skin by the use of a decontamination solution. In some embodiments, the step of removing the any one or more of the compositions described herein is performed by rinsing and/or rubbing the one or more compositions from the skin by the use of a decontamination medium. In some embodiments, the step of removing the any one or more of the compositions described herein is performed by peeling a after the one or more compositions has hardened or coalesced into a solid or semi-solid.

The present disclosure also provides a method of preventing death, toxicity, and/or skin damage of a subject exposed to a contaminant comprising contacting any one or more of the compositions described herein to the skin of the subject at a location of the subject's body at or proximate to a location of the skin where the skin has been exposed to the contaminant.

In some embodiments, the step of contacting is performed no less than 1 minute after the subject is exposed to the disease-causing agent. In some embodiments, the step of contacting is performed no less than 10 minutes after the subject is exposed to the disease-causing agent. In some embodiments, the step of contacting is performed no less than about 20 minutes after the subject is exposed to the disease-causing agent. In some embodiments, the step of contacting is performed no less than about 30 minutes after the subject is exposed to the disease-causing agent. In some embodiments, the step of contacting is performed no less than about 2 hours after the subject is exposed to the disease-causing agent. In some embodiments, the step of contacting is performed no less than about 5 hours after the subject is exposed to the disease-causing agent.

In some embodiments, the method further comprises allowing the any one or more of the compositions described herein to remain on the skin for at least about 30 minutes prior to removing the any one or more of the compositions described herein from the skin of the subject in need thereof.

In some embodiments, the step of removing the any one or more of the compositions described herein is performed by rinsing the one or more compositions from the skin by the use of a liquid. In some embodiments, the step of removing the any one or more of the compositions described herein is performed by rinsing the one or more compositions from the skin by the use of a decontamination solution. In some embodiments, the step of removing the any one or more of the compositions described herein is performed by rinsing the one or more compositions from the skin by the use of a decontamination solution and a solid or semi-solid.

The present disclosure also provides a method of increasing the efficiency of removing contaminant from the skin comprising contacting any one or more of the compositions described herein to the skin of the subject at a location of the subject's body where the skin has been exposed to the contaminant. The present disclosure also provides a method of increasing the efficiency of preventing contamination of the skin comprising contacting any one or more of the compositions described herein to the skin of the subject at a location of the subject's body where the skin has been exposed to the contaminant.

The present disclosure also provides a method of decreasing the amount of exposure of a contaminant to the stratum corneum of a subject exposed to an irritant and/or disease-causing comprising contacting any one or more of the compositions described herein to the skin of the subject at a location of the subject's body where the skin has been exposed to the contaminant.

BRIEF DESCRIPTION OF DRAWINGS

FIG. 10 depicts the percent lethality when soap-water washing, RSDL and DDG decontamination were delayed.

FIG. 1 depicts the comparison of decontamination efficiency of soap-water wash and DDGel following 2 to 30 minutes of post dermal exposure by panthenol (FIG. 11A), salicylic acid (FIG. 11B) and butenafine HCl (FIG. 11C) in Example 5.

DETAILED DESCRIPTION OF EMBODIMENTS

Figure 1:
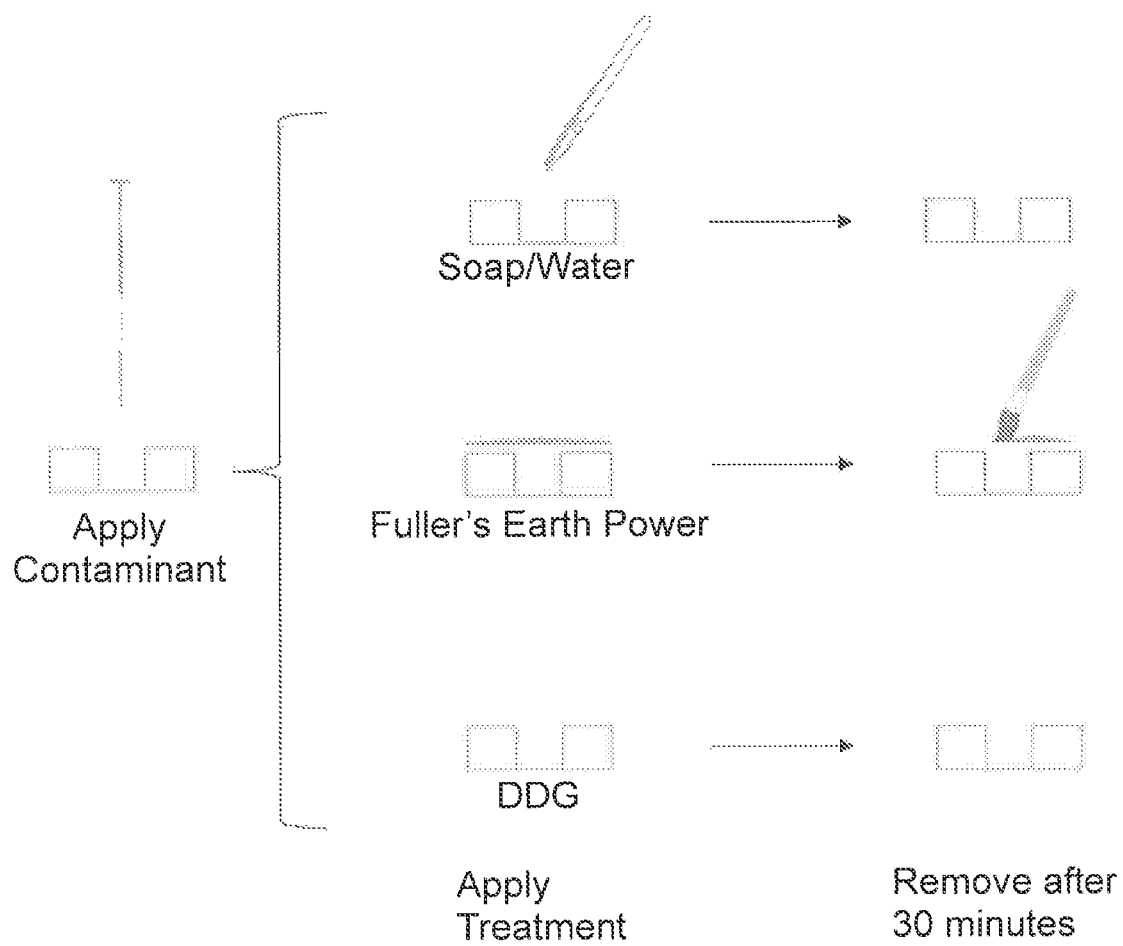
FIG. 1 depicts a flow diagram of a decontamination experiment using human skin. After application of contaminant, treatment is applied (soap and water, Fuller's Earth Powder, or DDG. For purposes of this application, DDG refers to the substance identified in Table 5). After 30 minutes treatment is removed if necessary and contamination testing can begin on skin samples.

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "alkenyl" means a straight or branched alkyl group having one or more double carbon-carbon bonds and 2-20 carbon atoms, including, but not limited to, ethenyl, I-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

As used herein, the term "alkoxy" means a straight or branched —O-alkyl group of 1 to 20 carbon atoms, including, but not limited to, methoxy, ethoxy, n-propoxy, iso-propoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-22-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "animal" includes, but is not limited to, humans and non-human vertebrates such as wild, domestic, and farm animals.

As used herein, the phrase "therapeutically effective amount" of a compound can be measured by calculating the decontaminating efficiency of the compound. In some embodiments, a therapeutically effective amount is the amount of one or a plurality of compositions disclosed herein that prevents the spread, reduces the severity, or removes at least a portion of a contaminant from the skin of a subject who has been exposed to the contaminant or is likely to be exposed by a contaminant. In some embodiments, the therapeutically effective amount reduces the likelihood of suffering from a disease or condition caused by exposure to a contaminant by at least 10%, by at least 20%, by at least 30%, by at least 40%, by at least 50%, by at least 60%, by at least 70%, by at least 80%, by at least 90%, or by at least 95% as compared to a subject who is exposed to the contaminant and is not treated with the therapeutically effective amount. In some embodiments, an "effective amount" is also a "therapeutically effective amount" whereby the compound reduces or eliminates at least one harmful effect of a subject being exposed to a contaminant.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein "disease-causing agent," used interchangeably with "toxin" or "contaminant" means any chemical compound (including peptides, nucleic acids, prions, or hybrids thereof) or complex structure of chemical compounds, that causes or increases the likelihood of developing an ailment in a subject. In some embodiments, the disease-causing agent is one or a plurality of chemical warfare agents (CWAs), T-2 toxin, pesticide-related chemicals, or radioactive substances comprising any one or more chemical isotopes. In some embodiments, the radioactive substance comprises one or more of the following isotopes: $^2$H, $^3$H, $^{13}$C, $^{14}$C, $^{15}$N, $^{16}$O, $^{17}$O, $^{31}$P, $^{32}$P, $^{35}$S, $^{18}$F, $^{36}$Cl, $^{225}$Ac, $^{225}$Ac, $^{212}$Bi, $^{213}$Bi, $^{109}$Cd, $^{60}$Co, $^{64}$Cu, $^{67}$Cu, $^{166}$Dy, $^{169}$Er, $^{152}$Eu, $^{154}$Eu, $^{153}$Gd, $^{198}$Au, $^{166}$Ho, $^{125}$I, $^{131}$I, $^{192}$Ir, $^{177}$Lu, $^{99}$Mo, $^{194}$Os, $^{103}$Pd, $^{195m}$Pt, $^{32}$P, $^{33}$P, $^{223}$Ra, $^{186}$Re, $^{188}$Re, $^{105}$Rh, $^{145}$Sm, $^{153}$Sm, $^{47}$Sc, $^{75}$Se, $^{85}$Sr, $^{89}$Sr, $^{99m}$Tc, $^{228}$Th, $^{229}$Th, $^{170}$Tm, $^{117m}$Sn, $^{188}$W, $^{127}$Xe, $^{175}$Yb, $^{90}$Y, $^{91}$Y. In some embodiments, the contaminant is chosen from one or a combination of: GA (tabun), GB (sarin), GD (soman), GF (cyclohexyl sarin), VX (nerve agent), HD (mustard), T-2 toxin, Parathion, Paraoxon, Parathion-methyl, Paraoxon-methyl. Malathion, Malaoxon, Chlorpyrifos. In some embodiments, the contaminant comprises one or a plurality of pathogenic bacterial strains such as: *Salmonella, Neisseria, Brucella, Mycobacterium, Listeria, Francisella, Legionella, Yersinia pestis, Acinetobacter baumannii, Escherichia coli, Pseudomonas* species, *Klebsiella* species, *Proteus* species, *Enterobacter cloacae, coliform bacteria, Serratia* species, *Citrobacter* species and *Providencia* species.

In some embodiments, the disease-causing agent is one or a plurality of allergens, such as pollen, dust, dust mite excretion, pet dander, urushiol, latex particulate.

As used herein, the term "guanidino" means —NHC(=NH)NH$_2$.

As used herein, the term "halo" means halogen groups including, but not limited to fluoro, chloro, bromo, and iodo.

As used herein, the term "haloalkyl" means a C$_{1-6}$ alkyl group having one or more halogen substituents. Examples of haloalkyl groups include, but are not limited to, —CF$_3$, —C$_2$F$_5$, —CHF$_2$, —CCl$_3$, —CHCl$_2$, —C$_2$Cl$_5$, —CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heterocycle" "heterocyclic" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. The heterocyclic groups can be unsubstituted or substituted with an alkyl to form a heterocycloalkyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, isoindolin-1-one-3-yl,5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "individual" or "patient" or "subject," used interchangeably, means any animal, including mammals, such as mice, rats, other rodents, rabbits, dogs, cats, swine, cattle, sheep, horses, or primates, such as humans. In some embodiments, the subject is a non-human animal.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular exposure to a particular contaminant or disease-causing agent is prevalent.

As used herein, the phrase "integer from X to Y" where X is any integer and Y is any integer greater than X, means that the range of integers includes X, Y, and any integers between X and Y. For instance if the application discloses "any integer less than "integer from 0 to 5" or "0-5" means 0, 1, 2, 3, 4, or 5. In some embodiments, the value of n and m in Formulas 100 and 110 is a range from 1 to about 100, from 1 to about 200, from 1 to about 300, from 1 to about 400, from 1 to about 500, from 1 to about 600 from 1 to about 700, from 1 to about 800, from 1 to about 900, from 1 to about 1000, from 1 to about 1500, from 1 to about 1600, from 1 to about 1700, from 1 to about 1800, from 1 to about 1900, or from 1 to about 2000.

As used herein, the term "isolated" means that the compounds described herein are separated from other components of either (a) a natural source, such as a plant or cell, such as a bacterial culture, or (b) a synthetic organic chemical reaction mixture, such as by conventional techniques.

As used herein, the term "Kollidon® SR" means any mixture of polyvinyl acetate and povidone. In some embodiments, Kollidon® SR comprises mixed polymers of polyvinyl acetate and povidone or polymers with the same monomer of polyvinyl acetate and the same monomer of povidone. In some embodiments, the Kollidon® SR is in powdered or granule form. In some embodiments, Kollidon® SR comprises any mixture of the same or different monomers of polyvinyl acetate and povidone and further comprises one or a combination of stabilizers. In some embodiments, Kollidon® SR comprises any mixture of the same or different monomers of polyvinyl acetate and povidone and further comprises one or a combination of stabilizers, wherein the stabilizers are sodium lauryl sulfate and silica. In some embodiments comprising sodium lauryl sulfate and silica the weight of sodium lauryl sulfate is about 0.8% and the weight of silica is about 0.2% of the total weight of Kollidon® SR. In some embodiments, Kollidon® SR comprises any mixture of the same or different monomers of polyvinyl acetate and povidone; sodium lauryl sulfate; and silica, wherein the weight percent (w/w) of sodium lauryl sulfate is about 0.8% and the weight percent of silica is about 0.2%; wherein the weight percent of polyvinyl acetate is about 80% and the weight percent of povidone is about 19% of the total weight of Kollidon® SR. In some embodiments, the Kollidon® SR can include about 60, 65, 70, 71, 72, 73, 74, 75, 76, 77, 78, 79, 80, 81, 82, 83, 84, 85, 86, 87, 88, 89, 90 or about 95 weight percent of polyvinyl acetate. These values can be used to define a range, such as from about 75 weight percent to about 85 weight percent. In other embodiments, the Kollidon® SR can include about 5, 10, 11, 12, 13, 14, 15, 16, 17, 18, 19, 20, 21, 22, 23, 24, 25, 26, 27, 28, 29, 30, 35 or about 40 weight percent of povidone. These values can be used to define a range, such as from about 15 weight percent to about 25 weight percent.

As used herein, the term "Lutrol® coblock polymer" means any synthetic block copolymer of ethylene oxide and propylene oxide. In some embodiments, the Lutrol® coblock polymer is has the following structure:

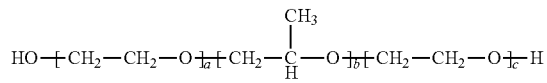

wherein each a is any integer between 1 and 5000, and b any integer between 1 and 5000. In some embodiments the Lutrol® coblock polymer is selected from one or a plurality of the following species:

Wherein a and b blocks have the following values:

| Lutrol | Poloxamer | a | b |
|---|---|---|---|
| L 44 | 124 | 12 | 20 |
| F 68 | 188 | 80 | 27 |
| F 87 | 237 | 64 | 37 |
| F 108 | 338 | 141 | 44 |
| F 127 | 407 | 101 | 56 |

As used herein, the term "silicate" means any salt or ester of silicic acid. In some embodiments, the silicate is an insoluble salt with polymeric negative ions having a structure formed of tetrahedrons of $SiO_4$ groups linked in rings, chains, sheets, or three-dimensional frameworks. In some embodiments, the silicate is a phyllosilicate or pharmaceutically acceptable salt thereof. In some embodiments, the silicate is a phyllosilicate or pharmaceutically acceptable salt thereof chosen from one or a combination of: ajoite, allophane, annite, apophyllite, bentonite, biotite, bowenite, brammallite, carletonite, caryopilite, cavansite, chamosite, chapmanite, chrysocolla, clay, clay minerals, clintonite, cymrite, delessite, dickite, ekanite, ephesite, expanded clay aggregate, fraipontite, franklinphilite, fuchsite, greenalite, halloysite, hisingerite, imogolite, kampfite, kaolinite, kegelite, kerolite, lepidolite, macaulayite, magadiite, medicinal clay, meerschaum, metal clay, mica, minnesotaite, nelenite, neptunite, okenite, organoclay, pentagonite, phlogopite, pimelite, pyrophyllite, sanbornite, searlesite, sepiolite, seraphinite, sericite, siderophyllite, soapstone, stilpnomelane, talc, thuringite, tuperssuatsiaite, issingite, zakharovite, and zussmanite.

As used herein, the term "clay powder" means any clay material that has the capability to decolorize or absorb oil, other liquids, or contaminants. In some embodiments, the clay powder comprises aluminum silicates and clay mineral of varying composition. In some embodiments, the clay powder is Fuller's earth.

As used herein, the term "mammal" means any animal from the Family Mammalia, such as a rodent (i.e., a mouse, a rat, or a guinea pig), a monkey, a cat, a dog, a cow, a horse, a pig, or a human. In some embodiments, the mammal is a human.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present disclosure also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder. In some embodiments, the prevention means a reduction of acquiring a particular disease, condition, or disorder after contamination by a contaminant.

As used herein, the term "purified" means that when isolated, the isolate contains at least 90%, at least 95%, at least 98%, or at least 99% of a composition described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the phrase "solubilizing agent" means agents that result in formation of a micellar solution or a true solution of the composition.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$ heteroaryl, $C_3$-$C_6$ cycloalkyl, $C_5$-$C_6$ aryloxy, —CN, —OH, oxo, halo, haloalkyl, —$NO_2$, —$CO_2H$, —$NH_2$, —$NH(C_1$-$C_8$alkyl), —$N(C_1$-$C_8$alkyl)$_2$, —$NH(C_6$aryl), —$N(C_5$-$C_6$aryl)$_2$, —ClO, —$CO(C_1$-$C_6$alkyl), —$CO((C_5$-$C_6)$aryl), —$CO_2((C_1$-$C_6)$alkyl), and —$CO_2((C_5$-$C_6)$aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes of this disclosure, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of decontamination" or "treating contamination" means an activity that prevents, alleviates or ameliorates any of the primary phenomena or secondary symptoms associated with the exposure of a subject to a compound that contaminates the subject.

At various places in the present specification, substituents of compounds may be disclosed in groups or in ranges. It is specifically intended that the disclosure include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It is understood that the present disclosure encompasses the use, where applicable, of stereoisomers, diastereomers and optical stereoisomers of the compounds of the disclosure, as well as mixtures thereof. Additionally, it is understood that stereoisomers, diastereomers, and optical stereoisomers of the compounds of the disclosure, and mixtures thereof, are within the scope of the disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methyl-benzyl-amine (e.g., Sand R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Although the disclosed compositions comprise compounds are suitable for decontamination of the skin of a subject, other functional groups can be incorporated into the compound with an expectation of similar results. In particular, thioamides and thioesters are anticipated to have very similar properties. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—NH$_2$." Thus, in any structure depicted herein wherein a valency is open, a hydrogen atom is implicit, and is only omitted for brevity.

The present disclosure provides pharmaceutical compositions comprising a compound having Formula 100 and/or Formula 110, whereby at least at one end of the polymer, or a pharmaceutically acceptable salt thereof, includes at least one R group. In some embodiments, each R group can, independently, be chosen from $C_1$-$C_3$alkyl, $C_1$-$C_3$alkoxy, halo, and halo$C_1$-$C_3$alkyl.

In some embodiments, each R group, i.e., $R^1$, can, independently, be chosen from $C_1$-$C_2$alkyl, halo, and halo$C_1$-$C_2$alkyl. In some embodiments, each R group, i.e., $R^1$, can, independently, be chosen from halo and halo$C_1$-$C_2$alkyl. In some embodiments, each R group, i.e., $R^1$, can, independently, be chosen from halo and halomethyl. In some embodiments, each R group, i.e., $R^1$, can, independently, be —$CF_3$.

In any of the above embodiments, an R group can also, independently, be chosen from —$(CH_2)_{1-4}NH_2$, —$(CH_2)_{1-4}NHC(=N)NH_2$ and an amidino group. In any of the above embodiments, each R group, i.e., $R^2$, can, independently, be chosen from —$(CH_2)_{2-4}NH_2$ and —$(CH_2)_{1-4}NHC(=N)NH_2$. In any of the above embodiments, each R group, i.e., $R^2$, can, independently, be chosen from —$(CH_2)_{3-4}NH_2$ and —$(CH_2)_{3-4}NHC(=N)NH_2$. In any of the above embodiments, each R group, i.e., $R^2$, can, independently, be chosen from —$(CH_2)_4NH_2$ and —$(CH_2)_4NHC(=N)NH_2$. In any of the above embodiments, each R group, i.e., $R^2$, can be —$(CH_2)_4NHC(=N)NH_2$.

In some embodiments, each R group is independently, chosen from $C_1$-$C_3$alkyl, $C_1$-$C_3$alkoxy, halo, and halo$C_1$-$C_3$alkyl. In some embodiments, each R group is, independently, chosen from $C_1$-$C_2$alkyl, halo, and halo$C_1$-$C_2$alkyl. In some embodiments, each R group is, independently, chosen from halo and halo$C_1$-$C_2$alkyl.

In some embodiments, each R group is, independently, chosen from halo and halomethyl; —$(CH_2)_4NH_2$ and —$(CH_2)_4NHC(=N)NH_2$; a pyrrolidine, a pyrroline, an imidazolidine, an imidazoline, a pyrazolidine, a pyrazoline, a piperidine, a piperazine, and a morpholine.

In some embodiments, the composition further comprises an antimicrobial agent chosen from amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamnicin, sisomicin, spectinomycin, spiramycin, streptomnycin, tetracycline, thiamphenicol, thiostrepton, tobramycin, tunicamycin, tylosin, viomycin, virginiamycin, camptothecin, 10-deacetylbaccatin III, azacytidine, 7-aminoactinomycin D, 8-quinolinol, 9-dihydro-13-acetylbaccatin III, aclarubicin, actinomycin D, actinomycin 1, actinomycin V, bafilomycin A1, bleomycin, capreomycin, chromomycin, cinoxacin, ciprofloxacin, cis-diammineplatinum(II) dichloride, coumcermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, metronidazol, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprim, tubercidin, 5-azacytidine, cordycepin, formycin A, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymnethylpenicillinic acid, phosphomycin, pipemidic acid, piperacillin, ristomycin, vancomycin, 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, valinomycin, (+)-usnic acid, (±)-miconazole. (S)-(+)-camptothecin, 1-deoxymannojirimycin, 2-heptyl-4-hydroxyquinoline N-oxide, cordycepin, 1,10-phenanthroline, 6-diazo-5-oxo-L-norleucine, 8-quinolinol, antimycin, antipain, ascomycin, azasrine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfonamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, vineomycin A1, paracelsin, rifaximin, loracarbef, ertapenem, doripenem, imipenem, cilastatin, meropenem, cefadroxil, cefalotin, cefalothin, cephalexin, cefoxitin, cefprozil, cefuroxime, cefixime, cefdinir, cefditoren, cefpodoxime, ceftzidime, ceftibuten, ceftizoxime, cefepime, ceftaroline fosamil, ceftobiprole, teicoplanin, telavancin, daptomycin, clarithromycin, dirithromycin, roxithromycin, troleandomycin, telithromycin, aztreonam, linezolid, posizolid, radezolid, torezolid, flucloxacillin, mezlocillin, methicillin, penicillin V, temocillin, ticarcillin, clavulanate, sulbactam, tazobactam, enoxacin, gatifloxacin, levofloxacin, moxifloxacin, norfloxacin, trovafloxacin, grepafolxacin, sparfloxacin, temafloxacin, mafenide, sulfacetamide, silver sulfadiazine, sulfamethizole, sulfamethoxazole, sulfisoxazole, sulfonamidochrysoidine, clofazimine, dapsone, ethionamide, isoniazid, pyrazinamide, rifabutin, rifapentine, arsphenamine, fosfomycin, mupirocin, platensimycin, quinupristin, dalfopristin, tigecycline, ceftazidime, tinidazole, artemisinin, artesunate, quinine, sulfadoxine-pyrimethamine, hydroxychloroquine, amodiaquine, pyrimethamine, sulphadoxine, proguanil, mefloquine, atovaquone, primaquine, and halofantrine. In any of the above embodiments, the antimicrobial agent is chosen from gentamicin, imipenem, piperacillin, ceftazidime, aztreonam, ceftriaxone, ampicillin, ciprofloxacin, linezolid, daptomycin, and rifampicin.

In some embodiments, the antimicrobial agent chosen from anisomycin, apramycin, blasticidine S, brefeldin A, butirosin, chlortetracycline, clotrimazole, cycloheximide, demeclocycline, dibekacin, dihydrostreptomycin, duramycin, emetine, fusidic acid. G 418, helvolic acid, hygromycin B, josamycin, kanamycin, kirromycin, lincomycin, meclocycline, mepartricin, midecamycin, netilmicin, nitrofurantoin, nourseothricin, oleandomycin, paromomycin, puromycin, rapamycin, ribostamycin, rifampicin, rifamycin, rosamicin, sisomicin, spectinomycin, spiramycin, streptomycin, thiamphenicol, thiostrepton, tunicamycin, tylosin, viomycin, virginiamycin, camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, metronidazole, mithramycin A, mitomycin C, nalidixic acid, netropsin, nitrofurantoin, nogalamycin, nonactin, novobiocin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, tubercidin, 5-azacytidine, cordycepin, formycin A, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefotaxime, cefsulodin, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, vancomycin, 2-mercaptopyridine, 4-bromocalcimycin A23187, alamethicin, amphotericin B, calcimycin A23187, chlorhexidine, clotrimazole, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, DL-penicillamine, praziquantel, salinomycin, surfactin, valinomycin, (+)-usnic acid, (±)-miconazole, (S)-(+)-camptothecin, 1-deoxymannojirimycin, cordycepin, 2-heptyl-4-hydroxyquinoline N-oxide, 1,10-phenanthroline, 6-diazo-5-oxo-L-norleucine, 8-quinolinol, antimycin, antipain, ascomycin, azaserine, bafilomycin, cerulenin, chloroquine, cinoxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, nalidixic acid, N-(6-aminohexyl)-5-chloro-1-naphthalenesulfonamide, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, vineomycin A1, paracelsin, rifaximin, loracarbef, ertapenem, doripenem, imipenem, cilastatin, meropenem, cefadroxil, cefalotin, cefalothin, cephalexin, cefoxitin, cefprozil, cefuroxime, cefdinir, cefditoren, cefpodoxime, ceftzidime, ceftibuten, cefepime, ceftaroline fosamil, ceftobiprole, teicoplanin, telavancin, daptomycin, clarithromycin, dirithromycin, roxithromycin, troleandomycin, telithromycin, aztreonam, linezolid, posizolid, radezolid, torezolid, flucloxacillin, mezlocillin, methicillin, penicillin V, temocillin, ticarcillin, clavulanate, sulbactam, tazobactam, enoxacin, gatifloxacin, levofloxacin, moxifloxacin, trovafloxacin, grepafloxacin, sparfloxacin, temafloxacin, sulfamethizole, sulfamethoxazole, sulfonamidochrysoidine, clofazimine, dapsone, ethionamide, isoniazid, pyrazinamide, rifabutin, rifapentine, arsphenamine, fosfomycin, mupirocin, platensimycin, quinupristin, dalfopristin, tigecycline, tinidazole, artemisinin, artesunate, quinine, sulfadoxine-pyrimethamine, hydroxychloroquine, amodiaquine, sulphadoxine, proguanil, mefloquine, atovaquone, primaquine, and halofantrine.

In some embodiments, the antimicrobial agent is chosen from imipenem, piperacillin, aztreonam, ampicillin, linezolid, daptomycin, and rifampicin.

The amount of the antimicrobial agent can determined based upon known dosage amounts. In some embodiments, the pharmaceutical composition comprises a therapeutically effective amount of the antimicrobial agent. In some embodiments, the amount of antimicrobial agent in the pharmaceutical composition with the arylamide compound can be reduced by about 10%, by about 20%, by about 30%, by about 40%, by about 50%, by about 60%, by about 70%, by about 80%, or by about 90% compared to administration of the antimicrobial agent by itself.

In some embodiments, the disclosure relates to any one or more compositions disclosed herein further comprising a pharmaceutically acceptable carrier. Pharmaceutically acceptable carriers are chosen from starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. When administered to a human, the compounds can be sterile. Water is a suitable carrier when the compound of Formula 100, 110, or mixtures of both compounds having Formulas 100 and 110, each of the formulas optionally comprising one or two substituent R groups comprising any of the small chemicals disclosed herein. Saline solutions and aqueous dextrose and glycerol solutions can also be employed as liquid carriers, particularly for topical solutions. The present compositions, if desired, can also contain minor amounts of wetting or emulsifying agents, or pH buffering agents. Examples of suitable pharmaceutical carriers are described in Remington's Pharmaceutical Sciences, A. R. Gennaro (Editor) Mack Publishing Co.

The compositions described herein can take the form of a solution, suspension, emulsion, tablet, coating of a tablet comprising another active agent, pill, pellet, capsule, capsule containing a liquid, powder, sustained-release formulation, suppository, aerosol, spray, or any other form suitable for topical use. In some embodiments, the compositions disclosed here comprise a gel formulation having one or a plurality of excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone. Topical formulations including 3-methanesulfonylpropionitrile can be in a form of gel, cream, lotion, liquid, emulsion, ointment, spray, solution, suspension, and patches. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In some embodiments, the disclosure provides a composition comprising: a clay powder or pharmaceutically acceptable salt thereof. In some embodiments the disclosure provides a composition comprising a Lutrol® coblock polymer or pharmaceutically acceptable salt thereof; and, optionally, at least one aqueous suspending agent. In some embodiments, the disclosure provides a composition comprising: a clay powder or pharmaceutically acceptable salt thereof; and a Lutrol® coblock polymer or pharmaceutically acceptable salt thereof. In some embodiments, the disclosure provides a composition comprising Fuller's Earth. In some embodiments, the disclosure provides a composition comprising a silicate. In some embodiments, the disclosure provides a composition comprising bentonite. In some embodiments the disclosure provides a composition free of a Lutrol® coblock polymer, free of clay, free of any one or combination of reagents or components disclosed herein.

In some embodiments, the composition or combination of compositions disclosed herein comprise one or a plurality of "cosmetically effective active agents," that is that an active agents used for the cosmetic care of the skin, such as moisturizing, cleaning, deep cleansing, tightening, toning, skin lightening, protective (in particular protective against ultraviolet radiation or other aggressive factors, such as the cold and atmospheric pollution), antiaging (in particular antiwrinkle and/or firming) and slimming cares. The disclosure relates to any methods described in the foregoing sentence comprising applying to contacting any of the compositions or combinations of compositions with the skin of a subject in need of moisturizing, cleaning, deep cleansing, toning, tightening, UV protection, antiaging or slimming.

The definition of "cosmetic additive" relates, in the context of the present disclosure, to any ingredient used in cosmetic composition formulations for the purpose of conferring specific physical, chemical or sensorial properties thereon or to guarantee their stability, such as an antioxidant, a coloring agent, a fragrancing agent, a texturing agent or a preservative.

In one embodiment, lauryl lactate (for example, at from about 0.1 to about 10%, or from about 0.2 to about 5%, or from about 0.5 to about 5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the composition or combination of compositions. In some embodiments, the compositions or combination of compositions comprise lauryl lactate with about 90% or about 95% purity; the high purity mitigates the presence of hydrolytic and oxidative agents. In addition, ethanol at from about 0.1 to about 20%, or from about 0.5 to about 10% (w/w) in the formulation provides suitable solubility for a gel formulation. In some embodiments, the formulation can contain about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 or about 20% ethanol. These values can be used to define a range, such as from 1 to about 10%. In another embodiment, diethylene glycol monoethylether is included in the topical gel formulation.

In some embodiments, the pharmaceutical composition or combination of compositions further comprise a cyclodextrin. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkyleyelodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Applications of cyclodextrins have been reviewed in Rajewski et al., *Journal of Pharmaceutical Sciences*, 1996, 85, 1155-1159. An acceptable cyclodextrin can optionally be present in a composition at a concentration from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 to about 200 mg/ml. These values can be used to form a range, such as from about 5 to about 100 mg/ml, or from about 10 to about 50 mg/ml, or from about 1% to about 50% w/v, from about 5% to about 40% w/v, from about 10% to about 30% w/v, from about 15% to about 25% w/v, or about 20% w/v of the composition. In some embodiments, the pharmaceutical composition can further comprise 20% w/v Kleptose.

The present disclosure also provides pharmaceutical compositions comprising a compound having the formula 100 or 110 or combinations of compounds having Formula 100 and/or Formula 110 or a pharmaceutically acceptable salt thereof; a pharmaceutically acceptable carrier; and, optionally, an antimicrobial agent chosen from any of the disclosed antibiotic compounds disclosed herein.

The present disclosure also provides pharmaceutical compositions comprising polyamides and/or polyesters. Polyamides and polyesters that are useful for the present disclosure can be prepared by typical condensation polymerization and addition polymerization processes (see, for example, G. Odian, Principles of Polymerization, John Wiley & Sons, Third Edition (1991), and M. Steven, Polymer Chemistry, Oxford University Press (1999)). Most commonly, the polyamides are prepared by a) thermal dehydration of amine salts of carboxylic acids, b) reaction of acid chlorides with amines, and c) aminolysis of esters. Methods a) and c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and has been used extensively for the synthesis of aromatic polyamides.

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present disclosure. An alternative embodiment of the present disclosure is the corresponding polysulfonamides that can be prepared in analogous fashion by substituting sulfonyl chlorides for carboxylic acid chlorides.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair®), or rinses (e.g., Caphosol®).

In some embodiments, the compounds described herein can be delivered in a vesicle, in particular a liposome (see, Langer. Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, ethanol and glycerin.

When administered to a mammal (e.g., to an animal for veterinary use or to a human for clinical use) the compounds can be administered in isolated form or with any of the pharmaceutically acceptable carrier, diluent or excipient disclosed herein.

In one embodiment, the compounds are formulated in accordance with routine procedures as a pharmaceutical composition adapted for administration to humans. Typically, compounds are solutions in a sterile, isotonic, aqueous suspending agent. Where necessary, the compositions can also include a solubilizing agent. The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or canisters. The unit dosage form can also be a capsule, cachet, or tablet itself, or it can be the appropriate number of any of these packaged forms.

In some embodiments, a composition of the present disclosure is in the form of a liquid, gel or semi-solid phase wherein the active agent is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In yet other embodiments, the pharmaceutical composition can be in contact with a solid article. For example, in some embodiments, the composition is a solid article that can be inserted onto a suitable location on the body, The compositions are preferably sterile and have physical properties (e.g., osmolality and pH) that are specially suited for application to the skin, including tissues that have been compromised as the result of preexisting disease, trauma, surgery or other physical conditions. For example, aqueous compositions of the disclosure typically have a pH in the range of from about 4.5 to about 8.0, from about 6.0 to about 8.0, from about 6.5 to about 8.0, or from about 7.0 to about 8.0.

In some embodiments, the compositions disclosed herein comprise one or a combination of acceptable excipients. Acceptable excipients include, but are not limited to, viscosity-enhancing agents, preservatives, stabilizers, antioxidants, suspending agents, solubilizing agents, buffering agents, lubricating agents, ophthalmically or optically acceptable salts, and combinations thereof. Examples of suitable viscosity-enhancing agents include, but are not limited to, glycerin, polyvinyl alcohol, polyvinyl pyrrolidone, methylcellulose, hydroxypropylmethylcellulose, hydroxyethyl-cellulose, carboxymethylcellulose, hydroxypropylcellulose, and/or various gelling agents. For example, in some embodiments, the viscosity-enhancing agent is chosen from methylcellulose, hydroxypropyl-methylcellulose, polyvinyl alcohol, and glycerol. Such agents are generally employed in the compositions of the disclosure at a concentration from about 0.01% to about 3% by weight.

In some embodiments, the composition comprises one or a combination of polymers, chosen from, for example, hydroxypropylmethylcellulose, carbomer (acrylic acid polymer), poly(methylmethacrylate), polyacrylamide, polycarbophil, polyethylene oxide, acrylic acid/butyl acrylate copolymer, sodium alginate, and dextran.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Several preservatives may precipitate in the presence of other excipients in the composition and/or in the presence of the polymers and oligomers in the compositions. For example, benzalkonium chloride can precipitate in a composition using iota-carrageenan as a gelling agent. Thus, in those embodiments of the disclosure in which a preservative is present, the preservative is one that does not precipitate but remains in solution in the composition.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount from about 0.01% to about 0.5%. In those embodiments containing a preservative other than EDTA, the EDTA or a salt thereof, more particularly disodium EDTA, can be present in an amount from about 0.025% to about 0.1% by weight.

One or more antioxidants can also be included in the compositions. In some embodiments, the antioxidants are a component of the composition used for a cosmetic application and for prevention of contamination by a contaminant. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the composition comprises acceptable nonionic surfactants, for example polysorbate 80, can be useful as solubilizing agents, as can acceptable glycols, polyglycols, e.g., polyethylene glycol 400 (PEG-400), and glycol ethers.

In some embodiments, the composition optionally contains a suspending agent. For example, in those embodiments in which the composition is an aqueous suspension or solution/suspension, In some embodiments, the composition comprises an aqueous solvent or suspension agent that is water, ethanol, or a combination of water and ethanol. The composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68. F84 and P-103); cyclodextrin; or other agents known to those of skill in the art. Typically, such co-solvents or surfactants are employed in the compositions at a level of from about 0.01% to about 2% by weight.

The compositions described herein can also be incorporated into compositions such as, for example, polishes, paints, sprays, or detergents formulated for application to a surface to decontaminate the surface thereon. These surfaces include, but are not limited to, countertops, desks, chairs, laboratory benches, tables, floors, bed stands, tools, equipment, doorknobs, windows, and the like. The compositions described herein can also be incorporated into soaps and hand lotions. The present compositions, including the cleansers, polishes, paints, sprays, soaps, and detergents, can contain one or more of the compositions described herein. In addition, the compositions can optionally contain one or more of each of the following: solvents, carriers, thickeners, pigments, fragrances, deodorizers, emulsifiers, surfactants, wetting agents, waxes, and/or oils. For example, in some embodiments, the compositions can be incorporated into a formulation for external use as a pharmaceutically acceptable skin cleanser, particularly for the surfaces of human hands. Cleansers, polishes, paints, sprays, soaps, hand lotions, and detergents and the like containing the compositions described herein can be useful in homes and institutions, particularly but not exclusively, in hospital settings for the prevention of nosocomial infections.

The present disclosure also provides pharmaceutical packs or kits comprising one or more containers filled with one or more compounds described herein and/or one or more composition disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one composition described herein. In some embodiments, the kit comprises a compound described herein in a single injectable dosage form, such as a single dose within an injectable device such as a syringe with a needle.

The present disclosure also provides methods of decontaminating the skin of a subject having a microbial infection comprising administering to the subject in need thereof an effective amount of a composition comprising Formula 100, Formula 110 or a mixture of Formula 100 and 110, or pharmaceutically acceptable salts thereof.

In some embodiments, the composition can include a mixture of a compound having formula:

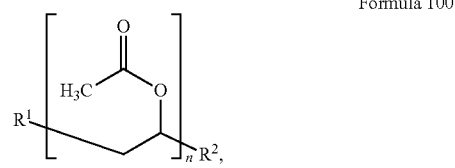

Formula 100 or pharmaceutically acceptable salt thereof, and a compound having formula:

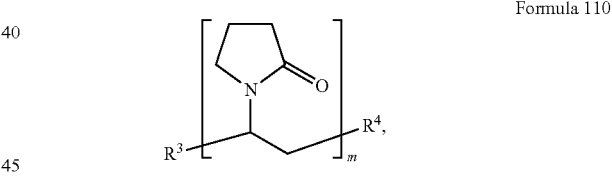

Formula 110 or pharmaceutically acceptable salt thereof. The average molecular weight of formula 100 can be about 100 K Daltons, 200, 300, 350, 400, 425, 450, 475, 500, 550, 600, 700, 800 or about 900 K Daltons. These values can define a range, such as from about 400 K Daltons to about 550 K Daltons. The average molecular weight of formula 110 can be about 10 K Daltons, 20, 30, 35, 40, 43, 45, 47, 50, 53, 55, 57, 60, 65, 70, 80 or about 90 K Daltons. These values can define a range, such as from about 45 K Daltons to about 55 K Daltons. The molecular weight values and ranges for each of Formula 100 and 110 can be combined within the mixture, such as a combination of Formula 100 at 450 K Dalton and Formula 110 at 50 K Daltons.

In some embodiments, the composition comprises a compound of Formula 100 or Formula 10 or any compound disclosed herein and the antimicrobial agent disclosed herein.

The present disclosure also provides any one or more of the foregoing compositions for treating a microbial infection in a mammal, or killing or inhibiting the growth of a microbe.

The present disclosure also provides any one or more of the foregoing compositions for use in the manufacture of a medicament for treating or preventing contamination in a mammal, or killing or inhibiting the growth of a microbe.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for topical administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, the composition comprises Kollidon® SR in about 1, 2, 3, 4, 5, 6, 7, 8, 9, 10, 11, 12, 13, 14, 15, 16, 17, 18, 19, 20, 21, 22, 23, 24 or about 25 wt % (weight percent). These values can be used to define a range, such as from about 5 to about 20%.

In some embodiments, the composition comprises Lutrol® F127 in about 1, 2, 3, 4, 5, 6, 7, 8, 9 or about 10 wt %. These values can be used to define a range, such as from about 1 to about 7%.

In some embodiments, the composition comprises carboxymethyl cellulose in about 1, 2, 3, 4, 5, 6, 7, 8, 9 or about 10 wt %. These values can be used to define a range, such as from about 1 to about 7%.

In some embodiments, the composition comprises Fuller's earth in about 5, 6, 7, 8, 9, 10, 11, 12, 13, 14, 15, 16, 17, 18, 19, 20, 21, 22, 23, 24, 25, 26, 27, 28, 29 or about 30 wt %. These values can be used to define a range, such as from about 10 to about 25%.

In some embodiments, the composition comprises bentonite in about 1, 2, 3, 4, 5, 6, 7, 8, 9, 10, 11, 12, 13, 14 or about 15 wt %. These values can be used to define a range, such as from about 1 to about 10%.

In some embodiments, the composition comprises ethanol in about 5, 10, 15, 20, 25, 30, 35, 40, 45, 50, 55 or about 60 wt %. These values can be used to define a range, such as from about 20 to about 50%.

In some embodiments, the composition comprises water in about 5, 10, 15, 20, 25, 30, 35, 40, 45, 50, 55, 60, 65 or about 70 wt %. These values can be used to define a range, such as from about 10 to about 60%.

In some embodiments, the composition comprises the formulation as listed in Table 1 or pharmaceutically acceptable salts of such components:

TABLE 1

| Component | Percentage |
| --- | --- |
| Kollidon ® SR | 5 to 20% |
| Lutrol ® F127 | 1 to 5% |
| Carboxymethyl cellulose | 1 to 5% |
| Fuller's earth | 10 to 25% |
| Bentonite | 1 to 10% |
| Ethanol | 20 to 50% |
| Water | 10 to 60% |

In some embodiments, the composition comprises the formulation as listed in Table 2 or pharmaceutically acceptable salts of such components:

TABLE 2

| Component | Percentage |
| --- | --- |
| Kollidon ® SR | 15, 16, 17, or 18% |
| Lutrol ® F127 | 3, 4, 5, or 6% |
| Carboxymethyl cellulose | 1, 2, 3, or 4% |
| Fuller's earth | 10, 11, 12, 13, or 14% |
| Bentonite | 1, 2, 3, 4, or 5% |
| Ethanol | 42, 43, 44, 45 or 46% |
| Water | 10, 11, 12, 13, or 14% |

In some embodiments, the composition comprises PVA in about 1, 2, 3, 4, 5, 6, 7, 8, 9, 10, 11, 12, 13, 14, 15, 16, 17, 18, 19, 20, 21, 22, 23, 24 or about 25 wt %. These values can be used to define a range, such as from about 5 to about 15%.

In some embodiments, the composition comprises polyethylene glycol, e.g., PEG 2000, in about 1, 2, 3, 4, 5, 6, 7, 8, 9, 10, 11, 12, 13, 14, 15, 16, 17, 18, 19 or about 20 wt %. These values can be used to define a range, such as from about 5 to about 15%.

In some embodiments, the composition comprises the formulation as listed in Table 3 or pharmaceutically acceptable salts of such components:

TABLE 3

| Component | Percentage |
| --- | --- |
| Kollidon ® SR | 10% |
| Polyvinyl alcohol | 10% |
| Carboxymethyl cellulose | 1% |
| Fuller's earth | 10% |
| Bentonite | 5% |
| Polyethylene glycol 2000 | 5% |
| Water | 59% |

In some embodiments, the composition comprises glycerol in about 10, 15, 20, 25, 30, 35, 40, 45, 50, 55 or about 60 wt %. These values can be used to define a range, such as from about 30 to about 50%.

In some embodiments, the composition comprises the formulation as listed in Table 4 or pharmaceutically acceptable salts of such components:

TABLE 4

| Component | Percentage |
| --- | --- |
| Kollidon ® SR | 15% |
| Polyvinyl alcohol | 10% |
| Carboxymethyl cellulose | 1% |
| Fuller's earth | 14% |
| Bentonite | 10% |
| Polyethylene glycol 2000 | 10% |
| Glycerol | 40% |

In some embodiments, the composition comprises the formulation as listed in Table 5 or pharmaceutically acceptable salts of such components:

TABLE 5

| Component | Amount |
| --- | --- |
| Kollidon ® SR | 3 g |
| Lutrol ® F127 | 1 g |
| Carboxymethyl cellulose | 0.3 g |
| Fuller's earth | 2.5 g |
| Bentonite | 0.5 g |
| Ethanol | 8 mL |
| Water | 2 mL |

The compositions of the present disclosure can also contain one or more different types of nanoparticles. The nanoparticles can include metal nanoparticles (including, gold, silver, and platinum), organic or carbon based nanoparticles, or combinations thereof. The nanoparticles can include metal oxides including titanium dioxide, zinc oxide, zirconium dioxide, black, yellow, red and brown iron oxides, cerium dioxide, cerium oxide, alumina, titanates ($BaTiO_3$, $SrTiO_3$), indium oxide, tin oxide, antimony oxide, magnesium oxide (MgO), calcium oxide (CaO), manganese oxides, molybdenum oxide, silica, yttrium oxide and mixtures thereof.

The nanoparticle can have a uniform size distribution. They can have a particle size, or average particle size of about, less than about or more than about 10, 20, 30, 40, 50, 60, 70, 80, 90, 100, 150, 200, 250, 300, 350, 400, 450, 500, 550, 600, 650, 700, 750, 800, 850, 900, 950 or about 1000 nm. These values can be used to define a range, such as from about 10 to about 50 nm, or from about 10 to about 250 nm, or from about 50 to about 200 nm. In some embodiments the size of the nanoparticles should be small enough to absorb the contaminants efficiently but not small enough to deeply penetrate into the skin. The nanoparticles can be sized to remain on the face of the skin or penetrate into the top layer(s) of the skin. In some embodiments, composition excludes nanoparticles, or a sufficient amount of nanoparticles, having a particle size less than about 0.1, 0.5, 1, 5 or about 10 nm that can lead to adverse effects or reduced decontamination due to deep penetration into the skin.

The term porosity is used to denote the ratio of the volume of all the pores (e.g. hollow spaces) in the nanoparticle to the volume of the whole thereof. Accordingly, the ratio of the open hollow spaces is specified in percent (%) with respect to the external volume, which would correspond to 100%. In some embodiments, the porosity of the nanoparticle can be about, less than about or more than about 1, 2, 5, 10, 15, 20, 25, 30, 35, 40, 45, 50, 55, 60, 65, 70, 75, 80, 85 or about 90%. These values can be used to define a range, such as from about 10% to about 50%.

Methods

The disclosure relates to methods of making any one or combination of compositions disclosed herein, wherein recitation of one particular compound optionally includes recitation of the compound's pharmaceutically acceptable salt. If a particular component of any such composition is itself a mixture, recitation of that component also optionally includes pharmaceutically acceptable salts of the individual components of the mixture. For instance, if the composition comprises Kollidon® SR, the composition comprises a mixture of polyvinyl acetate and povidone or, optionally, a mixture of any pharmaceutically acceptable salt of polyvinyl acetate and/or any pharmaceutically acceptable salt of povidone.

In some embodiments, the disclosure relates to a method of manufacturing one or a combination of compositions disclosed herein. In some embodiments, the method of making comprises adding one or any combination of the components in a vessel serially or contemporaneous with any one or combination of other components and, subsequently, mixing the components with a mixing element. In some embodiments, individual compounds of Tables 1, 2, 3, 4, or 5 in powder or other solid phase are added to a vessel individually, sequentially, or in combination (contemporaneously) and then one or a combination of volumes of aqueous suspending agents (such as ethanol, glycerol and/or water) are added to the mixture of solid compounds. In some embodiments, after the one or a combination of volumes of aqueous suspending agents are added to the mixture of solid compounds. the entire mixture is stirred by a mixing element. Aliquots of gel or paste or semisolid composition can then, optionally, be placed in the containers suitable for commercial sale or transfer. In some embodiments, the composition disclosed herein comprises as second active agent such as an antibiotic that is packaged together but not mixed into the solution. In other embodiments, the second active agent is mixed with the other components of the compositions disclosed herein.

The disclosure also relates to a method of decontaminating a surface or skin of a subject in need thereof, the method comprising contacting any one or combination of compositions disclosed herein with the surface or at a location on the skin of the subject that is or has been exposed to a contaminant or proximate to the location on the skin that is or has been exposed to a contaminant. In some embodiments, the method of decontaminating a surface or skin of a subject in need thereof comprises contacting any one or combination of compositions disclosed herein with the surface or at a location on the skin of the subject that is or has been exposed to a contaminant or proximate to the location on the skin that is or has been exposed to a contaminant after the surface or skin of the subject has been exposed to a contaminant for more than about 5, about 10, about 15, about 20, about 25, or about 30, about 40, or about 50 minutes. In some embodiments, the method of decontaminating a surface or skin of a subject in need thereof comprises contacting any one or combination of compositions disclosed herein with at a location or proximate to the location where the surface or skin was exposed to the contaminant. In some embodiments, the method comprises contacting the surface or the skin of the subject that is or has been exposed to a contaminant more than about 5, about 10, about 15, about 24, about 48, or about 72 hours after exposure to the contaminant. In some embodiments, the method of decontaminating a surface or skin of a subject in need thereof comprises allowing the composition or combination of compositions disclosed herein to rest at or proximate to the site of contamination for no less than about 1, about 2, about 3, about 4, about 5, about 6, about 7, about 8, about 9, or about 10 minutes. In some embodiments, the method of decontaminating a surface or skin of a subject in need thereof comprises allowing the composition or combination of compositions disclosed herein to rest at or proximate to the site of contamination for no less than about 10, about 20, about 30, about 40 or about 50 minutes. In some embodiments, the method of decontaminating a surface or skin of a subject in need thereof comprises allowing the composition or combination of compositions disclosed herein to rest at or proximate to the site of contamination for no less than about 10, about 20, about 30, about 40 or about 50 minutes before removing the composition by washing the composition or combination of compositions off of the surface or skin. In some embodiments, the method of decontaminating a surface or skin of a subject in need thereof comprises allowing the composition or combination of compositions herein to rest at or proximate to the site of contamination for an amount of time sufficient for the composition or combination of compositions to solidify if the composition or combination of compositions is in a formulation that is not solid phase. In some embodiments, the method further comprises peeling the composition or combination of compositions off of the surface or the skin after allowing the composition or combination of compositions in a formulation other than a solid formulation disclosed herein to rest at or proximate to the site of contamination for an a mount of time sufficient for the composition or combination of composition to solidify or thicken. In some embodiments, the formulation other than a solid formulation is a gel, paste or other semisolid formulation which, when exposed to air for a time sufficient to harden, will solidify or thicken. In some embodiments, the method of decontaminating a surface or skin of a subject in need thereof comprises allowing the composition or combination of compositions in a gel formulation disclosed herein to rest at or proximate to the site of contamination for an amount of time sufficient for the composition or combination of compositions to solidify and/or absorb the contaminant from the surface or skin. In some embodiments, any of the methods herein further comprise peeling or removing the composition or combination of compositions from the surface or the skin after allowing the composition or combination of compositions to rest at or proximate to the site of contamination for an amount of time sufficient for the composition or combination of composition to at least partially absorb an amount of the contaminant.

In some embodiments, the disclosure relates to the use of any of the compositions disclosed herein, either individually or in combination, for treating subjects who have been exposed to a toxin, such as a nerve agent, gas or other poison.

In some embodiments, the disclosure relates to the use of any of the compositions disclosed herein, either individually or in combination, for treating subjects who have been exposed to radiation. In other embodiments, the application relates to the use of any of the compositions disclosed herein, either individually or in combination, for preventing subjects exposed to radiation from acquiring with acute radiation syndrome comprising contacting a site of radiation exposure with a therapeutically effective dose of one or the combination of pharmaceutical compositions. The application also relates to compositions comprising any of the compounds disclosed herein, either individually or in combination, for and methods of using the compositions to treat subjects who have been exposed to radiation syndrome comprising contacting a site of radiation exposure with a therapeutically effective dose of one or the combination of any of the compounds disclosed herein. In other embodiments, the application relates to the use of any of the compositions disclosed herein, either individually or in combination, for preventing subjects exposed to radiation from acquiring with acute radiation syndrome comprising contacting a site of radiation exposure with a therapeutically effective dose of one or plurality of pharmaceutical compositions disclosed herein for a time sufficient to cause absorption of contaminant into the one or plurality of pharmaceutical compositions. The application also relates to compositions comprising any of the compounds disclosed herein, either individually or in combination, for treatment of subjects who have been exposed to radiation comprising contacting a site of radiation exposure with a therapeutically effective dose of one or a combination of any of the compounds disclosed herein with a therapeutically effective dose for a time sufficient to cause absorption of contaminant into the one or plurality of pharmaceutical compositions. In some embodiments, the method comprises contacting skin of the subject in need thereof with the one or plurality of compositions or compounds for a time sufficient to absorb radioactive material from the skin and at a therapeutically effective dosage so that the subject is less likely to suffer from acute radiation syndrome. In some embodiments, the step of contacting is performed more than about 5, about 10, about 15, about 24, about 48, or about 72 hours after exposure to the radiation. In some embodiments, the method of preventing the subject from acquiring ARS comprises allowing the composition or combination of compositions disclosed herein to rest at or proximate to a site of radioactivity contamination on or within the subject for no less than about 1, about 2, about 3, about 4, about 5, about 6, about 7, about 8, about 9, or about 10 minutes. In some embodiments, the method of preventing the subject from acquiring ARS comprises allowing the composition or combination of compositions disclosed herein to rest at or proximate to the site of contamination for no less than about 10, about 20, about 30, about 40 or about 50 minutes. In some embodiments, the method of preventing the subject from acquiring ARS comprises allowing the composition or combination of compositions disclosed herein to rest at or proximate to the site of contamination for no less than about 10, about 20, about 30, about 40 or about 50 minutes before removing the composition by washing the composition or combination of compositions off of the site of contamination. In some embodiments, the method of preventing the subject from acquiring ARS comprises contacting a location at or proximate to a site on the skin of the subject exposed to radiation with a therapeutically effective dose of one or a plurality of compositions and/or compounds disclosed herein and for a time period sufficient to allow absorption of radioactive material from the skin into the one or a plurality of compositions and/or compounds disclosed herein. in some embodiments, the step of contacting the skin is performed after the skin has been exposed to radiation for about 10, 15, 20, 24, 36, 48, or 72 hours.

The methods of the disclosure comprise treating a subject who has been exposed to at least 0.25, 0.5, 1, 2, 3, 4, 5, 6, 7, 8, 9 or 10 Gray of partial- or whole-body radiation. In other embodiments, the methods comprise treating a subject who has been exposed to at least 0.25, 0.5, 1, 2, 3, 4, 5, 6, 7, 8, 9 or 10 Gray of whole-body radiation. In some embodiments, the subject is a patient being treatment for cancer.

In some embodiments, the subject has been exposed to at least 0.25, 0.5, 1, 2, 3, 4, 5, 6, 7, 8, 9 or 10 Gray of radiation over a time frame of less than 1 minute, or up to about 5 minutes, about 10 minutes, about 30 minutes, about 60 minutes, about 1 hour, about 6 hours, about 12 hours, about 24 hours, about two days, about one week, or about two weeks. In other embodiments, the subject has been exposed to at least about 0.25, about 0.5, about 1, about 2, about 3, about 4, about 5, about 6, about 7, about 8, about 9 or about 10 Gray of radiation over a time frame of more than 24 hours.

In an embodiment, the treatment is administered or used once a day. In another embodiment, the treatment is administered or used twice a day. In still another embodiment, the treatment is administered or used three times a day or four times a day. In a further embodiment, the treatment is administered or used at least once a day for one, two, three, four, five, six or seven days. In still a further embodiment, the treatment is administered at least once a day for a longer term such as about 1, 2, 3, 4, 5, 6, 7, 8, 9, 10, 11 or 12 weeks. In an even further embodiment, the treatment is administered or used at least once a day until the condition has ameliorated to where further treatment is not necessary. The treatment period may also comprise cycles, for example, administration or use once daily for about three to seven days, followed by a period of rest for about 5 to 20 days, to constitute one cycle of treatment. In an embodiment, patients are treated with more than one cycle, for example, at least two, three, four or five cycles, In a further embodiment, the effective dosage of the agent used for the treatment or prophylaxis increases or decreases over the course of a particular treatment or prophylaxis regime. In an embodiment, the effective dosage of the agent decreases over the course of a particular treatment regimen. In some instances, chronic administration is required. For example, the compositions are administered to the subject, or used, in an amount and for a duration sufficient to treat the subject. The disclosure also relates to methods of decreasing the likelihood that a subject exposed to radiation acquire ARS comprising contacting or administering any one or combination of compositions or compounds disclosed herein to a subject exposed to radiation at a therapeutically effective dose. The disclosure also relates to methods of decreasing the likelihood that a subject exposed to radiation acquire ARS comprising contacting or administering any one or combination of compositions or compounds disclosed herein to a subject exposed to radiation at a therapeutically effective dose and for a time period sufficient to absorb an amount radioactive material from the subject. In some embodiments, the step of administrating is performed by topical application and removal from the skin.

The disclosure relates to any of the disclosed methods herein further comprising the step of applying another agent to the skin in addition to the one or combination or plurality of compositions and/or compounds disclosed herein before, after, or contemporaneously with the one or combination or plurality of compositions and/or compounds disclosed herein. For instance, in some embodiments, the method involves administration of at least one agent other than the composition or combination of compositions disclosed herein that treats or prevents infection of intracellular damages of the subject caused by exposure of a toxin, such as radiation. In some embodiments, the method disclosed herein comprise the step of administrating one or a combination of: hydroxytryptamine, amifostine, any of the antibiotics listed herein, potassium iodide, chlorate, Reactive Skin Decontamination Lotion (RSDL), and soap. in some embodiments any one or more steps of contacting or administering to a subject any of the agents, compounds, compositions or combinations of such agents, compounds or compositions is performed by topical administration.

The disclosure relates to methods comprising increasing the decontamination efficiency of a topical formulation by mixing the topical formulation with an amount of any of the compositions or combination of compositions disclosed herein with one or more active agents used for decontamination of a surface of an inanimate object or skin of a subject. One of skill in the art will recognize that the compounds can be tested for decontamination activity by methods well known to those of skill in the art. Any compound found to be active can be purified to homogeneity and re-tested to obtain an accurate $IC_{50}$.

Kits

The present disclosure relates to kits comprising one or a plurality of containers, wherein at least one container comprises one or a combination of compositions and/or compounds disclosed herein. In some embodiments, the kit comprises an application or mixing element. In some embodiments, the mixing or application element is a stick, wooden or plastic applicator, tongue depressor, sponge, fabric, and/or pad or the like. The kit can also come with instructions describing how to mix, apply and dispose of the compositions and/or compounds.

The kits, the one or a plurality of containers, or combinations thereof can be hermetically sealed. In one embodiment, the dry components are stored in a separate container, or separate containers and the wet components, e.g., water, ethanol, water/ethanol mixture, are stored in a separate or separate containers.

In order that the present disclosure be more efficiently understood, examples are provided below. It should be understood that these examples are for illustrative purposes only and are not to be construed as limiting the disclosure in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted. All publications, patents or patent applications listed in this application are incorporated by reference in their entireties.

EXAMPLES

Example 1

Chemicals contaminated on skin surface can absorbed into stratum corneum (SC) within seconds to minutes of exposure and remain there to form a "chemical reservoir". The quantity of "chemical reservoir" positively correlates to systemic absorption in human and/or animal in vivo and skin penetration in vitro. Also, the SC reservoir function is probably the major factor in causing the "water wash-in" skin penetration enhancement effect when using water-based skin decontamination methods.

DDG, designed based on skin absorption/penetration mechanisms, exacts chemicals from skin reservoir. To evaluate skin decontamination efficiency of DDG, and compare it with currently-available commercial products, such as soap-water washing, Fuller's Earth and RSDL, dermatopharmacokinetic studies on human skin models in vitro and protection studies on mice model in vivo were conducted on model chemicals with various chemical-physical properties. Paraoxon was used as simulate of chemical warfare nerve agents, VX and sarin, due to its similarity of chemical-physical properties. It is an organophosphate oxon acting as acetylcholinesterase (AchE) inhibitor, therefore the decontamination efficiency of paraoxon can also be determined by AchE inhibition activity of receptor fluid in vitro and lethality of model animals in vivo.

In delayed decontamination study, treatments were applied up to several hours post chemical exposure. The decontamination systems showing greater decontamination efficiency at long exposure time provides more effective protection and greater opportunity for other interventions. SC reservoir measured by tape-stripping demonstrates the abilities of decontamination systems on removing chemical retained in SC. Hair follicles contributes significantly to human skin penetration. 24-hour hairy skin absorption/penetration study was conducted to evaluate the decontamination capacities of different systems under the influence of hair follicles.

Materials and Methods

Chemicals

Radiochemical purities of all carbon-14 labeled chemicals assayed were >95%. [7-14C]-salicylic acid (56 mCi/mmol) and [7-14C]-paraoxon (55 mCi/mmol) were synthesized by American Radiolabeled Chemicals, Inc. (St. Louis, Mo.). [14C]-terbinafine HCl (59 mCi/mmol) from Amersham plc (Amersham, UK). Corresponding non-radio labeled chemicals and trypsin 1:250 for epidermis digestion were obtained from Sigma-Aldrich (St Louis, Mo.).

Reagent grade ethanol, hexane, chloroform and sodium bicarbonate were obtained from Fisher Scientific (Pittsburgh, Pa.). ULTIMA GOLD™ scintillation cocktails were manufactured by PerkinElmer Life and Analytical Sciences (Boston, Mass.). Phosphate buffered saline (PBS) tablets from Diagnostic BioSystems (Pleasanton, Calif.). Soluene-350f tissue solubilizer and ULTIMA GOLD™ scintillation cocktails from PerkinElmer Life and Analytical Sciences (Boston, Mass.). ULTIMA GOLD™ scintillation cocktails were manufactured by PerkinElmer Life and Analytical Sciences (Boston, Mass.).

For dermatopharmacokinetic studies (delayed decontamination, SC reservoir, and 24 hours hairy skin absorption/penetration), dosing solution of each chemical was prepared in ethanol with specific radioactivity of 0.05 mCi/mL. 20 mg/mL corresponding non-radio labeled chemical was added to ascertain chemical binding amounts and rates were independent of solute concentration. 0.01 mole/L PBS aqueous solution containing 5% (v/v) polyethylene glycol was used as receptor fluid for skin absorption/penetration experiment.

For AchE inhibition activity in vitro and skin decontamination in vivo studies, 5% (v/v) non-radiolabeled paraoxon solution was prepared in ethanol. Acetylcholinesterase (AchE) from Electrophorus electricus (Type VI-S, lyophilized powder, 200-1,000 units/mg protein) and AchE Activity Assay Kit was obtained from Sigma-Aldrich (St Louis, Mo.).

In Vitro Skin Decontamination Experiments

A. Skin Samples

Adult human cadaver skin was obtained from the Pathology Department at the University of California San Francisco. Skin was taken from the abdomen and scalp (for hairy skin penetration study only) areas often donors and dermatomed using a Padgett Electro-dermatome (Padgett Instruments, Inc., Kansas City, Mo.) with target thickness of 400 μm, immediately sealed in aluminum foil and stored at 4° C. until use. Prior to experiments, skin samples were cut into circular sections to fit diffusion cells. Physical condition of skin samples was assayed visually to exclude any surface damage.

B. Decontamination Procedure

For soap-water and bleach-water washing, the dosed set was washed once with a small cotton balls wetted with 2% hand soap solution or 0.5% bleach solution, respectively, twice with cotton balls wetted with distilled de-ionized water and then dried with a dry cotton ball. Fuller's Earth decontamination was operated by applying 1 g of Fuller's Earth powder on dosed set, and removing the powder with dry cotton ball after 30 minutes. For RSDL decontamination, 3×3 cm RSDL pad was held by forceps and massaged on dosed area for 2 minutes, then a new piece of pad was placed on the same set and kept for 30 minutes. DDG was spread on a 3×3 cm patch in thickness of 2 mm, and applied on dosed set for 30 minutes. 2 minutes massage was carried out in the beginning of operation, except the control group in massage effect experiment. After removing the RSDL pad and DDG patch, skin surface was wiped with a dry cotton ball to remove possible surface residues.

C. Comparison of Decontamination Systems

Circular skin samples were clamped onto glass diffusion cells (Laboratory Glass Apparatus, Inc. Berkeley, Calif.) with 5 $cm^2$ surface area open to air. Receiving chambers (below the skin, 5 ml volume) were filled to capacity with receptor fluid stirred magnetically at ~500 rpm. Skin surface was dried with cotton pad and allowed to air dry for another 30 min before topical dosing. 10 μl dosing solution was applied on skin surface. After delayed decontamination time (2 to 60 minutes), the dosed set was either left untreated or decontaminated according to procedures descripted in previous section.

2 hours after decontamination started, skin was removed from diffusion cell and tape-stripped ten times with standard D-Squame strips (CuDerm Corporation, Dallas, Tex.) to separate SC. The first two strips containing the surface-removable dose residue were pooled with decontamination products in the same glass scintillation vial considered as washing section. The remaining eight strips were pooled into another vial representing tape-stripping SC (TS-SC). The tape-stripped skin samples were separated into the epidermis and dermis layers with a moderate heat (~60° C.). 2 mL and 4 mL Soluene® 350 were added in vials of epidermis and dermis, respectively, for 24 hour digestion. 2 mL out of 5 mL receptor fluid was collected for radioactivity determination. 15 mL scintillation cocktail was added to each fraction and stabilized overnight before assayed.

D. Stratum Corneum Reservoir

Cadaver skin samples were set up in the same diffusion cell system as delay decontamination study. 30 minutes post exposure to 10 μl paraoxon radiolabeled solution (0.05 mCi/mL radiolabeled and 2% v/v non-radiolabeled paraoxon in ethanol), dosed area was either left treatment or applied decontamination following procedures. One hour after dosing, skin sample was removed and tape-stripped 20 times to separate SC layer. Each tape-strip was determined on protein content using SquameScan 850A, collected in a different vial and determined for radioactivity after stabilizing in scintillation cocktail.

E. 24 Hours Hairy Skin Absorption/Penetration

Continuous flow-through diffusion cell system and glass diffusion cells with 1 $cm^2$ surface area open to air and receiving chamber volume of 3 mL volume (Laboratory Glass Apparatus, Inc. Berkeley, Calif.) were for 24 hours skin penetration assays. Skin samples with hair cut to less than 0.3 cm length were clamped onto diffusion cells filled to capacity with receptor fluid stirred magnetically at ~600 rpm. Temperature of diffusion cells was maintained using a Lauda E00 Heating Circulator (LAUDA DR. R. WOBSER GMBH & CO. KG, Germany) to achieve a skin surface temperature of 32° C. Receptor fluid was pumped to the diffusion cell at a rate of 4 mL/h using a Pump Pro® MPL (Watson-Marlow, Inc., Wilmington, Mass.), and collected every 2 hours using a Retriever Fraction Collector (Teledyne ISCO, Inc., Lincoln, Nebr.) for 24 hours.

30 minutes after dosing of 10 µl paraoxon radiolabeled solution on skin surface, the dosed set was either left untreated or decontaminated with soap-water washing or DDG. 24 hours after dosing, skin compartments were separated and collected as the description in delayed decontamination section. 15 m, scintillation cocktail was added to each fraction and stabilized overnight before assayed.

F. Radioactivity Measurement

Radioactivity measurements were performed on a Model 1500 Liquid Scintillation Counter (Packard Instrument Company, Downer Grove, Ill.). C-14 counting accuracy was audited by quenched and unquenched standards. Counting efficiency was equal to or greater than 95%. Background control and test samples were counted 3 min each for radioactivity.

G. Acetylcholinesterase Inhibition Activity

Human skin samples were set up on diffusion cells same as delayed decontamination experiments. 10 µl paraoxon solution (5% v/v non-radiolabeled paraoxon in ethanol) was applied on skin surface, and decontaminated with soap-water washing, RSDL and DDL systems 60 minutes post-exposure.

24 hours after dosing, receptor fluid was collected for AchE Inhibition activity measurements. 500 units/L AchE aqueous solution was prepared and mix with receptor fluid in 1:4 (v/v) to achieve the initial activity of 100 units/L. After 10 minutes, AchE activity of the mixture was determined by AchE Acidity Assay Kit following standard procedures to calculate AchE Inhibition activity of receptor fluid in units of AChE inhibited by 1 L of receptor fluid (units AChE/L RF).

In Vivo Skin Decontamination Preliminary Experiment

Haired mice (Laboratory Animal Resource Center, University of California San Francisco, Calif.) weighing 25-35 g were kept in kept in polycarbonate containers containing contact bedding at 21±2° C. and in light-controlled rooms (12-hour light/dark, full-spectrum lighting cycle with no twilling). Water and 4% Rodent Chow (Teklad HSD, Inc., WI) are provided.

Hair on dosing area were shaved before experiment. Soap-water washing, RSDL and DDG were provided as procedures descripted in delayed decontamination section 30 min pose exposure of 5% v/v non-radiolabeled paraoxon in ethanol. Animals were observed on their poising symptoms and lethality 24 hours after dosing.

Results

In Vitro Skin Decontamination Experiments

A. Comparison of Decontamination Systems

Figure 2:
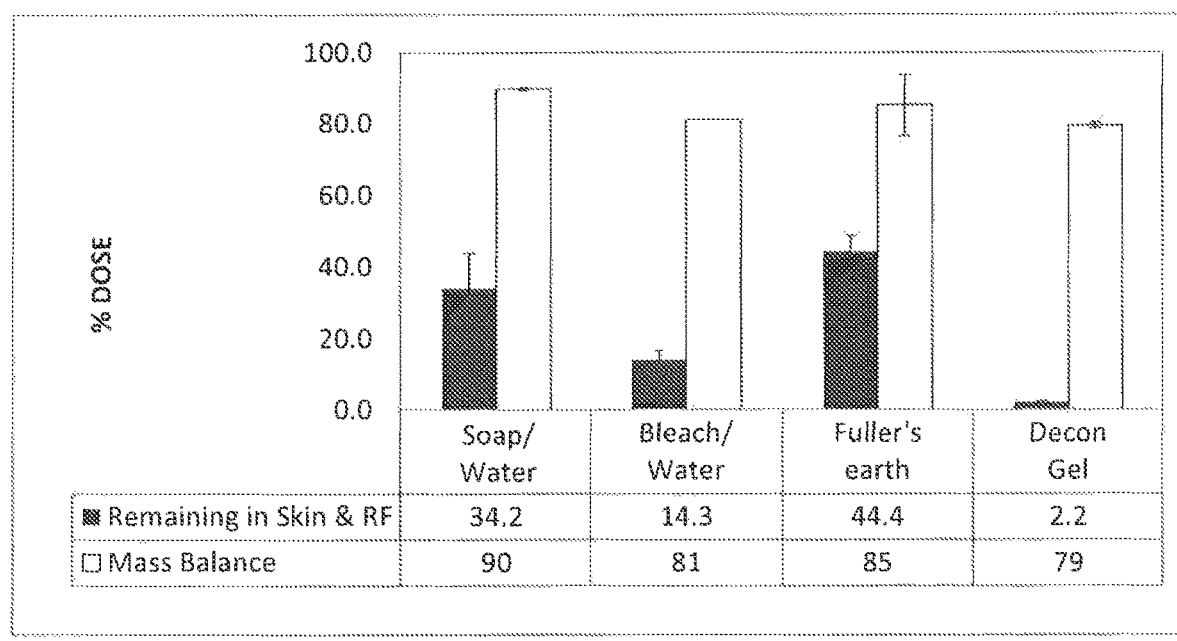
FIG. 2 depicts decontamination efficiency of four systems on terbinafine HCl (Log P=5.53) skin exposure. Column and error bar represent mean and standard deviation, respectively (n=3). Note that, DDG can more effectively inhibit skin absorption/penetration of the lipophilic model chemical than other decontamination products.

Decontamination efficiency of DDG on model chemical terbinafine HCl (Log P=5.53) was compared with soap-water washing, bleach-water washing and fuller's earth (FIG. 1). Decontamination was applied 5 minutes past dosing. The DDG group determined to have lowest percent dose absorbed in skin and receptor fluid (RF, FIG. 2).

Figure 3:
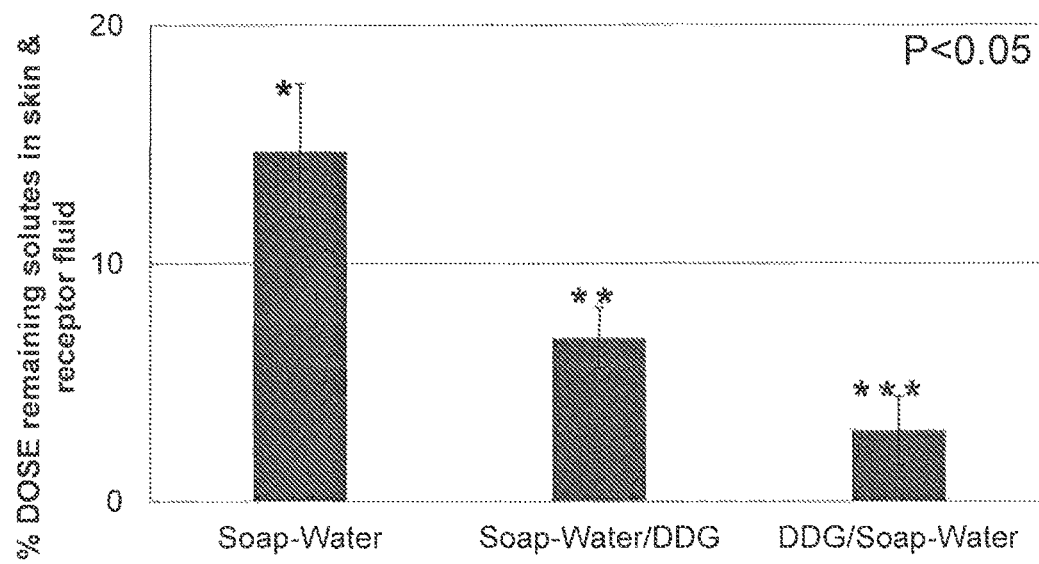
FIG. 3 depicts decontamination efficiency of soap-water washing only, soap-water washing applied before and after DDG on (top) salicylic acid (Log P=1.98) and (bottom) terbinafine HCl (Log P=5.53). Column and error bar represent mean and standard deviation, respectively (n=3). Groups with DDG applied showed significantly lower skin absorption/penetration than soap-water washing only groups. Significant higher skin absorption/penetration of hydrophilic model chemical, salicylic acid was observed in soap-water/DDG group than DDG group/soap-water group.
Figure 3:
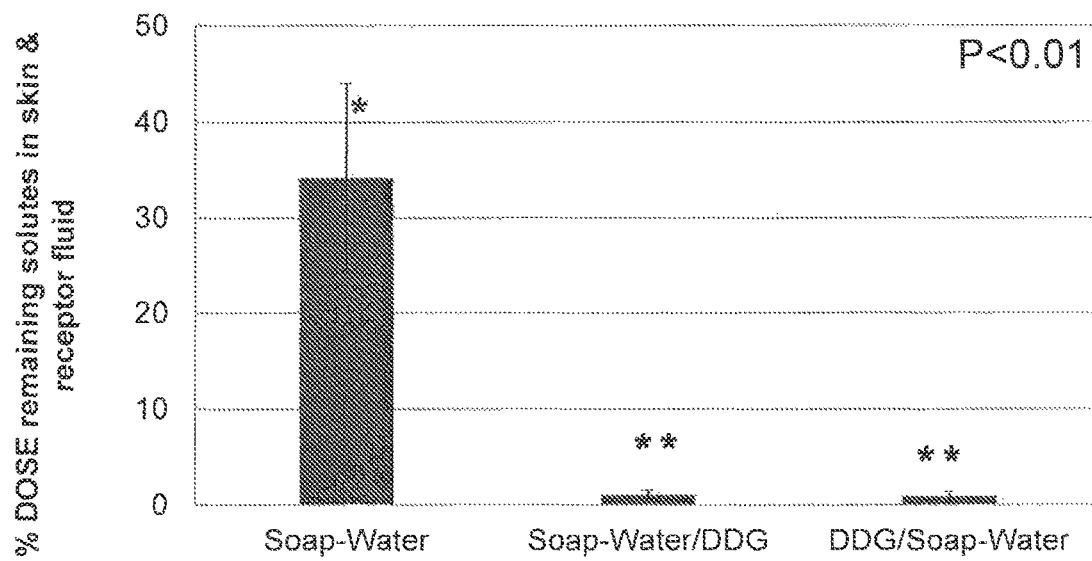

To optimize the operation procedure of DDG and verify the "wash-in" skin penetration enhancement effect of water-based skin decontamination methods, soap-water washing was applied before and after DDG application on hydrophilic model chemical, salicylic acid (Log P=1.98) and lipophilic model chemical, terbinafine HCl (Log P=5.53). Decontamination started 5 minutes after chemical exposure. Skin absorption/penetration of salicylic acid reduced the most when DDG was applied before soap-water washing (FIG. 3). The two groups including DDG application showed greater decontamination efficiency than the group of soap-water washing only. DDG significantly decreased amount of terbinafine in skin and receptor fluid, but the sequence of soap-water washing and DDG applied caused no significant difference on decontamination efficiency.

Figure 4:
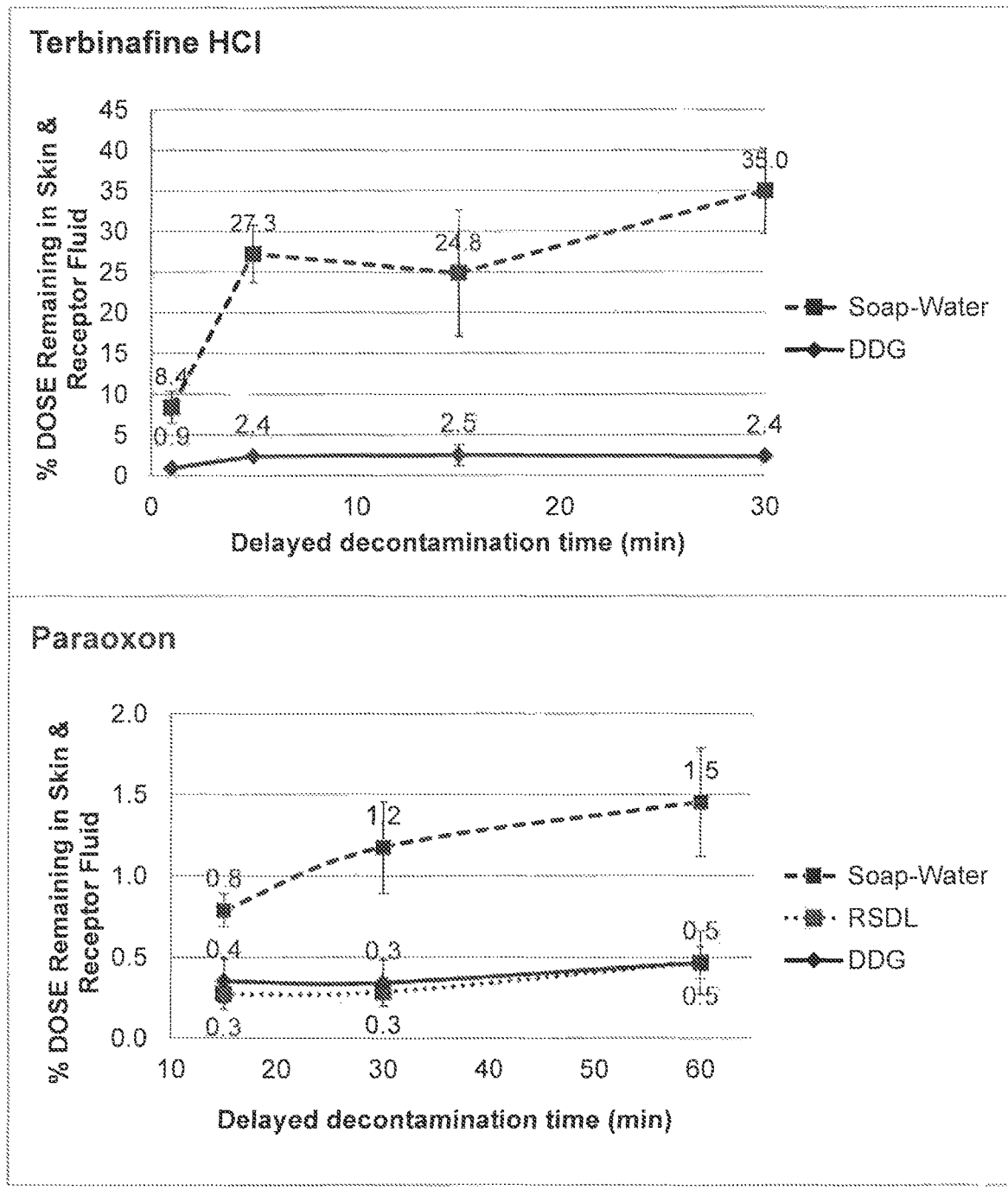
FIG. 4 depicts delayed decontamination of terbinafine HCl (top) and paraoxon (bottom). DDG had significant greater decontamination efficiency than soap-water washing. Each point is mean of triplicates, error bars represent standard deviations. Differences on % dose of model chemicals retained in skin and receptor fluid increased as chemical exposure time increased, suggesting DDG provides longer time for effective decontamination than soap-water washing. RSDL provides similar protection against paraoxon within 60 minutes delayed decontamination time.
Figure 5:
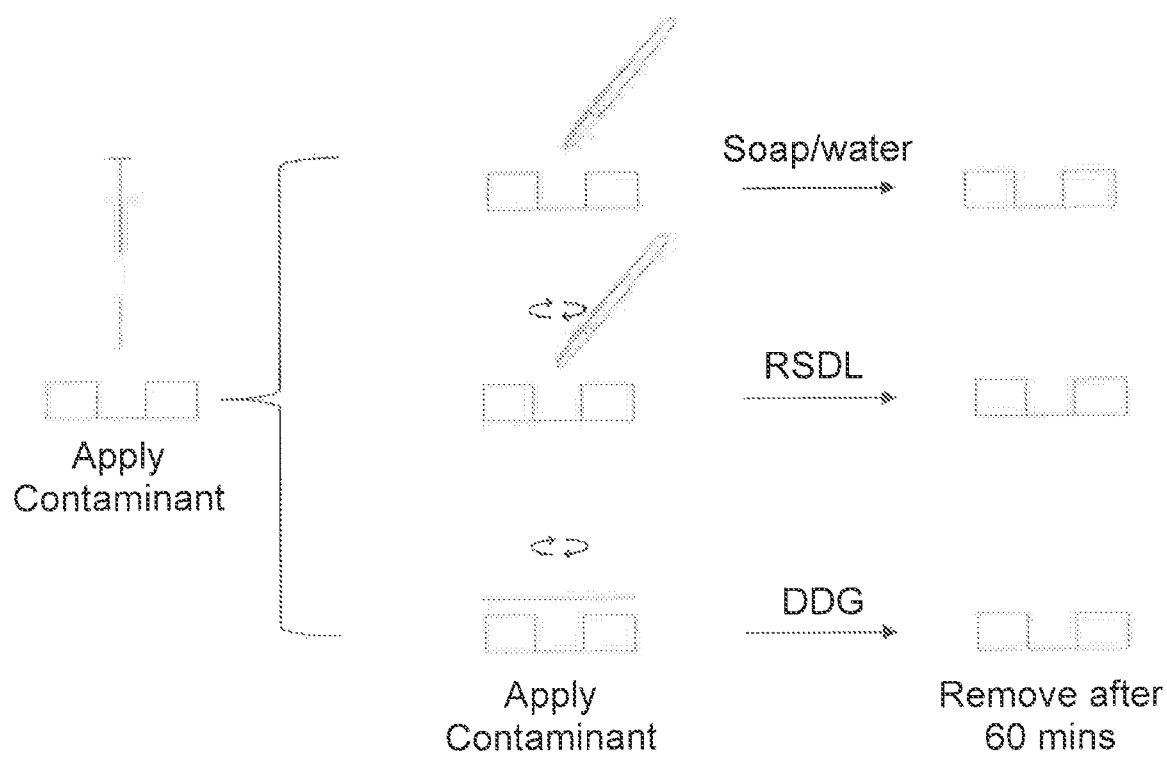
FIG. 5 depicts a flow diagram of a decontamination experiment using human skin. After application of contaminant, treatment is applied (soap and water, RSDL, or DDG). After 60 minutes treatment is removed if necessary and contamination testing can begin on skin samples.

Delayed decontamination efficiency of terbinafine was compared between soap-water washing and DDG with chemical exposure time from 2 to 30 minutes (FIG. 4). RSDL, the approved defense therapeutic device for chemical warfare agents (CWAs), was included in the evaluation against CWA simulate, paraoxon. Delayed decontamination time of paraoxon was prolonged to 60 minutes, but with otherwise similar methodology (FIG. 5).

Soap-water washing resulted in larger amounts of skin absorption and penetration of terbinafine and paraoxon at all delayed decontamination time points, and the differences increased as time increased, suggesting DDG provides more effective decontamination than soap-water washing, and the advantage is greater at longer chemical exposure time. DDG and RSDL had no significant difference on the decontamination efficiency of paraoxon within 60 minutes exposure time.

B. Stratum Corneum Reservoir

Figure 6:
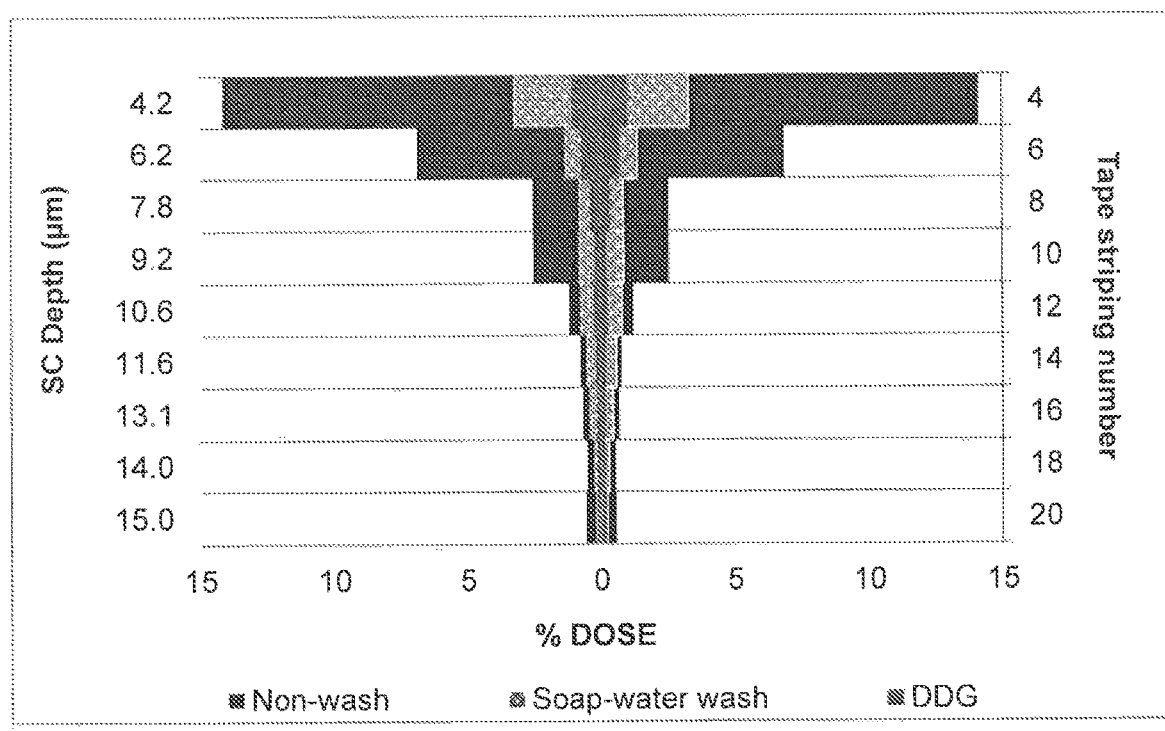
FIG. 6 depicts penetration profiles of paraoxon in correlation to SC depth and tape striping times. Each bar represents average of 5. Comparing to non-wash group, soap-water washing removed majority of chemical in superficial SC layer. DDG showed great decontamination efficiency.

Following 30 minutes dermal exposure to paraoxon and skin decontaminations. SC is removed layer by layer using tape stripping. Results show that majority of paraoxon locating in the superficial SC layers (SC reservoir) can be removed by soap-water washing, and DDG showed greater decontamination efficiency (FIG. 6).

C. 24 Hours Hairy Skin Absorption/Penetration

Figure 7:
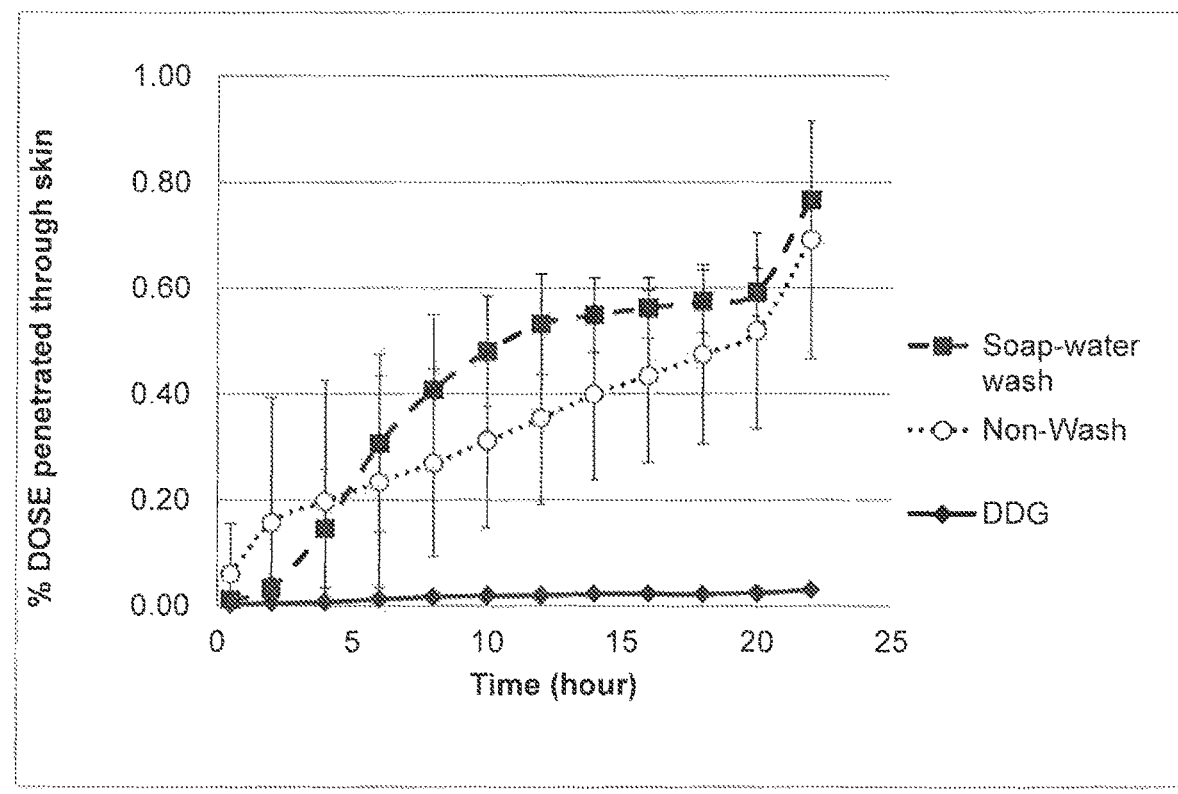
FIG. 7 depicts cumulative hair follicle skin penetration curves of paraoxon in comparison of non-wash, soap-water washing and DDG decontamination. Each point is mean of triplicates, error bars represent standard deviations. DDG significantly reduced paraoxon penetration in 24 hours after dermal exposure. Soap-water washing enhanced penetration flux, but caused no significant difference on total skin penetration.

Hairy skin penetration fluxes of paraoxon were compared among non-wash, soap-water washing and DDG. Soap-water washing resulted in no-significant reduction on total skin penetration at 24 hours after dosing, but increased penetration flux after decontamination applied, suggesting "water wash in" effect on hairy skin. Comparing with soap-water washing, DDG provides effective skin decontamination, and continuously reduced skin penetration (FIG. 7).

D. AchE Inhibition Activity

Figure 8:
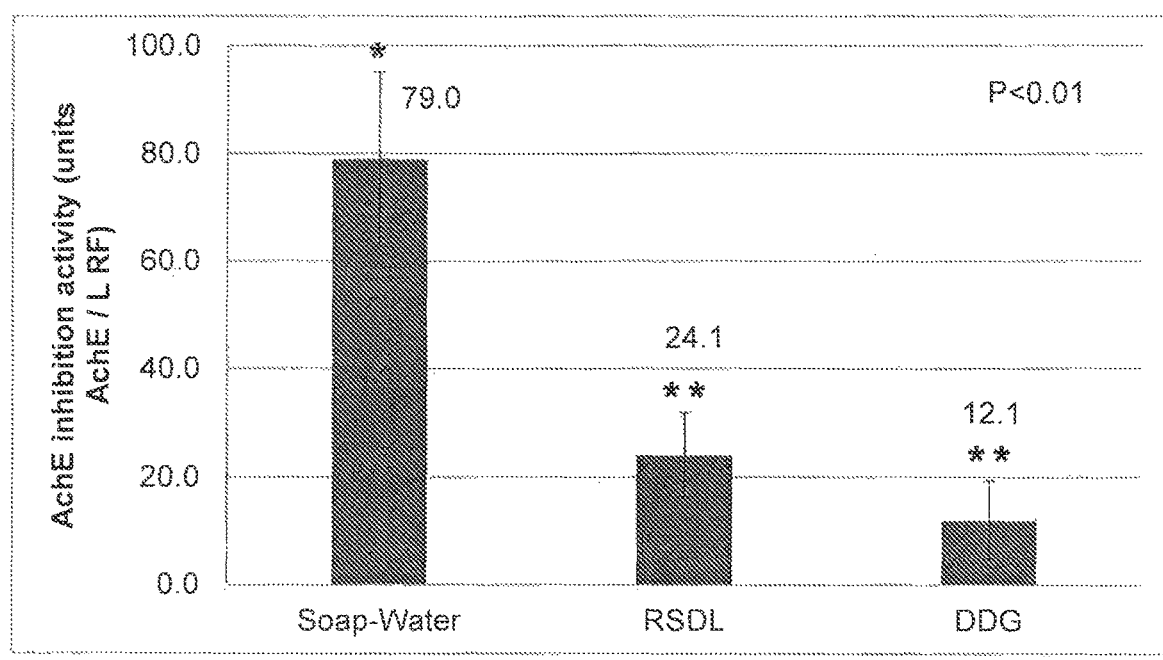
FIG. 8 depicts AchE inhibition activity of receptor fluid after three decontamination treatments expressed in units of AchE inhibited by 1 L receptor fluid (RF). Note that AchE inhibition activities of receptor fluid from RSDL and DDG groups were significantly lower than soap-water washing group, suggesting greater protection of RSDL and DDG against dermal exposure of paraoxon.

Decontamination efficiencies of soap-water washing. RSDL and DDG on paraoxon were confirmed by AchE inhibition activity assays. After 60 minutes delayed decontamination, skin samples were set for another 23 hours to allow paraoxon remaining in skin cumulate into receptor fluid. Higher AchE inhibition rate was shown in receptor fluid of skin soap-water wash group samples than those of RSDL or DDG groups (FIG. 8), suggesting more paraoxon remained in the skin and entering the system after soap-water washing; DDG and RSDL provided greater protection against paraoxon at long exposure time (60 minutes).

In Vivo Skin Decontamination

Figure 9:
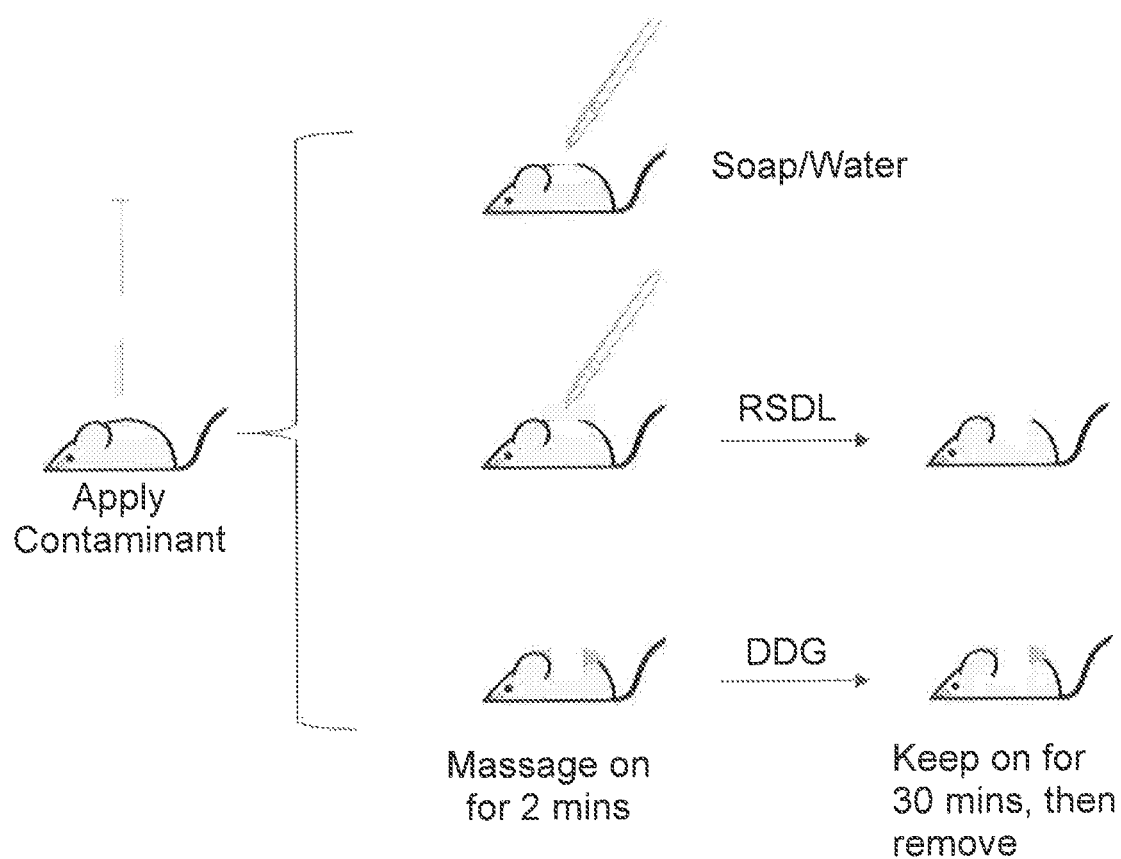
FIG. 9 depicts a flow diagram of a decontamination experiment using skin from live mice. After application of contaminant, treatment is applied (soap and water, RSDL, or DDG) and left on for about 30 minutes, after which treatment is removed if necessary.

Delayed decontamination efficiency of paraoxon was determined in vivo on mice model. Positive control group, receiving no treatment but exposing to same amount of paraoxon solution (5% v/v), showed poisoning symptoms in 1 hour post dosing, and reached 100% lethality within 3 hours of chemical exposure (FIG. 9).

Figure 10A:
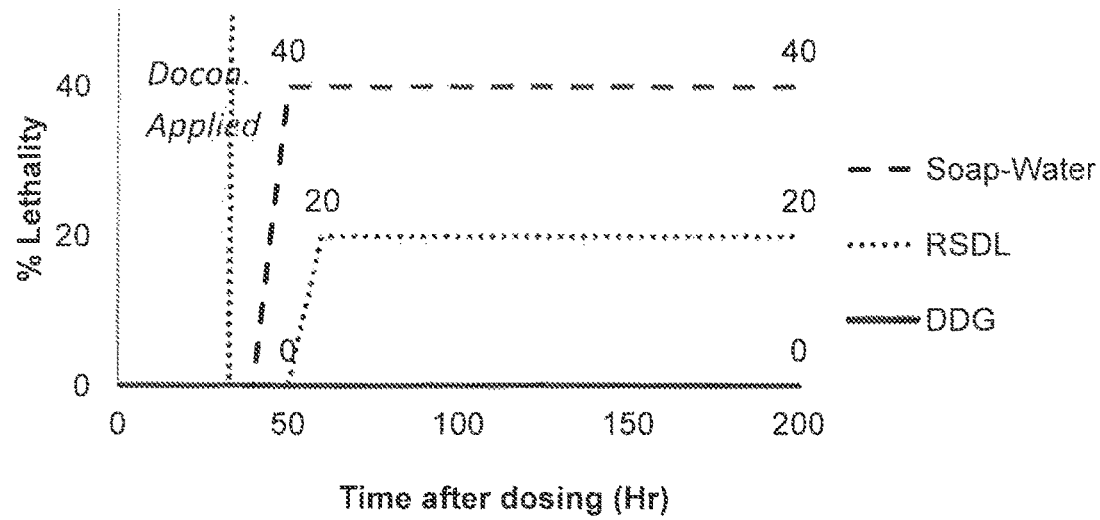
FIG. 10A depicts a delay of 30 minutes and FIG. 10B depicts a delay of 60 minutes, both following challenge by paraoxon. Soap-water washing and RSDL provided partial protection against paraoxon with 30 minutes delayed application (40% and 20% lethality in 24 hours). "Wash in" effect observed in "Soap-Water Wash" group—symptoms worsened after decontamination. All mice in the DDG group survived when decontamination was delayed by 30 min. In the 60 min delayed decontamination study. DDGel rescued 75% of mice, greater than with RSDL. Efficiency of DDGel decontamination is higher than that of RSDL and soap-water wash groups with different time decontamination delays.

With 30 minutes delayed decontamination (FIG. 10A), 40% animals in soap-water washing group showed significant increase of symptoms, and all passed away in 1.5 hours after dosing; 60% survived at 24 hours post dosing, suggesting that soap-water washing provide partially protection to paraoxon by reducing SC reservoir, but it also enhanced rate of paraoxon penetration and accelerated death of animals; 20% animals treated with RSDL passed away in 1 hour post dosing (30 minutes after decontamination). All animals in DDG group survived at 24 hours post dosing.

Figure 10B:
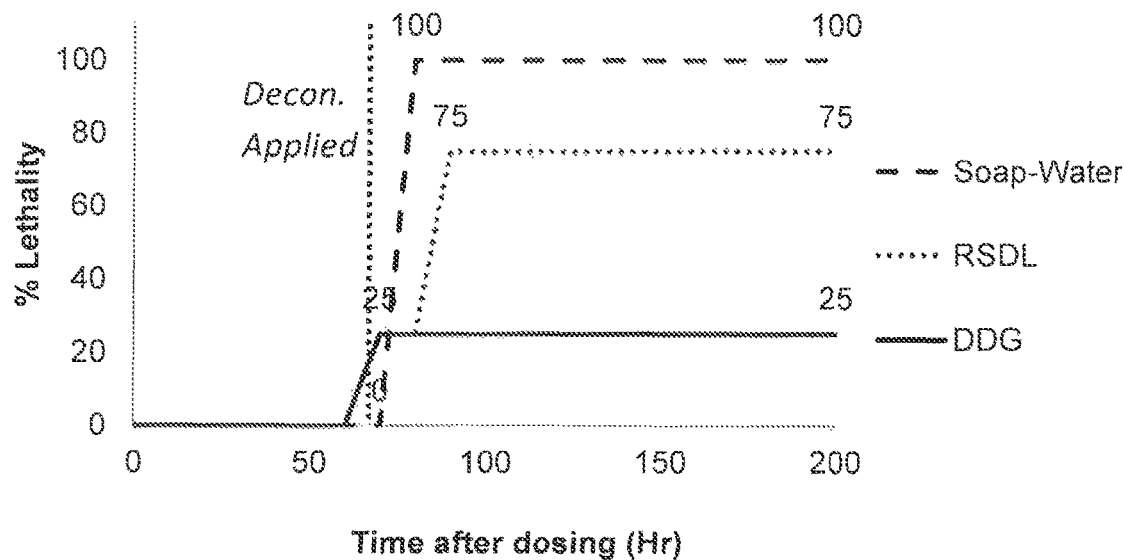
Figure 11A:
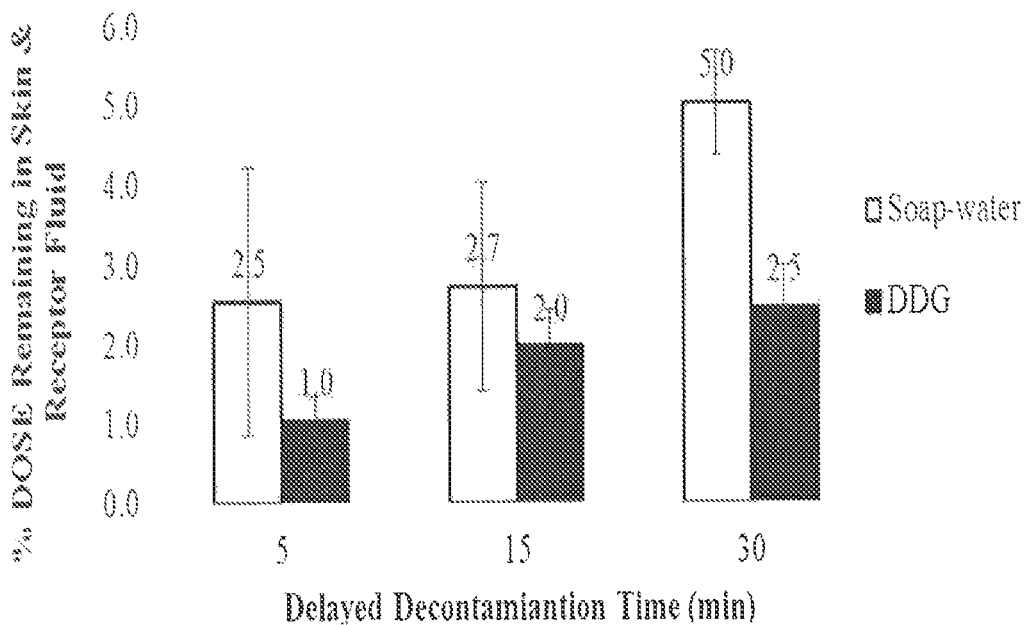
Figure 11B:
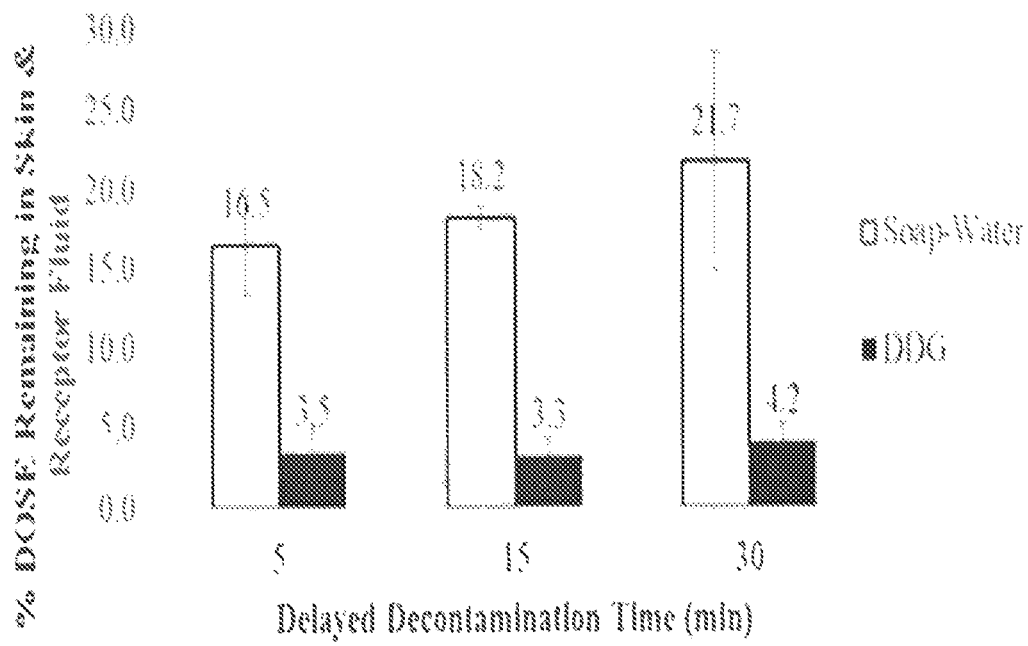
Figure 11C:
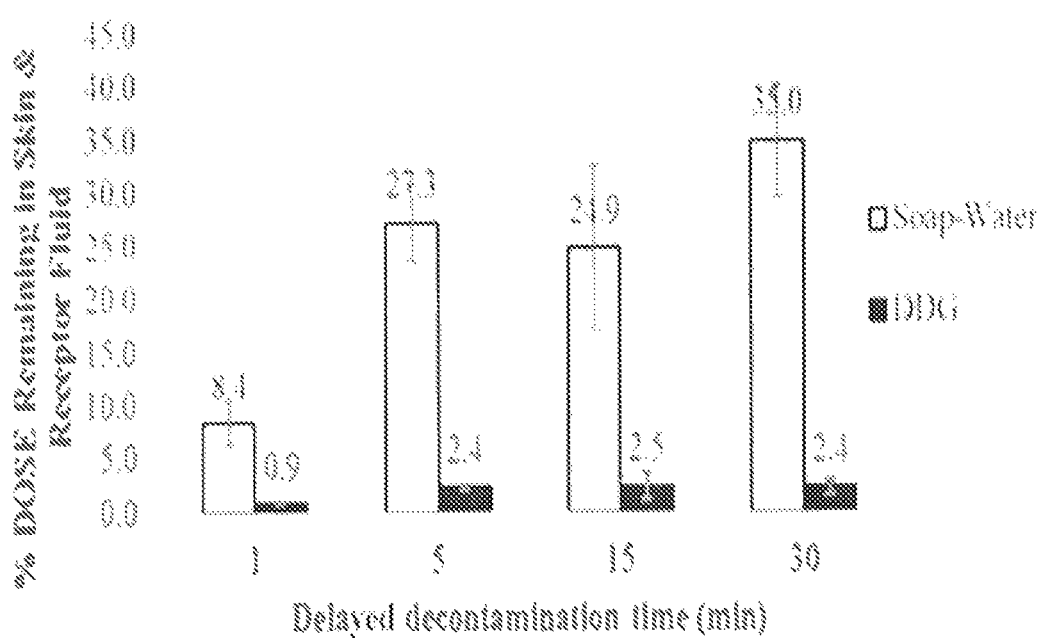

In 60 minutes delayed decontamination study (FIG. 10B), 20% animals in each group died before treatment applied and eliminated from final results. 25% treated animals in RSDL and DDG groups died in 5 minutes after decontamination applied, which are considered severely poisoned and too late to be saved by decontamination; the rest 75% animals in DDG group survived after treatment; RSDL group had another 50% animal died in 30 minutes after treatment (1.5 hour post dosing) and reached its final lethality of 75%; Consistent with the wash-in effect, an aggravation by poisoning was observed in soap-water group about 10 min after decontamination, and all animals in the group died in 20 minutes after decontamination (80 minutes post dosing).

CONCLUSION

DDG can effectively reduce chemical reservoir in SC and continuously inhibit skin penetration, providing longer time and greater opportunity for effective decontamination than other skin decontamination systems.

Example 2

In Vitro Skin Decontamination Experiments

1) The compositions and methods of the present disclosure will be tested for extend delayed decontamination (e.g., 24 hours).

Trimethyl phosphate, dimethyl methylphosphonate and parathion will be prepared in ethanol with specific radioactivity of 0.05 mCi/mL and non-radio labeled chemical concentration of 20 mg/mL.

Adult human cadaver skin will be obtained from the abdominal areas of multiple donors and dermatomed using a Padgett Electro-dermatome (Padgett Instruments. Inc., Kansas City, Mo.) with target thickness of 400 µm. They will be immediately sealed in aluminum foil and stored at 4° C. until use. Prior to experiments, skin samples will be cut into circular sections to fit diffusion cells. The physical condition of skin samples will be assayed visually and any samples with visual surface damage are excluded.

The delayed decontamination study will be conducted according to procedure described in "Materials and Methods: II. In vitro Skin Decontamination Experiments: C. Comparison of Decontamination Systems" section. Circular skin samples will be clamped onto glass diffusion cells with 5 $cm^2$ surface area opening. Receiving chambers will be filled to capacity with receptor fluid stirred magnetically at ~500 rpm. Skin surface will be dried with cotton pad and allowed to air dry for another 30 min before topical dosing. 10 µl of dosing solution are applied on the skin surface. Delayed decontamination times of 15 minutes, 1 hour, 2, 4, 8, 12 and 24 hours will be tested. After the delayed decontamination time, the dosed set of samples will be decontaminated according to procedures described in "Materials and Methods: II. In vitro Skin Decontamination Experiments: B. Decontamination Procedure" section.

After the designated time, the skin samples will be removed from the diffusion cell and tape-stripped ten times with Standard D-Square strips (CuDerm Corporation, Dallas, Tex.) to separate SC. The first two strips will be pooled with decontamination products in the same glass scintillation vial considered as washing section. The remaining eight strips will be pooled into another vial representing tape-stripping SC (TS-SC). Epidermis and dermis layers will be separated with a moderate heat (~60° C.) and digested 24 hours with 2 mL and 4 mL Soluene® 350, respectively. 2 mL out of 5 mL receptor fluid will be collected for radioactivity determination. 15 mL scintillation cocktail will be added to each fraction and stabilized overnight before assayed.

Procedure of stratum corneum reservoir assay will be the same as "Materials and Methods: II. In vitro Skin Decontamination Experiments: D. Stratum Corneum Reservoir" section. Cadaver skin samples will be set up in the same diffusion cell system as delay decontamination study. 30 minutes post exposure to 10 µl trimethyl phosphate, dimethyl methylphosphonate or parathion dosing solution (0.05 mCi/mL radiolabeled and 2% v/v non-radiolabeled chemicals in ethanol), dosed area will be either left treatment or applied decontamination following procedures. One hour after dosing, skin samples will be removed and tape-stripped 20 times to separate SC layer. Each tape-strip will be collected in a different vial and determined for radioactivity after stabilizing in scintillation cocktail.

For 24 hours skin penetration study, circular skin samples will be clamped onto continuous flow-through diffusion cell system and glass diffusion cells with 1 $cm^2$ surface area opening. Receiving chambers under the skin will be filled to capacity with receptor fluid stirred magnetically at ~600 rpm. Temperature of diffusion cells will be maintained using heating circulator system to achieve a skin surface temperature of 32° C. Receptor fluid will be pumped to the diffusion cell at a rate of 4 mL/h using a Pump Pro® MPL (Watson-Marlow, Inc., Wilmington, Mass.), and collected every 2 hours using a Retriever Fraction Collector (Teledyne ISCO, Inc., Lincoln, Nebr.) for 24 hours. 30 minutes after applied 10 µl radiolabeled dosing solution on skin surface, the dosed set will be either left untreated or decontaminated with soap-water washing or DDG. 24 hours after dosing, skin compartments will be separated and collected as the description in delayed decontamination section. 15 mL scintillation cocktail will be added to each fraction and stabilized overnight before assayed.

Radioactivity measurements will be performed on a Model 1500 Liquid Scintillation Counter (Packard Instrument Company, Downer Grove, Ill.). The results of comparing skin absorption and elimination kinetics from the control will show decontamination efficiency parameters such as reducing skin surface chemical residues, minimizing stratum corneum chemical reservoir, and decreasing deep/systemic diffusion. As such, the methods and compositions of the present disclosure can reduce skin surface chemical residues by about, or more than about, 5%, 10, 20, 30, 40, 50, 60, 70, 80, 90 or about 100%. These values can be used to define a range, such as from about 10% to about 50%. The methods and compositions of the present disclosure can minimize the stratum corneum chemical reservoir by about, or more than about, 5%, 10, 20, 30, 40, 50, 60, 70, 80, 90 or about 100%. These values can be used to define a range, such as from about 20% to about 60%. The methods and compositions of the present disclosure can decrease deep and/or systemic diffusion by about, or more than about, 5%, 10, 20, 30, 40, 50, 60, 70, 80, 90 or about 100%. These values can be used to define a range, such as from about 5% to about 40%.

Example 3

In Vitro Skin Decontamination Experiments

A comparison of decontamination efficiencies for the prolong delayed decontamination time of 90 and 120 minutes will be compared between soap-water washing, RSDL and DDG for CWAs and other simulants on human skin model in vitro.

Figure 12A:
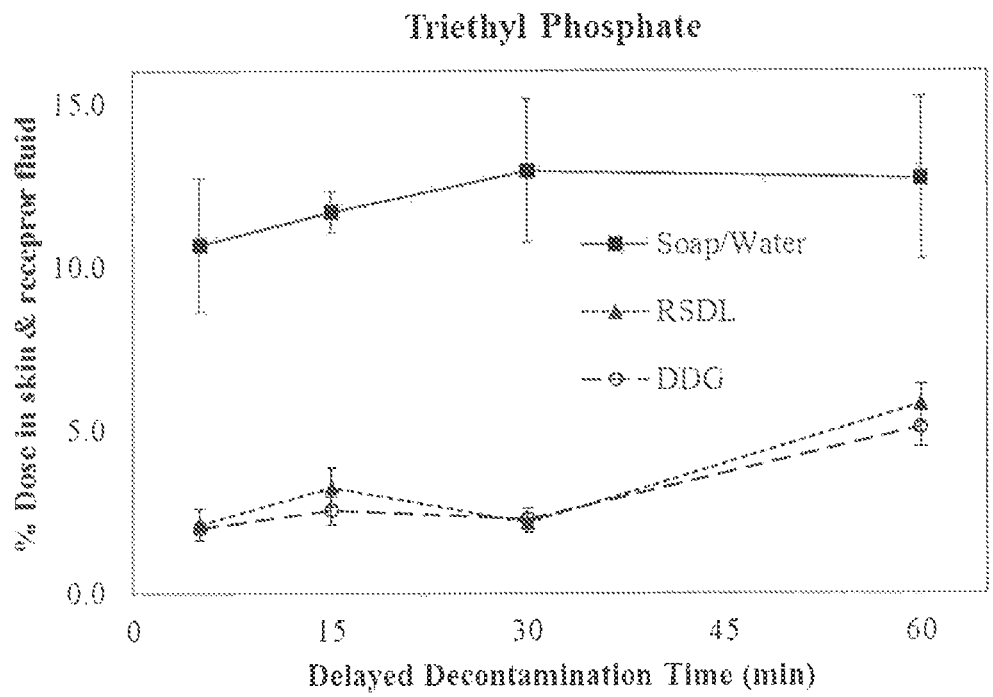
FIG. 12 depicts the comparison of time decontamination and skin penetration relationship of three decontamination methods: soap-water washing, RSDL, and DDG treatment for triethyl phosphate (FIG. 12A) and paraoxon (FIG. 12B) in Example 5.
Figure 12B:
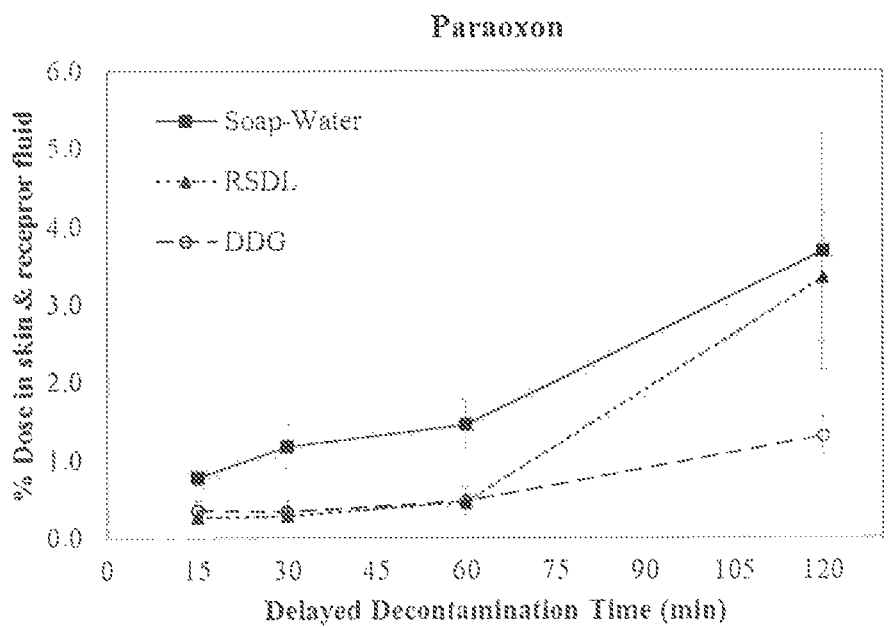

A delayed decontamination study of paraoxon (0.05 mCi/mL radiolabeled and 2% v/v non-radiolabeled paraoxon in ethanol) will be extended to delayed decontamination times of 90 and 120 min. Experimental procedure will be consistent with "Materials and Methods: II. In vitro Skin Decontamination Experiments: C. Comparison of Decontamination Systems" section. Circular skin samples will be clamped onto 5 cm$^2$ surface area opening glass diffusion cells filled to capacity with receptor fluid. Skin surface will be dried with cotton pad and allowed to air dry for another 30 min before topical dosing. 10 µl of a paraoxon dosing solution will be applied on the skin surface. After delayed decontamination times of 90 and 120 minutes, the dosed set will be decontaminated with soap-water, RSDL and DDG according to procedures descripted in "Materials and Methods: II. In vitro Skin Decontamination Experiments: B. Decontamination Procedure" section.

Radioactivity measurements will be performed on a Model 1500 Liquid Scintillation Counter (Packard Instrument Company, Downer Grove, Ill.). The efficiency of delayed skin decontamination is an important index for evaluation of skin decontamination method. The methods and compositions of the present disclosure, e.g., DDG, when compared to other decontamination methods, e.g., RSDL, show an improved or increased efficiency at delayed skin decontamination times (30+ minutes). The methods and compositions of the present disclosure are effective for skin decontamination, etc. at delayed skin decontamination times of about 1 hour, 1.5, 2, 3, 4, 5, 6, 7, 8, 9, 10, 1, 12, 18, 24, 36 and about 72 hours. These values can be used to define a range, such as from about 1 to about 4 hours. The methods and compositions can work not only for short time dermal exposure to toxic chemicals, e.g., 30 min, but also at longer times, e.g., 90 min, 120 min.

Example 4

In Vivo Animal Toxicity Experiment

An in vivo animal toxicity and decontamination test using CWAs or simulants will be tested on a guinea pig model.

Haired guinea pigs will be used for in vivo skin decontamination assays of model chemicals, paraoxon and parathion. Decontamination efficacy will be evaluated by % survival of animals at 24 hours after topical dosing of 5-$LD_{50}$ (five times the median lethal dose). About 40 guinea pigs will be included in each group. Hair on dosing area will be shaved before experiment. Soap-water washing, RSDL and DDG will be provided as procedures descripted in "Materials and Methods: II. In vitro Skin Decontamination Experiments: B. Decontamination Procedure" section at 30 min. 60 min, 90 min pose exposure of paraoxon and parathion in ethanol.

Acute derma-toxicology and related skin decontamination studies in laboratory animals are useful for the assessment of DDGel decontamination and detoxification efficacy against chemical warfare agents/simulants prior to their future application to humans. A Guinea pig model will be used because of the close biological similarities to humans. Their epidermis thicknesses is similar to humans, as well as they have similar distinct skin layers and a similar number of blood vessels. Guinea pigs also have similar skin reactions to chemicals.

The compositions and methods of the present disclosure is a longer-lasting and effective decontaminant of chemicals such as paraoxon compared to other decontamination methods, such as soap-water washing. DDGel, one embodiment of the present disclosure, can remove paraoxon from the skin surface as well as reduce its toxicity (e.g., inhibiting AchE activity). It can functions in delayed decontamination, as much as 30 to 60 minutes post dermal exposure, both in vitro and in vivo. The efficiency of DDGel is superior as compared to other decontamination methods in the time-response of DDGel and the decontamination of normal skin versus hairy skin.

Example 5

Comparison of the Efficiencies of Different Decontamination Methods

The decontamination efficiency of model chemicals with different methods was tested. The decontamination efficiency of DDGel compared to soap-water wash, bleach-water wash, Fuller's earth and RSDL was tested in human skin with an in vitro diffusion system.

The decontamination efficiency of DDGel on model chemicals triethyl phosphate (TEP), paraoxon and butenafine HCl was compared with soap-water wash, bleach-water wash and Fuller's earth. The approved defense therapeutic device for CWAs, RSDL, was included in the evaluation against CWA simulants, TEP and paraoxon.

Aliquots of 10 μL [14C]-radiolabeled model chemical was applied on dermatomed human skin and incubated with an in vitro skin diffusion system. After defined dermal exposure times of about 5, 15, 30, 60, or 120 minutes the skin surface residue was removed with selected decontamination methods followed with tape strips to collect stratum corneum. The remained skin was separated into epidermis and dermis with heating (60° C. for 30 sec). Receptor fluid was collected representing the deep/systemic penetrated. All collected samples were measured for radioactivity as percent applied dose.

Post 15 minutes topical dosing, the application of DDG resulted in a significant reduction of the model chemical absorption in skin and receptor fluid (RF) than soap-water wash, bleach-water wash and Fuller's earth ($p<0.05$). Results show that soap-water wash could remove a large amount of the applied chemical from skin surface. However, in most of cases, it could not extract the chemical retained in the SC "reservoir." As the result, the model chemicals such as salicylic acid and butenafine HCl could be released from the "reservoir" continuously, penetrating through the skin layer into the receptor at all time points. FIGS. 11A, 11B and 11C show the comparison of decontamination efficiency of soap-water wash and DDGel following 2 to 30 minutes of post dermal exposure by panthenol, salicylic acid and butenafine HCl. Each bar represents the mean (±S.D.) of 5 samples. The amounts recovered in the receptor fluid were significantly higher than those of DDGel decontamination group at each time point ($p<0.05$). A significant amount of panthenol in receptor fluid samples was found in the soap-water wash group only when compared to that of DDGel group, ($p<0.05$) at 30 minutes. This suggests that a slow diffusion process occurred in earlier time points (5 to 10 minutes post dosing).

The decontamination time of TEP and paraoxon was increased to 60 and 120 minutes, respectively, and RSDL was included in the comparison. For both CWA simulants, soap-water wash showed lower decontamination efficiency than RSDL and DDG within 60 minutes exposure time. DDGel removed a significantly higher level of paraoxon than the other two methods with 120 minutes delayed decontamination. RSDL provided similar protection against both CWA simulants within 60 minutes delayed decontamination time for both model chemicals. FIGS. 12A and 12B show the comparison of time decontamination and skin penetration relationship of three decontamination methods: soap-water washing, RSDL, and DDGel treatment for triethyl phosphate (12A) and paraoxon (12B). Each symbol represents the mean (±S.D.) of 5 samples.

Example 6

Comparison of Penetration/Decontamination Rates in Various Skins Conditions

The decontamination efficiency of DDGel on normal and hairy human skin in vitro was tested. A [$^{14}$C]-paraoxon solution was applied to 1 cm of the surface of normal and hairy human skin in vitro, then removed 30 minutes after by DDGel or soap-water washing. The total [$^{14}$C]-paraoxon penetrated into the receptor fluid measured at the defined time points throughout the whole experiment was measured.

Figure 13A:
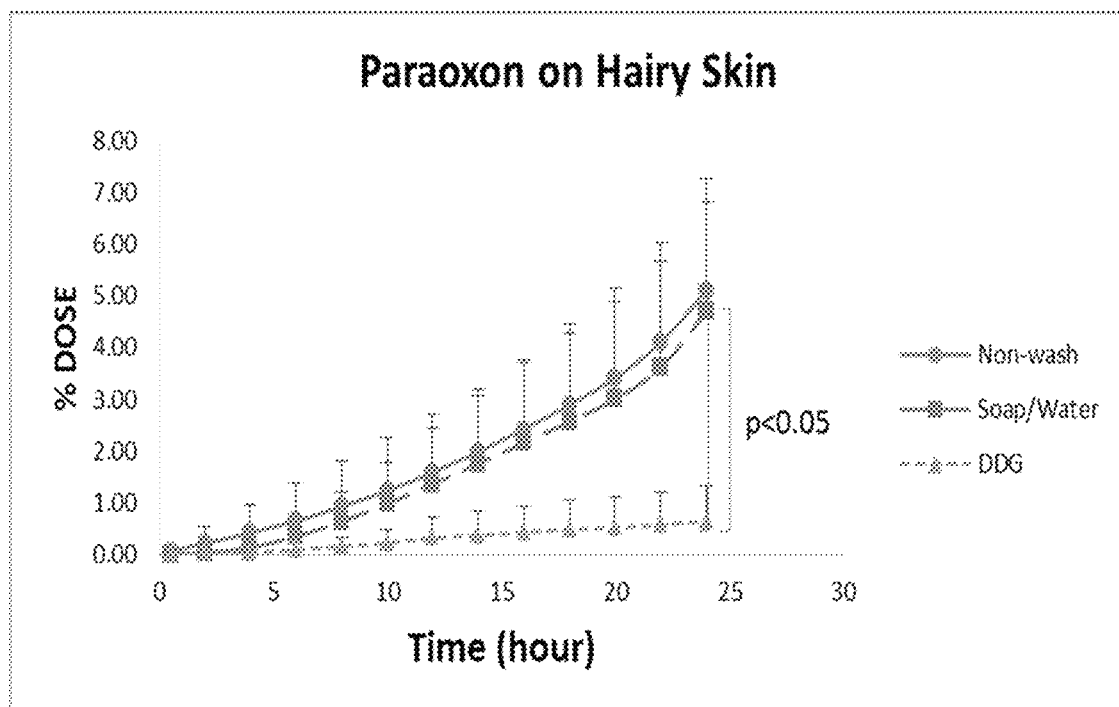
FIG. 13 depicts the cumulative hair skin (FIG. 13A) and normal skin (FIG. 13B) penetration curves of paraoxon in comparison with non-wash, soap-water washing and DDGel decontamination in Example 6.
Figure 13B:
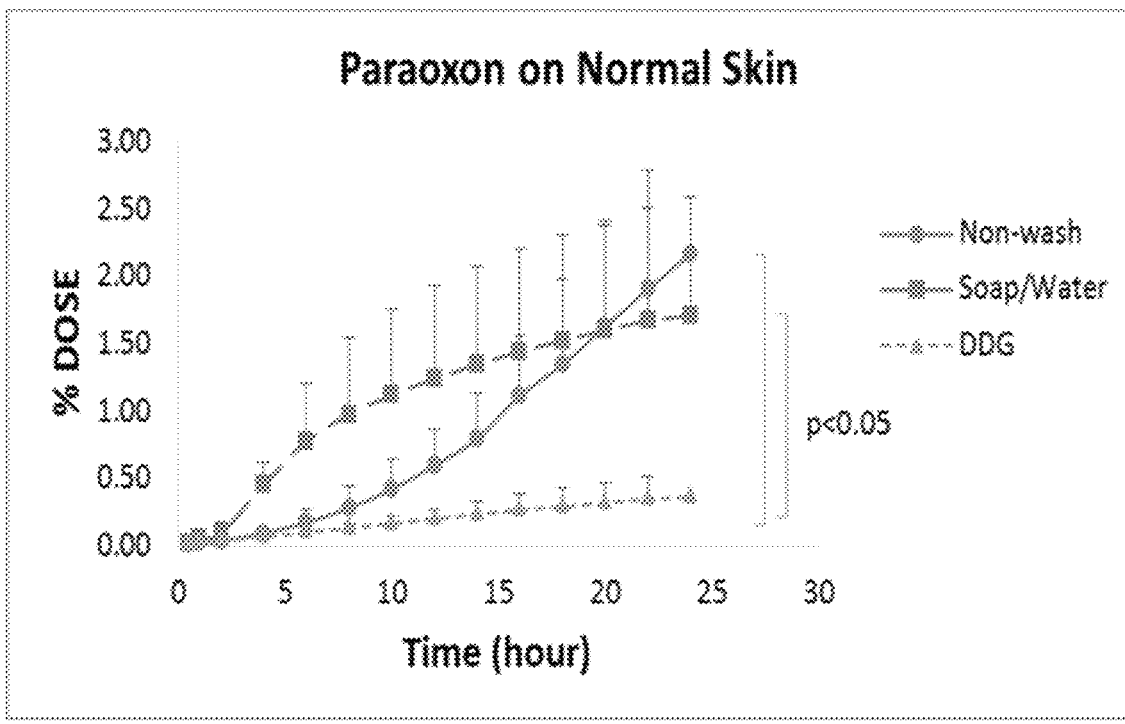

Hair follicles are one of the major dermal absorption pathways and a region of chemical reservoirs. As a result, more paraoxon penetrated the hairy skin. The total amount in the receptor fluid in hairy skin was twice that of normal skin (p<0.05). For the hairy skin penetration fluxes, soap-water washing resulted in no reduction in skin penetration. The total penetrated was the same as that of non-wash group. This suggests that the soap-water wash could not reduce the amount of contaminant penetrating the skin and it could not block the deeper diffusion of the retained chemical in the SC. In contrast, DDGel provided effective skin decontamination, and continuously reduced skin penetration. FIGS. 13A and 13B show the cumulative hair skin and normal skin penetration curves of paraoxon in comparison with non-wash, soap-water washing and DDGel decontamination. Each point represents the mean±S.D (n=3). DDGel significantly reduced paraoxon penetration in 24 hours after dermal exposure than those of non-wash and soap-water wash groups (P<0.05).

In non-wash normal and hairy skin groups, the percent dose recovery of paraoxon in the receptor fluid continuously increased until the end of experiment. However, the total amount in the receptor fluid in the hairy skin was more than twice that of the normal skin. For the normal skin group, an absorption peak was observed within a few hours after washing, but the total penetrated was similar to that of the non-wash group, which further suggests a "wash-in" effect of soap-water wash in the decontamination of paraoxon. DDGel provided significant effective on-skin decontamination, and continuously reduced skin penetration both in hairy and normal skin groups (less than 1% applied dose penetrated into the receptor fluid) compared those in no-wash and soap-water wash groups (p<0.05).

Example 7

Binding Affinity Screening of DDGel Active Decontamination Ingredients

The decontamination potential and binding affinity of polymers carboxymethyl cellulose, Lutrol®, Kollidon® SR, and chemical absorbent Fuller's earth to [$^{14}$C]-paraoxon was tested.

[$^{14}$C]-Paraoxon and each active binding materials were placed in a dialysis tube and incubated at 37° C. up to equilibrium reached. The binding rate was calculated as mole chemical/g active material.

Figure 14:
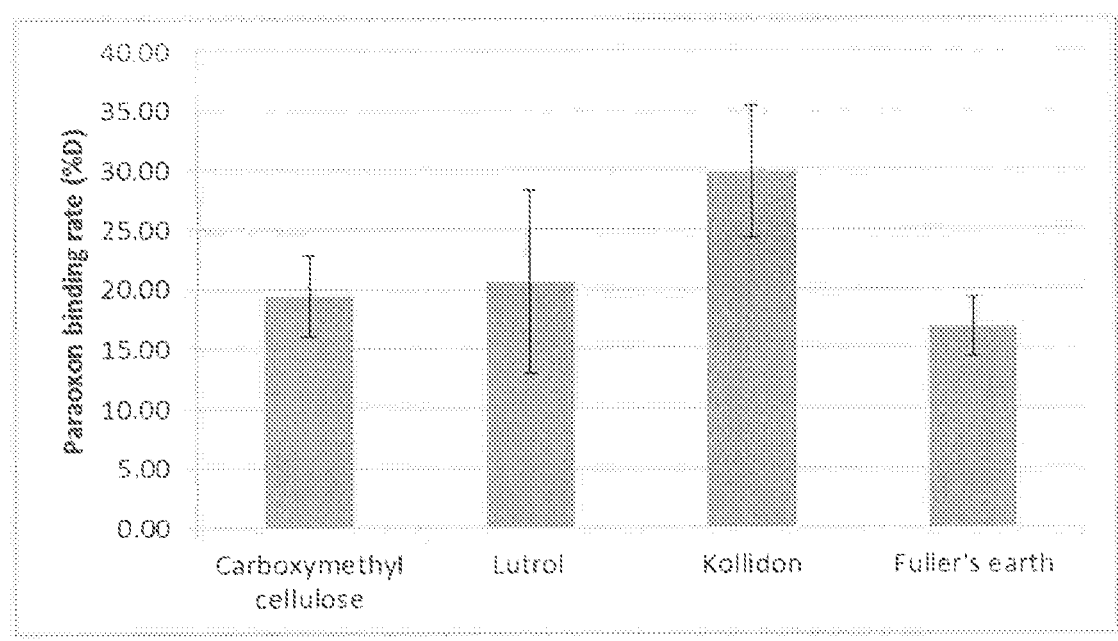
FIG. 14 depicts the [$^{14}$C]-Paraoxon binding affinity to polymers carboxymethyl cellulose, Lutrol®, Kollidon® SR, and Fuller's earth for Example 7.

FIG. 14 shows the [$^{14}$C]-Paraoxon binding affinity to polymers carboxymethyl cellulose, Lutrol®, Kollidon® SR, and Fuller's earth. Each bar represents the mean±S.D. of 5 samples. Kollidon® SR has the highest paraoxon binding rate at 29.9% dose which is statistically higher than rest of the ingredients (p<0.05). Kollidon® SR is a polyvinyl acetate (PVAc) and povidone (PVP) based matrix is a retardant with universal binding ability. PVP is soluble in water and other polar solvents, such as various alcohols, including methanol and ethanol (Wohlfarth, 2010). When dry, PVP is a light flaky hygroscopic powder, readily absorbing up to 40% of its weight in atmospheric water. In solution, it has excellent wetting properties and readily forms films. When PVP is mixed with carboxymethyl cellulose (CMC), the mixture can swell to absorb fluids from outside (Roya et al, 2010). These components, and combinations thereof, as provided in the present disclosure provide, in part, the superior results of the compositions and methods. In some embodiments, a number of components, e.g., 1, 2, 3, 4, 5 or 6, can have a binding affinity to paraoxon, for example, at or above 5, 6, 7, 8, 9, 10, 1, 12, 13, 14, 15, 16, 17, 18, 19 or at or above 20%. These values can be used to define a range, such as about 5 to 20%.

Example 8

Binding Affinity Screening of Kollidon® SR Components

The decontamination potential and binding affinity of Kollidon® SR components to various chemicals was tested. The two major components of Kollidon® SR is PVAc and PVP.

Eight model chemicals with different physicochemical properties and polymer solution in dialysis tubing were incubated at 37° C. for up to 24 hours to reach equilibrium. The binding rate was calculated as the chemical concentration in the dialysis tubing (mole chemical/g polymer).

Figure 15:
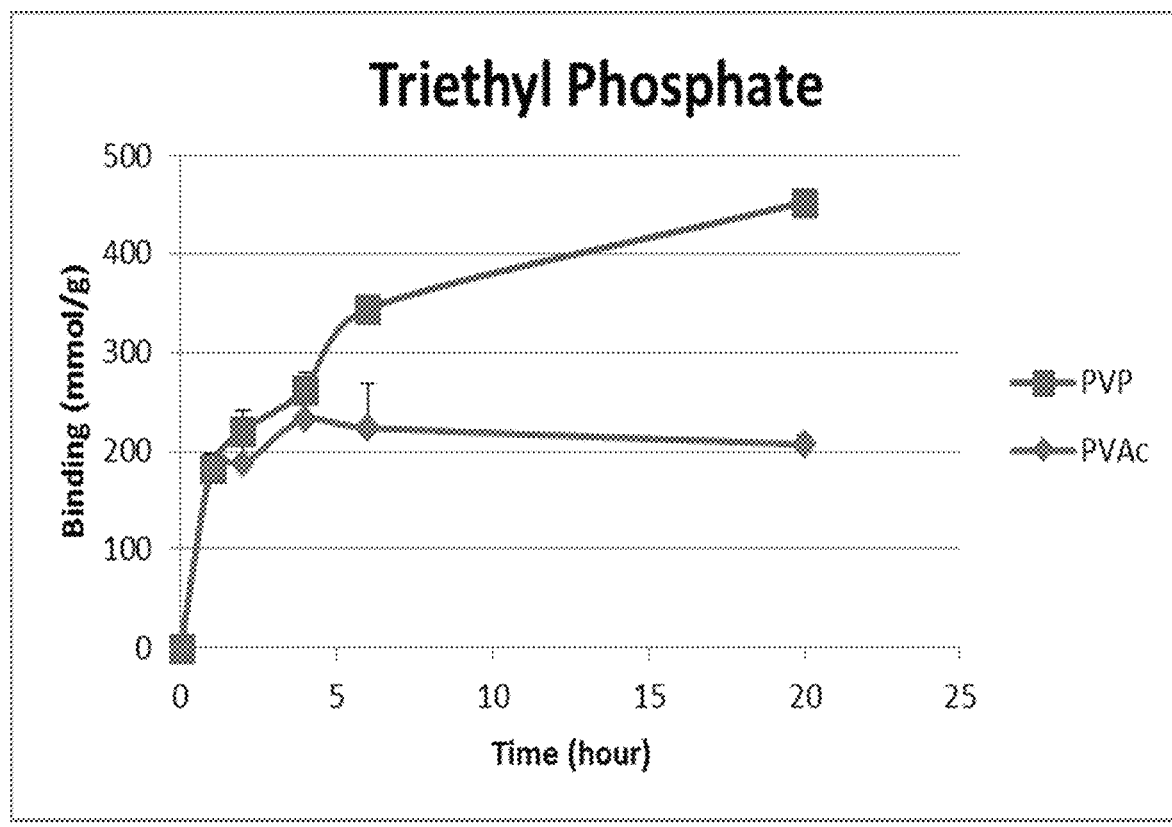
FIG. 15 depicts PVAc and PVP binding affinities to triethyl phosphate for Example 8.
Figure 16:
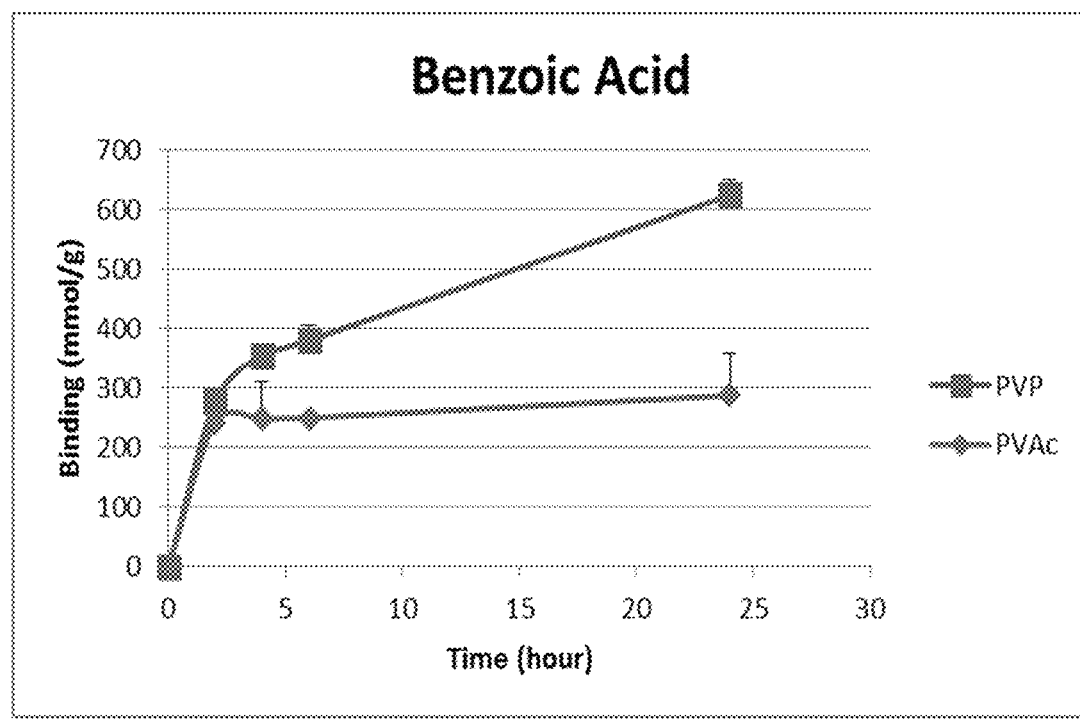
FIG. 16 depicts PVAc and PVP binding affinities to benzoic acid for Example 8.
Figure 17:
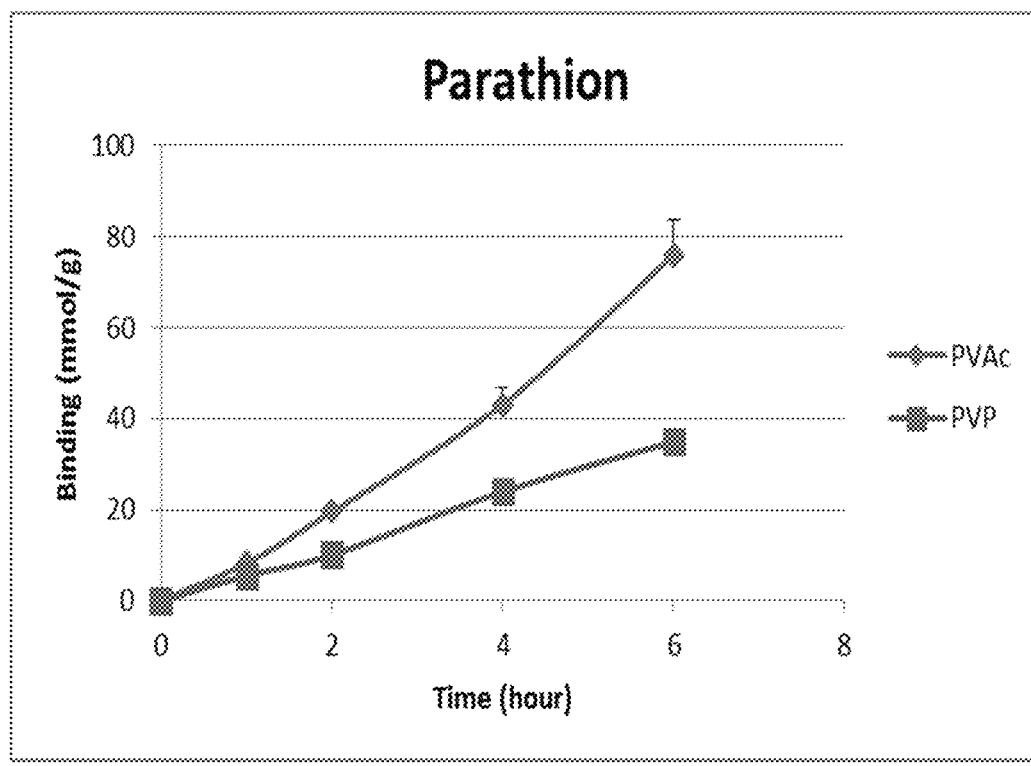
FIG. 17 depicts PVAc and PVP binding affinities to parathion for Example 8.
Figure 18:
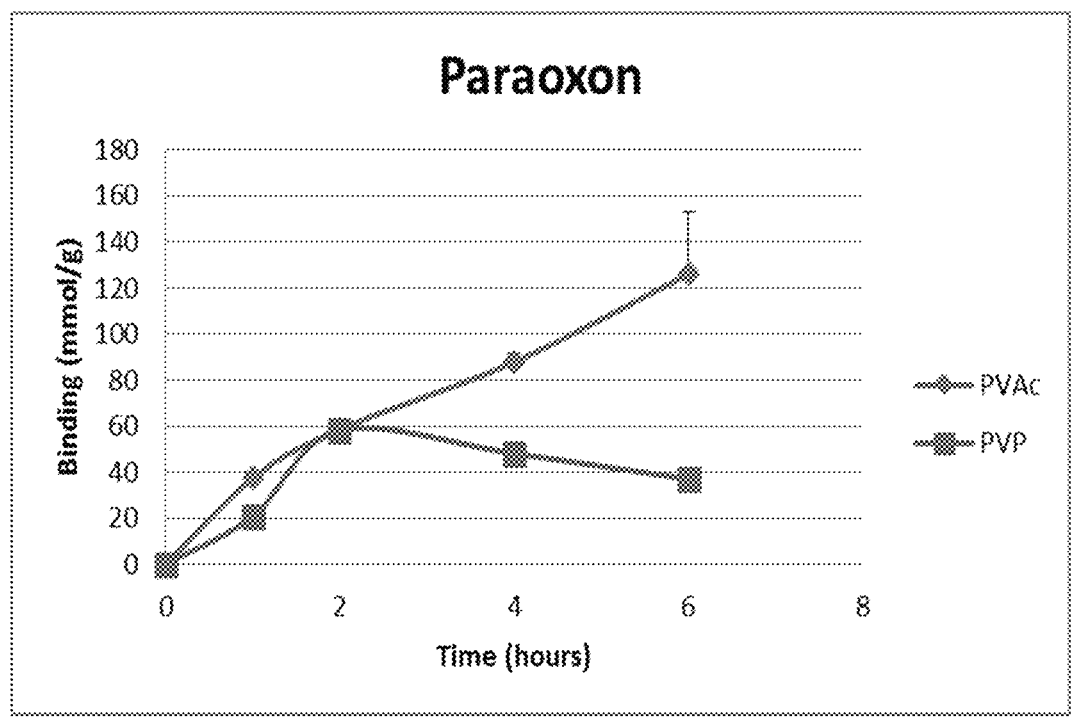
FIG. 18 depicts PVAc and PVP binding affinities to paraoxon for Example 8.
Figure 19:
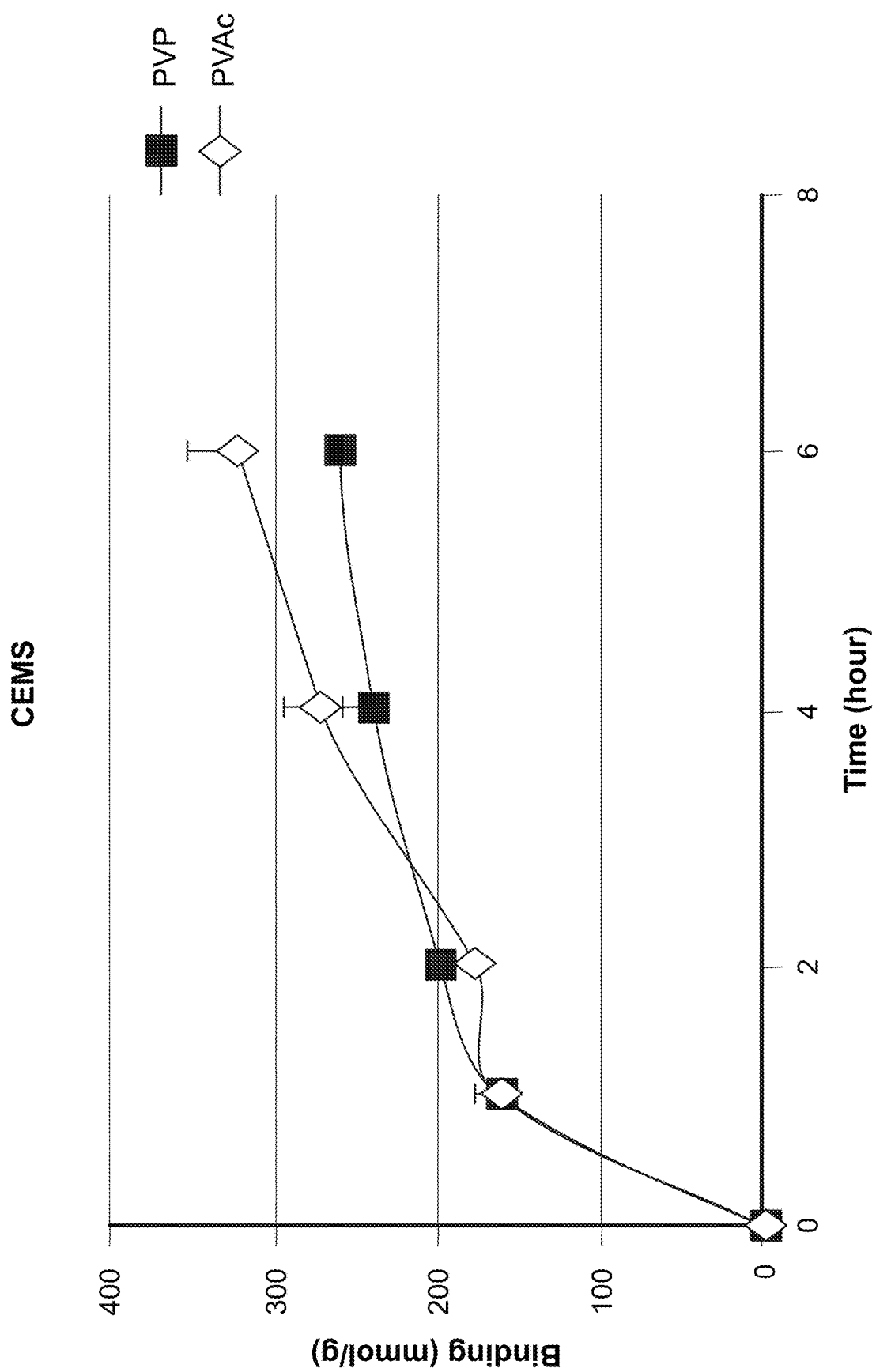
FIG. 19 depicts PVAc and PVP binding affinities to CEMS for Example 8.
Figure 20:
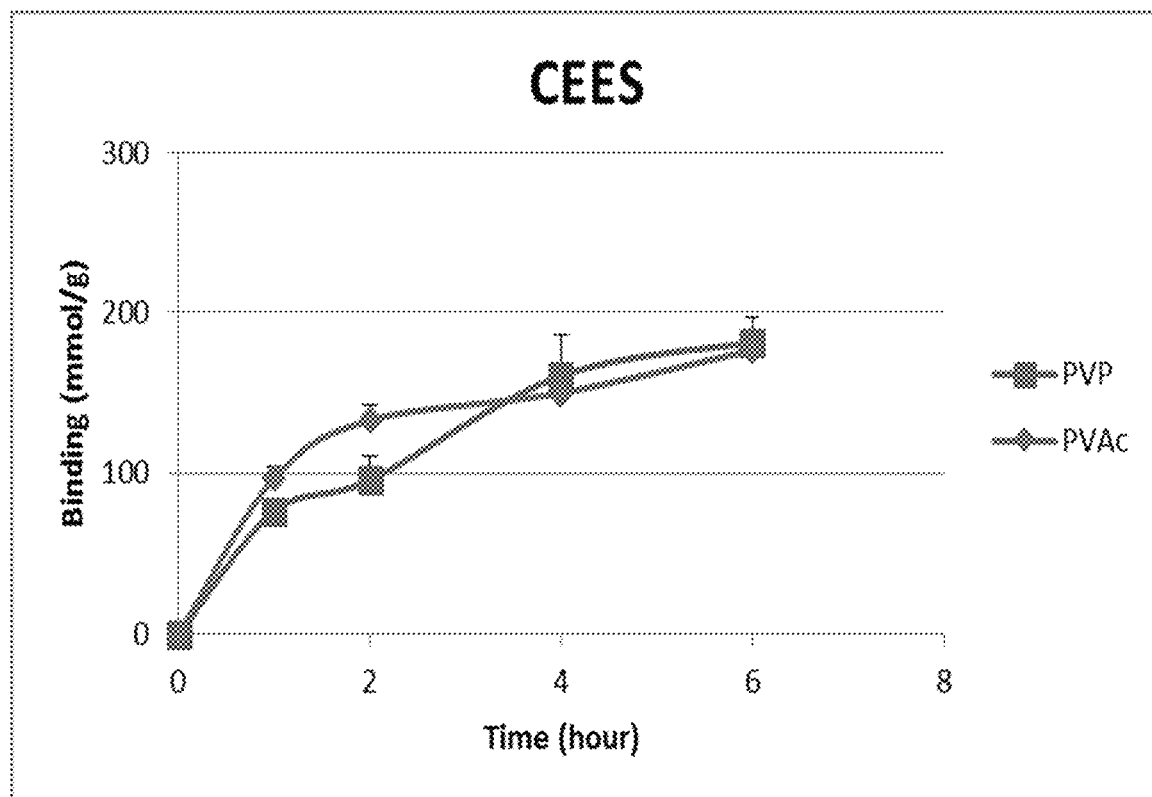
FIG. 20 depicts PVAc and PVP binding affinities to CEES for Example 8.
Figure 21:
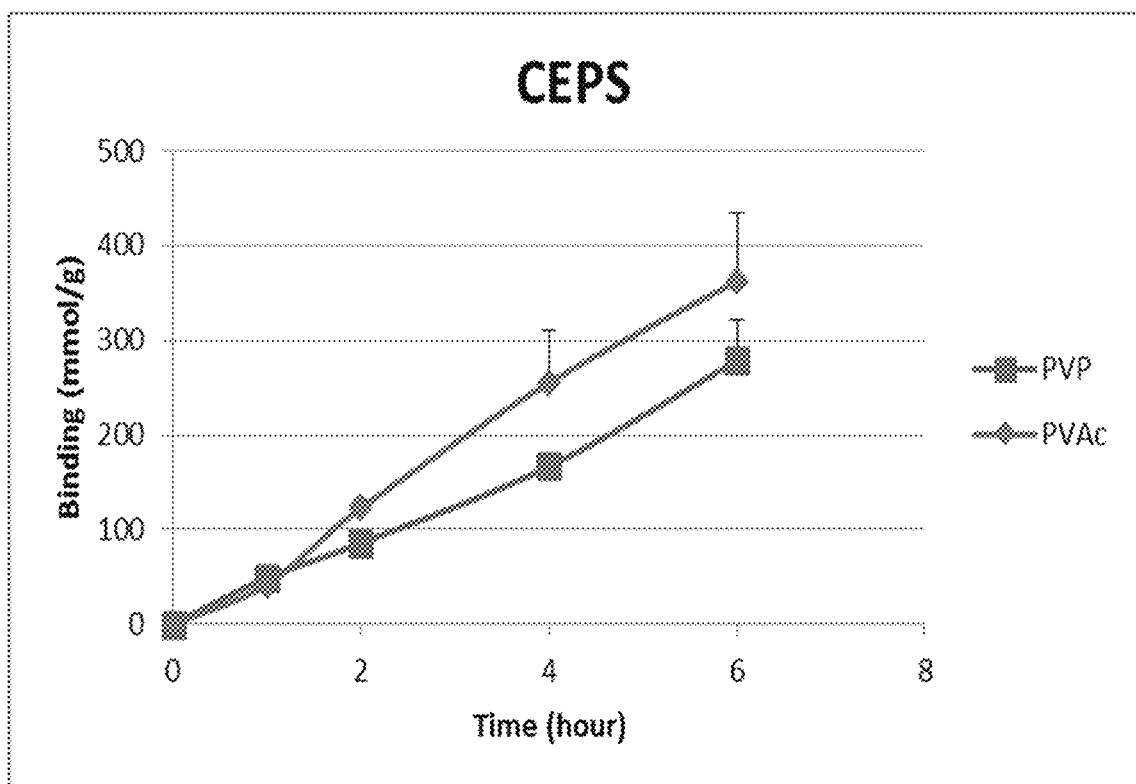
FIG. 21 depicts PVAc and PVP binding affinities to CEPS for Example 8.

FIGS. 15-21 show the binding affinity of PVAc and PVP to the various chemicals tested, i.e., triethyl phosphate, benzoic acid, parathion, paraoxon, CEMS, CEES and CEPS. FIGS. 15 and 16 show PVAc and PVP binding affinities to triethyl phosphate (FIG. 15) and benzoic acid (FIG. 16). FIGS. 17 and 18 show PVAc and PVP binding affinities to parathion (FIG. 17) and paraoxon (FIG. 18). FIGS. 19-21 show PVAc and PVP binding affinities to CEMS (FIG. 19), CEES (FIG. 20) and CEPS (FIG. 21). Each symbol represents the mean±S.D. of 5 replicates.

Three types of binding affinity were observed. PVP showed a greater affinity to triethyl phosphate and benzoic acid (p<0.05) at time points 6 to 20 hours. PVAc showed a greater affinity to parathion and paraoxon (p<0.05) and CEPS than PVP (p<0.05) at time points 4 and 6 hours. There was no significant difference determined between PVAc and PVP on CEMS and CEES absorption (p>0.05). Without wishing to be bound, it is believed that the acetate groups on PVAc are hydrophobic and contributes to the high affinity observed. Also, positive charges in povidone (PVP) are believed to form chemical complexes with numbers of substances and can contribute to the high affinity. Finally, the different characteristics of the two polymers can impart an amphipathic character to the compositions of the present disclosure which can contribute to a high binding affinity.

Example 9

Acetylcholinesterase Inhibition Activity

The detoxification effects of PVAc and PVP on paraoxon by AchE inhibition assays was determined.

A paraoxon solution (0.025 mg/mL) was incubated with 5 mg of PVAc or PVP for 2 hours. The supernatant was then mixed with AchE to determine the enzyme activity and mass equivalent of paraoxon detoxified by polymers (mmol/g).

Figure 22:
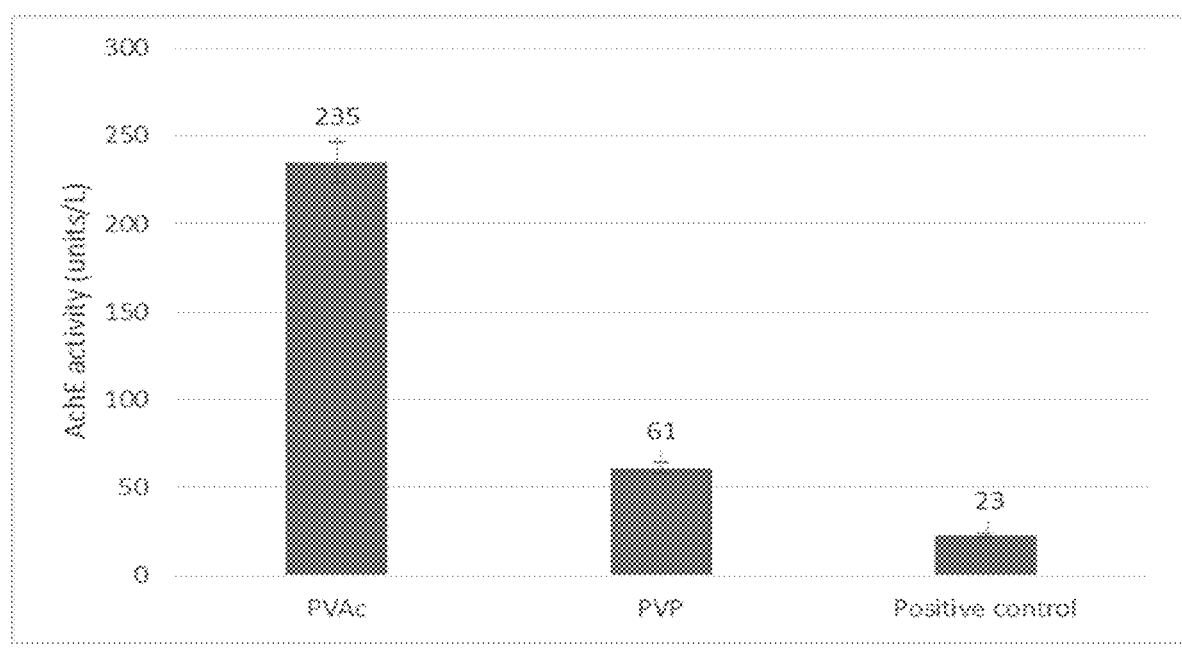
FIG. 22 depicts the amount of Ache activity which remained (units/L) for Example 9.
Figure 23:
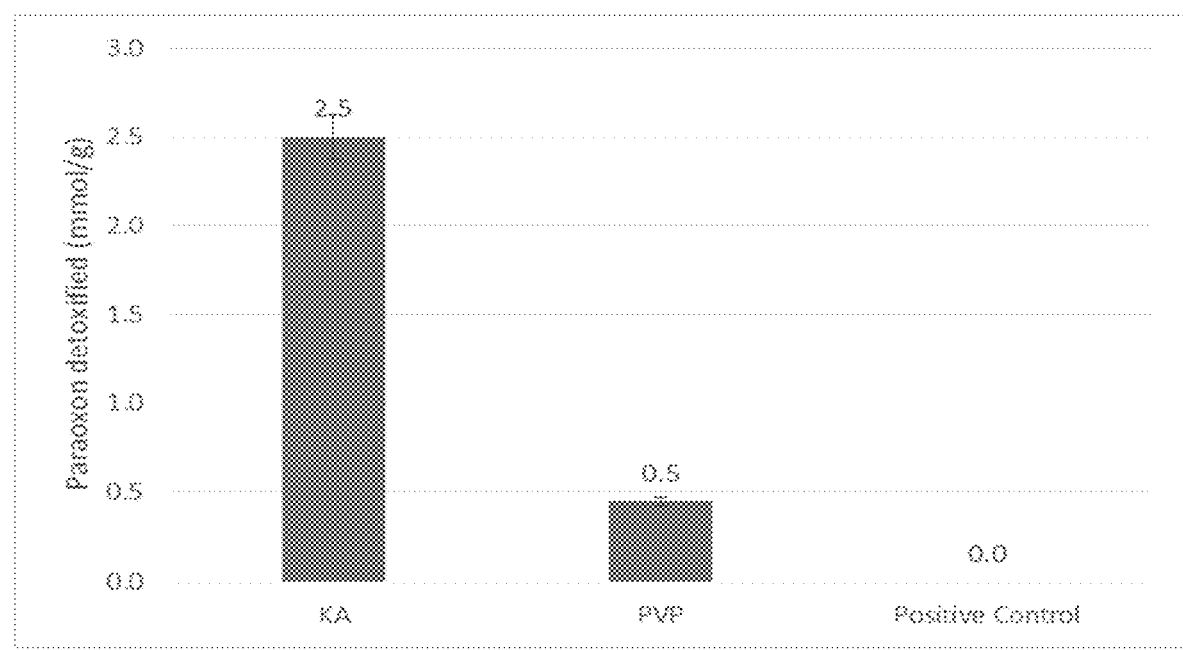
FIG. 23 depicts the amount of detoxification activity on paraoxon (mmol/g) for Example 9.

Paraoxon was incubated with polymer PVAc or PVP for 2 hours and then AchE activity measured. FIGS. 22 and 23 show the results. FIG. 22 shows the amount of Ache activity which remained (units/L). FIG. 23 shows the amount of detoxification activity on paraoxon (mmol/g). Each bar represents the mean±S.D. of 5 replicates. PVAc show greater detoxification ability. PVP has the capability to detoxify paraoxon to reduce AchE inhibition. These materials, and combinations thereof, can provide the compositions and methods of the present disclosure with detoxification properties. They can be contribute to skin surface decontamination function as well as detoxification of organophosphate chemicals.

Example 10

Addition of Nanoparticles for Skin Decontamination and Detoxification

The compositions of the present disclosure were tested with the addition of nanoparticles (NPs). The NPs can be either solid, semi-porous, porous and/or hollow. The NPs can have a relatively larger surface area and space (volume) for absorbance of chemical contaminants. The use of select high efficient materials can improve the performance of the compositions, e.g., DDGel decontamination function.

Figure 24:
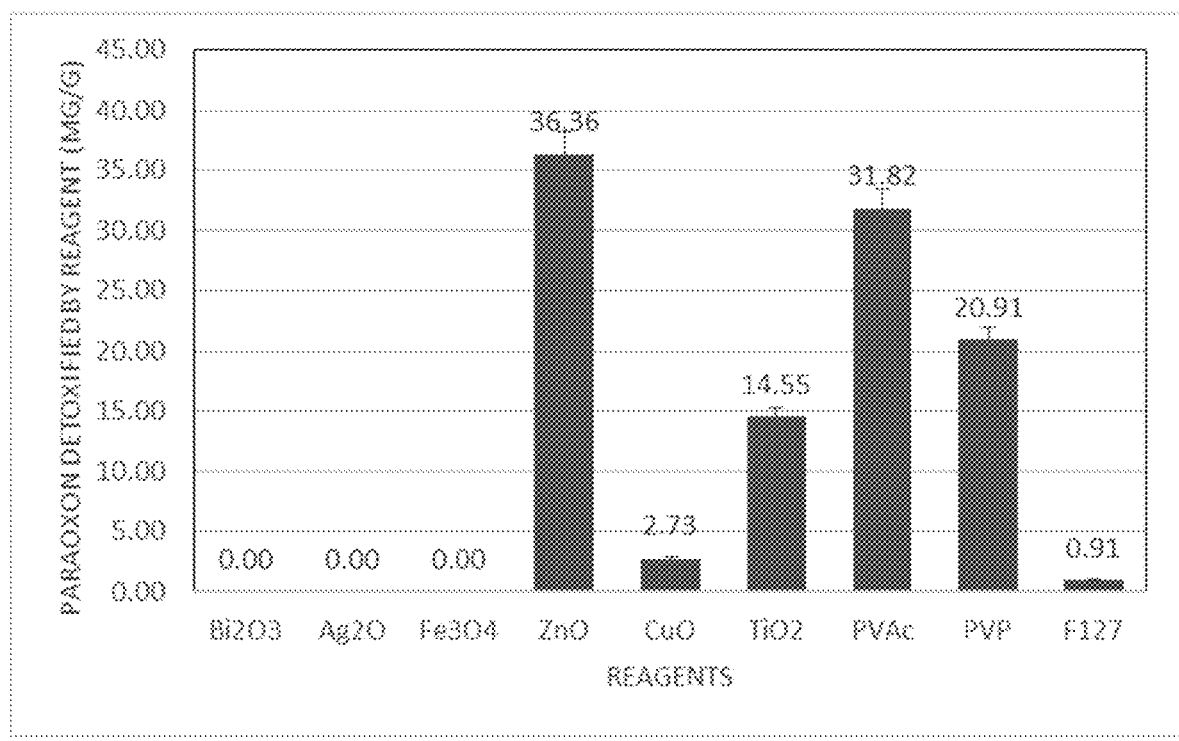
FIG. 24 depicts the paraoxon detoxification performance of the formulation with different NPs added for Example 10.
Figure 25:
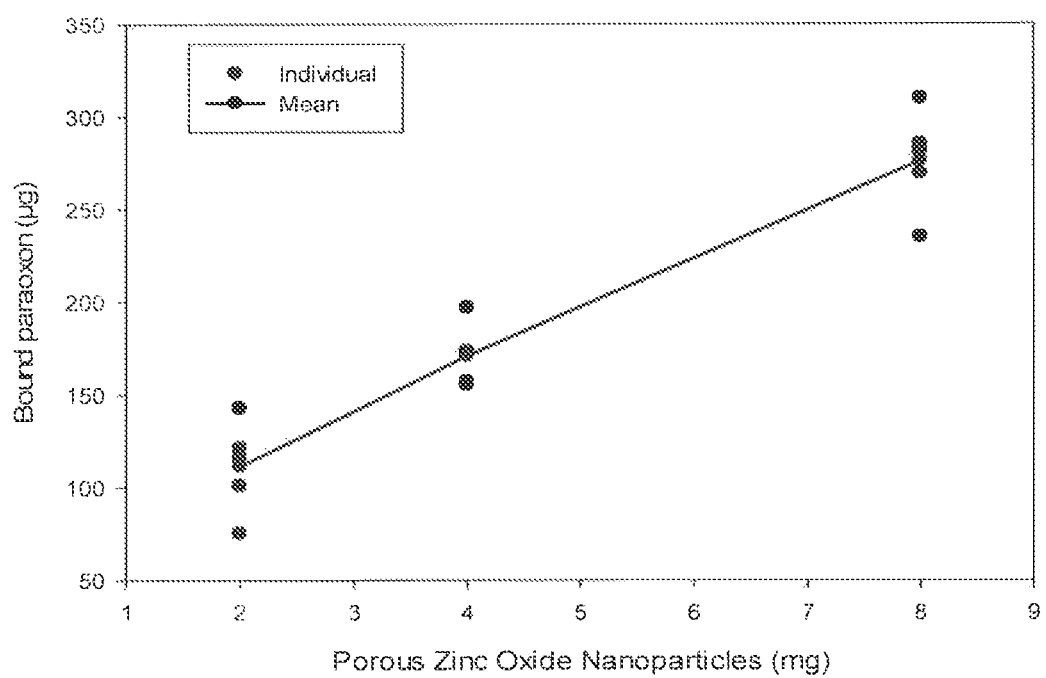
FIG. 25 depicts a linear dose-response curve for the formulation containing porous ZnO nanoparticles for Example 10.

Paraoxon was incubated with polymers and nanoparticles for 2 hours and then AchE activity measured. FIG. 24 shows the paraoxon detoxification performance of the formulation with different NPs added. FIG. 25 shows a linear dose-response curve for the formulation containing porous ZnO nanoparticles (2 mg, 4 mg and 8 mg, respectively). Each symbol represents the mean±S.D. of 5 replicates.

The NPs ZnO and $TiO_2$ showed a similar detoxification activity as polymers PVAc and PVP. In addition, the porous ZnO NPs have a binding capability that is proportional to concentration. The compositions of the present disclosure can be formulated with about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or about 40 wt % NPs, e.g., ZnO, $TiO_2$, CuO). These values can be used to define a range, such as from about 1 wt % to about 30 wt %.

Exemplary formulations of the present disclosure include those listed in Tables 6-9

TABLE 6

| Component | Amount |
| --- | --- |
| Kollidon® SR 30 | 20% |
| KA | 20% |
| PVP | 5% |
| ZnO particles | 0.5% |
| TiO2 | 0.5% |
| Base Cream (Hydrophilic Ointment) | 50% |
| Water | 4% |

TABLE 7

| Component | Amount |
| --- | --- |
| Kollidon ® SR | 27% |
| Lutrol ® F127 | 9% |
| CMC | 2.7% |
| Solid ZnO particles | 3.6% |
| TiO2 | 3.6% |
| Water/Ethanol | Balance |

TABLE 8

| Component | Amount |
| --- | --- |
| Kollidon ® SR | 21.4% |
| Lutrol ® F127 | 7.1% |
| CMC | 2.14% |
| Porous ZnO | 1.5% |
| Bentonite | 3.6% |
| Fuller's Earth | 17.9%? |
| Water/Ethanol | Balance |

TABLE 9

| Component | Amount |
| --- | --- |
| Kollidon ® SR | 21.6% |
| Lutrol ® F127 | 7.4% |
| CMC | 2.16% |
| Solid Rutgers ZnO | 31.25% |
| Water/Ethanol | Balance |

Example 11

Polymer and NP Compositions for Skin Decontamination and Detoxification

The detoxification effects of compositions containing both polymer and NPs on paraoxon by AchE inhibition assays was determined.

About 1 mL of a paraoxon solution (0.025 mg/mL) was incubated with 5 mg of Kollidon® SR, ZnO, $TiO_2$, CuO for up to 24 hours at 37° C. using a water bath shaker. The supernatant was then mixed with AchE to determine the enzyme activity and mass equivalent of paraoxon detoxified by polymers (mmol/g).

Figure 26:
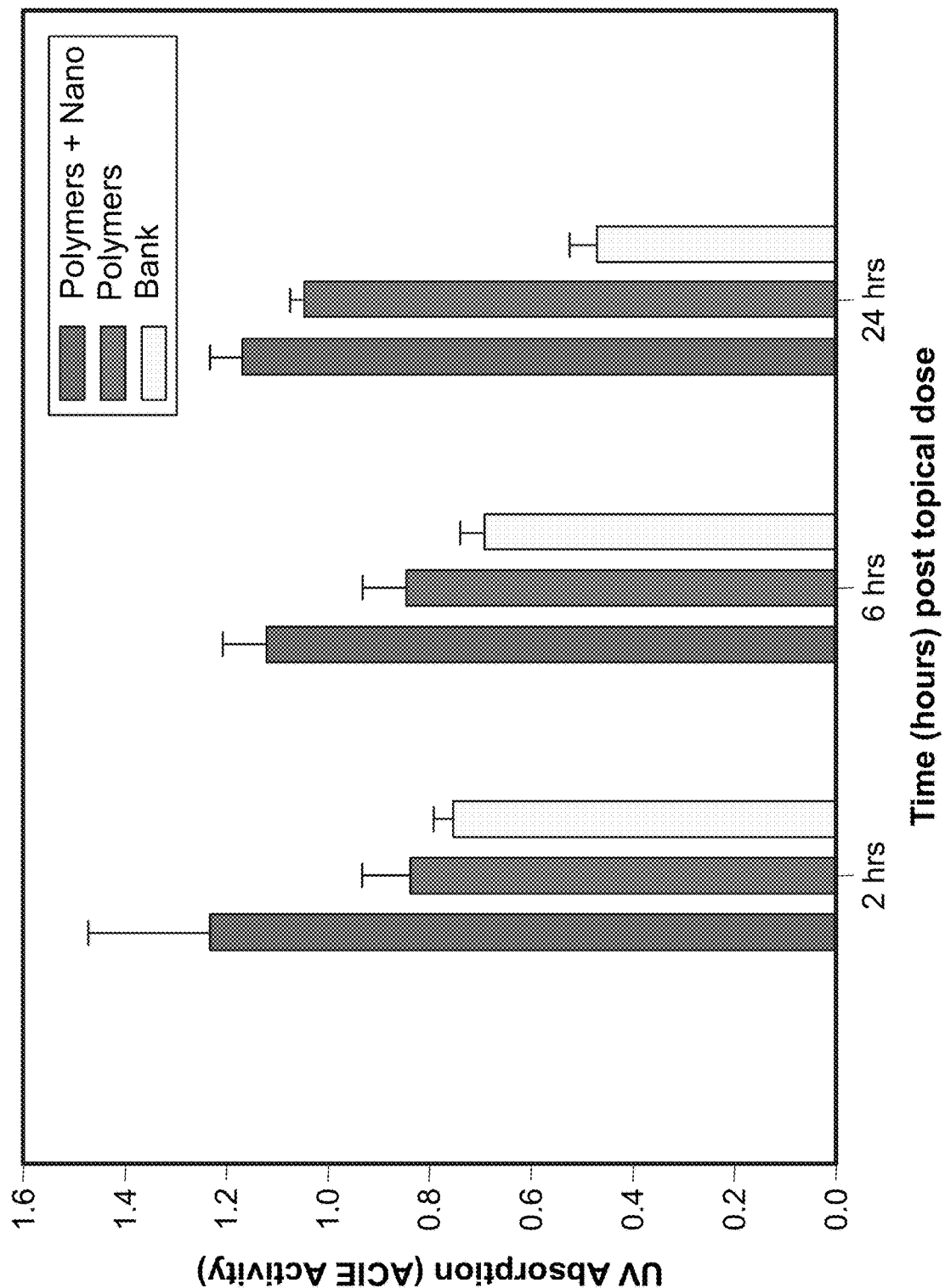
FIG. 26 depicts FIG. 26 show the AchE activity measured for a control (blank), the Kollidon® SR alone and Kollidon® SR plus ZnO and $TiO_2$ for Example 11.

FIG. 26 show the AchE activity measured for a control (blank), the Kollidon® SR alone and Kollidon® SR plus ZnO and $TiO_2$. The results show the addition of NPs enhance the performance of the polymer. The addition of NPs can increase the detoxification of the compositions by about 5%, 10, 15, 20, 25, 30, 40 or about 50%.

Example 12

Nanoparticle Binding Affinity Screening In Vitro Partition/Binding Model

The binding affinity of NPs were tested using a dialysis model. Samples of ZnO, Halloysite, $Bi_2O_3$ and Carbon nanoparticles were incubated with for 24 hours.

2.5% [C14] Paraoxon was incubated with NPs samples including Halloysite nanotubes, bisthmus oxide, carbon and solid ZnO NPs in the following concentrations respectively 0.3%, 1%, 2% and 2%. The incubation was in the form of dialysis model with HPLC grade DD water as dialysate. Samples are incubated for 24 hours at 370° C. in a water bath shaker with continuous shaking. After 24 hours, the dialysis tube is removed from the dialyste then measured with radioactive analyzer to determine the % bound of the initial dose.

The carbon NPs were porous and sized <500 nm (DLS). The ZnO NPs were solid and sized <100 nm. The Halloysite NPs were nanotubes and sized <100 nm. The bismuth (III) oxide NPs were spherical and sized <90-210 nm.

Figure 27:
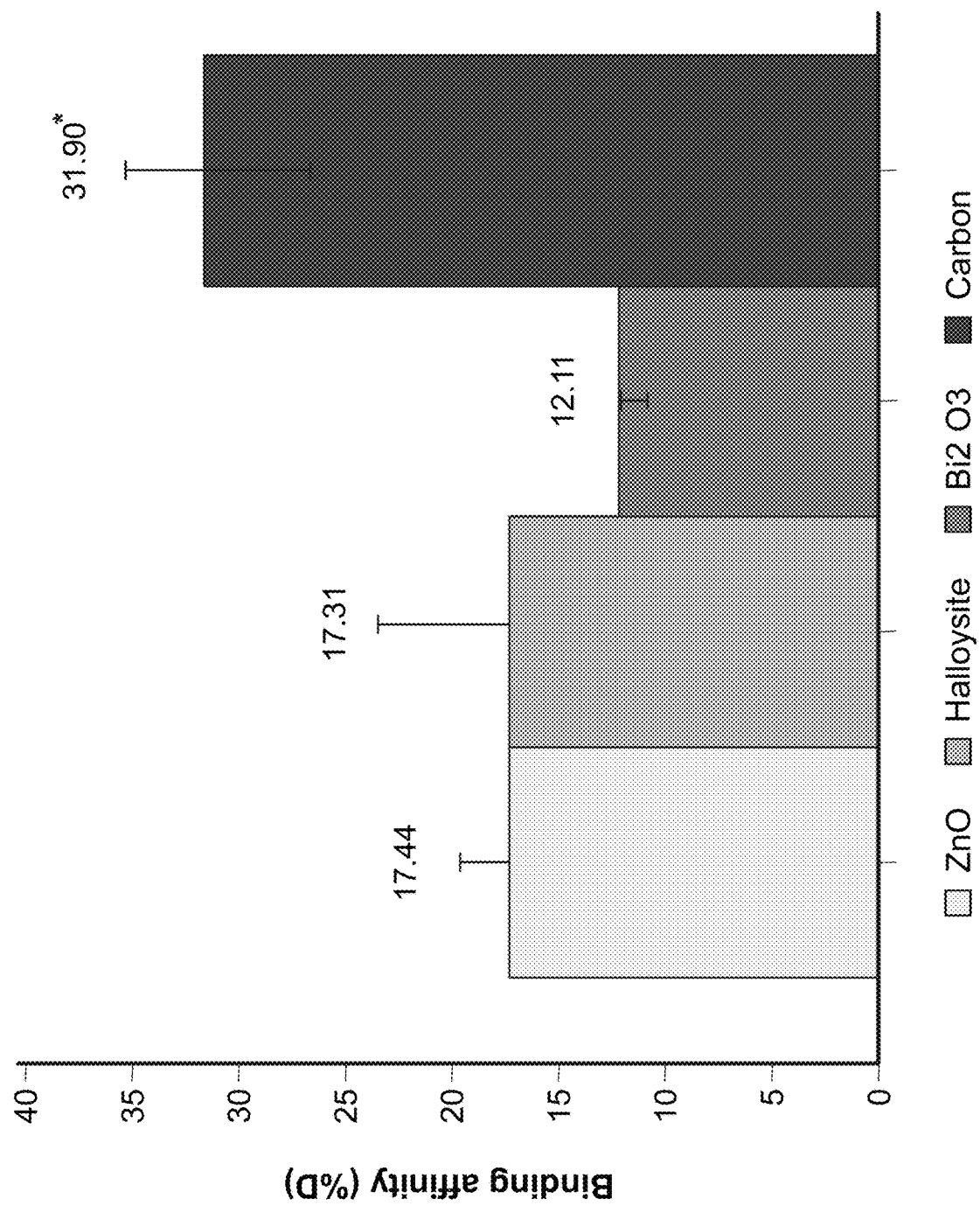
FIG. 27 depicts the binding affinity for the various nanoparticles (NPs) for Example 12.

FIG. 27 shows the binding affinity for the various NPs. The porous structure showed an increased in binding which can be due to an increase in area and volume for absorption.

Example 13

Comparison of [14C]-Benzoic Acid Binding Rates

The binding rate of NPs and polymers were tested. Samples of CMC, ZnO (solid and porous). Lutrol® F127, Kollidon® and Fuller's earth were incubated for 24 hours to reach equilibrium.

[14C] Benzoic Acid was incubated with 5% solution of the following polymers and Nanoparticles; Carboxymethyl Cellulose, Solid ZnO NPs, Lutrol F127, Kollidon, Fuller's Earth and Porous ZnO NPs. The incubation was in the form of dialysis model with HPLC grade DD water as dialysate. Samples were incubated for 24 hours at 370° C. in a water bath shaker with continuous shaking. After 24 hours, the dialysis tube was removed from the dialyste then measured with a radioactive analyzer to determine the % bound of the initial dose.

Figure 28:
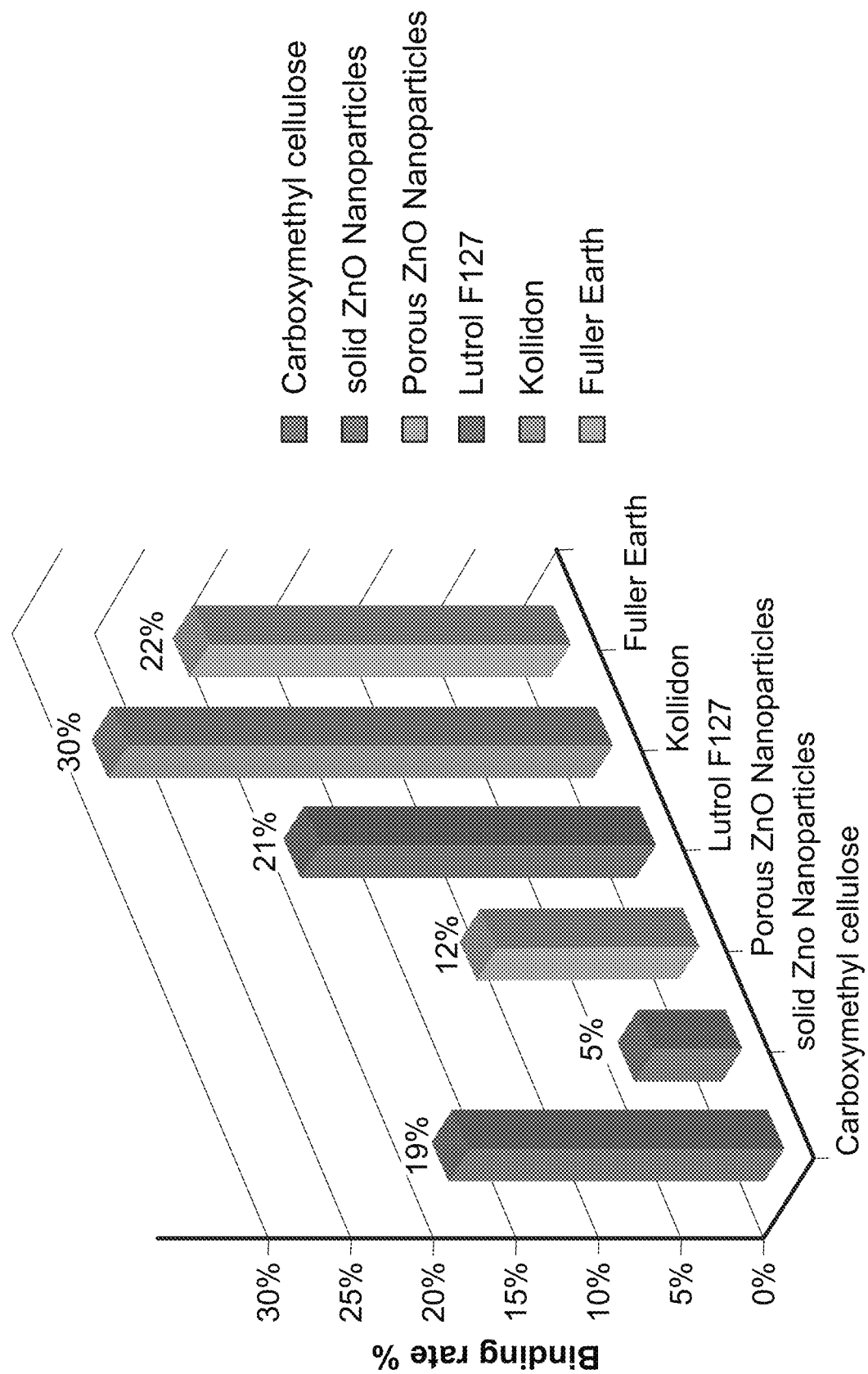
FIG. 28 depicts the binding rate for each component for Example 13.

FIG. 28 shows the binding rate for each component. Each component shows a positive binding rate and each can contribute to the detoxification effect of the present compositions and methods of the present disclosure.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

The invention claimed is:

1. A topical composition consisting essentially of:
    from about 5% to about 20% weight percentage of a mixture of polyvinyl acetate and povidone or pharmaceutically acceptable salt thereof as part of the total weight of the composition;
    from about 1% to about 5% weight percentage of poloxamer 407 or pharmaceutically acceptable salt thereof, as part of the total weight of the composition;
    from about 1% to about 5% weight percentage of carboxymethyl cellulose or pharmaceutically acceptable salt thereof as part of the total weight of the composition;
    from about 10% to about 25% weight percent of Fuller's earth or pharmaceutically acceptable salt thereof as part of the total weight of the composition;
    from about 1% to about 10% weight percent of a phyllosilicate or pharmaceutically acceptable salt thereof as part of the total weight of the composition;
    from about 20% to about 50% weight percent of ethanol as part of the total weight of the composition; and
    from about 10% to about 50% weight percent of water as part of the total weight of the composition.

2. The topical composition of claim 1, further comprising one or more different types of nanoparticles.

3. A kit comprising the topical composition of claim 1 and an applicator.

4. A method of decontaminating a subject in need thereof comprising:
    contacting one or more compositions to the skin of the subject at a location of the subject's body where the skin has been exposed to an agent comprising a radioactive isotope; wherein the composition consisting essentially of:
    from about 5% to about 20% weight percentage of a mixture of polyvinyl acetate and povidone or pharmaceutically acceptable salt thereof as part of the total weight of the composition;
    from about 1% to about 5% weight percentage of poloxamer 407 or pharmaceutically acceptable salt thereof, as part of the total weight of the composition;
    from about 1% to about 5% weight percentage of carboxymethyl cellulose or pharmaceutically acceptable salt thereof as part of the total weight of the composition;
    from about 10% to about 25% weight percent of Fuller's earth or pharmaceutically acceptable salt thereof as part of the total weight of the composition;
    from about 1% to about 10% weight percent of a phyllosilicate or pharmaceutically acceptable salt thereof as part of the total weight of the composition;
    from about 20% to about 50% weight percent of ethanol as part of the total weight of the composition; and
    from about 10% to about 50% weight percent of water as part of the total weight of the composition.

5. The method of claim 4, wherein the step of contacting is performed no less than about 10, 20 or 30 minutes after the subject is exposed to the radioactive isotope.

6. The method of claim 4 further comprising massaging the one or more compositions into the skin of the subject at a location of the subject's body where the skin has been exposed to the radioactive isotope for about 2 minutes after contacting the composition to the skin of the subject.

7. A method of preventing death of a subject exposed to a radioactive isotope comprising contacting one or more compositions to the skin of the subject at a location of the subject's body where the skin has been exposed to the radioactive isotope, wherein the composition consisting essentially of:
    from about 5% to about 20% weight percentage of a mixture of polyvinyl acetate and povidone or pharmaceutically acceptable salt thereof as part of the total weight of the composition;
    from about 1% to about 5% weight percentage of poloxamer 407 or pharmaceutically acceptable salt thereof, as part of the total weight of the composition;
    from about 1% to about 5% weight percentage of carboxymethyl cellulose or pharmaceutically acceptable salt thereof as part of the total weight of the composition;
    from about 10% to about 25% weight percent of Fuller's earth or pharmaceutically acceptable salt thereof as part of the total weight of the composition;
    from about 1% to about 10% weight percent of a phyllosilicate or pharmaceutically acceptable salt thereof as part of the total weight of the composition;
    from about 20% to about 50% weight percent of ethanol as part of the total weight of the composition; and
    from about 10% to about 50% weight percent of water as part of the total weight of the composition.

8. The method of claim 7, wherein the step of contacting is performed no less than about 10, 20 or 30 minutes after the subject is exposed to the radioactive isotope.

9. The method of claim 7, wherein the step of contacting is performed no less than about 5 hours after the subject is exposed to the radioactive isotope.

10. A method of decreasing the amount of exposure of a radioactive isotope to the stratum corneum of a subject exposed to the radioactive isotope comprising contacting any one or more compositions to the skin of the subject at a location of the subject's body where the skin has been exposed to the radioactive isotope, wherein the composition consisting essentially of:
- from about 5% to about 20% weight percentage of a mixture of polyvinyl acetate and povidone or pharmaceutically acceptable salt thereof as part of the total weight of the composition;
- from about 1% to about 5% weight percentage of poloxamer 407 or pharmaceutically acceptable salt thereof, as part of the total weight of the composition;
- from about 1% to about 5% weight percentage of carboxymethyl cellulose or pharmaceutically acceptable salt thereof as part of the total weight of the composition;
- from about 10% to about 25% weight percent of Fuller's earth or pharmaceutically acceptable salt thereof as part of the total weight of the composition;
- from about 1% to about 10% weight percent of a phyllosilicate or pharmaceutically acceptable salt thereof as part of the total weight of the composition;
- from about 20% to about 50% weight percent of ethanol as part of the total weight of the composition; and
- from about 10% to about 50% weight percent of water as part of the total weight of the composition.

11. A method of treating a subject exposed to one or a plurality of radioactive substances, the method comprising contacting a therapeutically effective dose of one or more compositions to the skin of the subject at a location of the subject's body where the skin has been exposed to the radioactive substances, wherein the composition consists essentially of:
- from about 5% to about 20% weight percentage of a mixture of polyvinyl acetate and povidone or pharmaceutically acceptable salt thereof as part of the total weight of the composition;
- from about 1% to about 5% weight percentage of poloxamer 407 or pharmaceutically acceptable salt thereof, as part of the total weight of the composition;
- from about 1% to about 5% weight percentage of carboxymethyl cellulose or pharmaceutically acceptable salt thereof as part of the total weight of the composition;
- from about 10% to about 25% weight percent of Fuller's earth or pharmaceutically acceptable salt thereof as part of the total weight of the composition;
- from about 1% to about 10% weight percent of a phyllosilicate or pharmaceutically acceptable salt thereof as part of the total weight of the composition;
- from about 20% to about 50% weight percent of ethanol as part of the total weight of the composition; and
- from about 10% to about 50% weight percent of water as part of the total weight of the composition.

12. The method of claim 11, wherein contacting any one or more compositions to the skin of the subject at a location of the subject's body where the skin has been exposed to the radioactive substance occurs no less than about 10 minutes prior to washing the one or more compositions from the skin.

* * * * *